US010328051B2

United States Patent
Salama

(10) Patent No.: US 10,328,051 B2
(45) Date of Patent: Jun. 25, 2019

(54) PROLINE OR PROLINE DERIVATIVES FOR THE TREATMENT OF DEMENTIA

(71) Applicant: Zoser B. Salama, Ravensburg (DE)

(72) Inventor: Zoser B. Salama, Ravensburg (DE)

( * ) Notice: Subject to any disclaimer, the term of this patent is extended or adjusted under 35 U.S.C. 154(b) by 0 days.

(21) Appl. No.: 15/511,769

(22) PCT Filed: Sep. 22, 2015

(86) PCT No.: PCT/EP2015/071654
§ 371 (c)(1),
(2) Date: Mar. 16, 2017

(87) PCT Pub. No.: WO2016/046162
PCT Pub. Date: Mar. 31, 2016

(65) Prior Publication Data
US 2017/0239215 A1    Aug. 24, 2017

(30) Foreign Application Priority Data
Sep. 22, 2014  (EP) .................................. 14185777

(51) Int. Cl.
| | | |
|---|---|---|
| *A61K 9/00* | (2006.01) | |
| *A61K 9/14* | (2006.01) | |
| *A61K 45/06* | (2006.01) | |
| *A61K 31/401* | (2006.01) | |

(52) U.S. Cl.
CPC .......... *A61K 31/401* (2013.01); *A61K 9/0053* (2013.01); *A61K 9/14* (2013.01); *A61K 45/06* (2013.01)

(58) Field of Classification Search
CPC .... A61K 31/401; A61K 45/06; A61K 9/0053; A61K 9/14
See application file for complete search history.

(56) References Cited

U.S. PATENT DOCUMENTS

| | | | | |
|---|---|---|---|---|
| 5,506,256 A | * | 4/1996 | Kobayashi | C07D 207/08 514/422 |
| 2005/0096385 A1 | * | 5/2005 | Kong | C07C 307/02 514/464 |
| 2007/0099982 A1 | * | 5/2007 | Salama | A61K 31/401 514/423 |
| 2008/0176923 A1 | * | 7/2008 | Salama | C07D 207/16 514/423 |

FOREIGN PATENT DOCUMENTS

| | | |
|---|---|---|
| JP | 2011242217 A | 12/2011 |
| WO | 2005038453 A1 | 4/2005 |

OTHER PUBLICATIONS

Perry T. L. et al., "Failure of aminooxyacetic acid therapy in Huntington disease", Neurology, Jul. 1, 1980, p. 774, vol. 30, issue 7, Lippincott Williams & Wilkins, Philadelphia, USA.
Vogelsang G. D. et al., "Discovery of hydroxyproline and an actin determinant in the insoluble paired helical filaments of Alzheimer brain", Abstracts of the Annual Meeting of the Society for Neuroscience, Jan. 1, 1988, p. 1087, vol. 14, issue 2, Society for Neuroscience, Washington D.C., USA.
Kalaria et al., "Increased collagen content of cerebral microvessels in Alzheimer's disease", Brain Research, Dec. 24, 1995, pp. 349-352, vol. 705, issues 1-2, Elsevier, Amsterdam, Netherlands.
Molina J A et al., "Cerebrospinal fluid levels of non-neurotransmitter amino acids in patients with Alzheimer's disease", Jounral of Neural Transmission, Jan. 1, 1998, pp. 279-286, vol. 105, issues 2-3, Springer, Vienna, Austria.
Walker, Lary C., Ph.D., et al., "Mechanisms of Protein Seeding in Neurodegenerative Diseases", JAMA Neurology, vol. 70, No. 3, pp. 1-2, Mar. 1, 2013.
International Search Report dated Feb. 9, 2016 for International Application No. PCT/EP2015/071654 filed Sep. 22, 2015.

* cited by examiner

*Primary Examiner* — Snigdha Maewall
(74) *Attorney, Agent, or Firm* — Avery N. Goldstein; Blue Filament Law PLLC

(57) ABSTRACT

A pharmaceutical compositions including proline or proline derivatives is provided. A method for the treatment of dementia, Alzheimer's and neurodegenerative diseases with the compositions is also provided.

15 Claims, 13 Drawing Sheets

1. Pancreas
2. kidneys and adrenal glands
3. salivary glands
4. lymph nodes (Mesenteric)
5. thymus
6. caecum
7. small intestine
8. spleen
9. large intestine
10. liver
11. lung
12. urinary bladder
13. thyroid
14. stomach
15. skin
16. aorta
17. bone and bone marrow
18. such cutaneous fat
19. prostate
20. muscle
21. eyes and harderian glands
22. heart
23. both testes
24. brain and pituitary gland
25. brown fat
26. whole blood 13.1

13.2

13.3

Figure 14 14.1
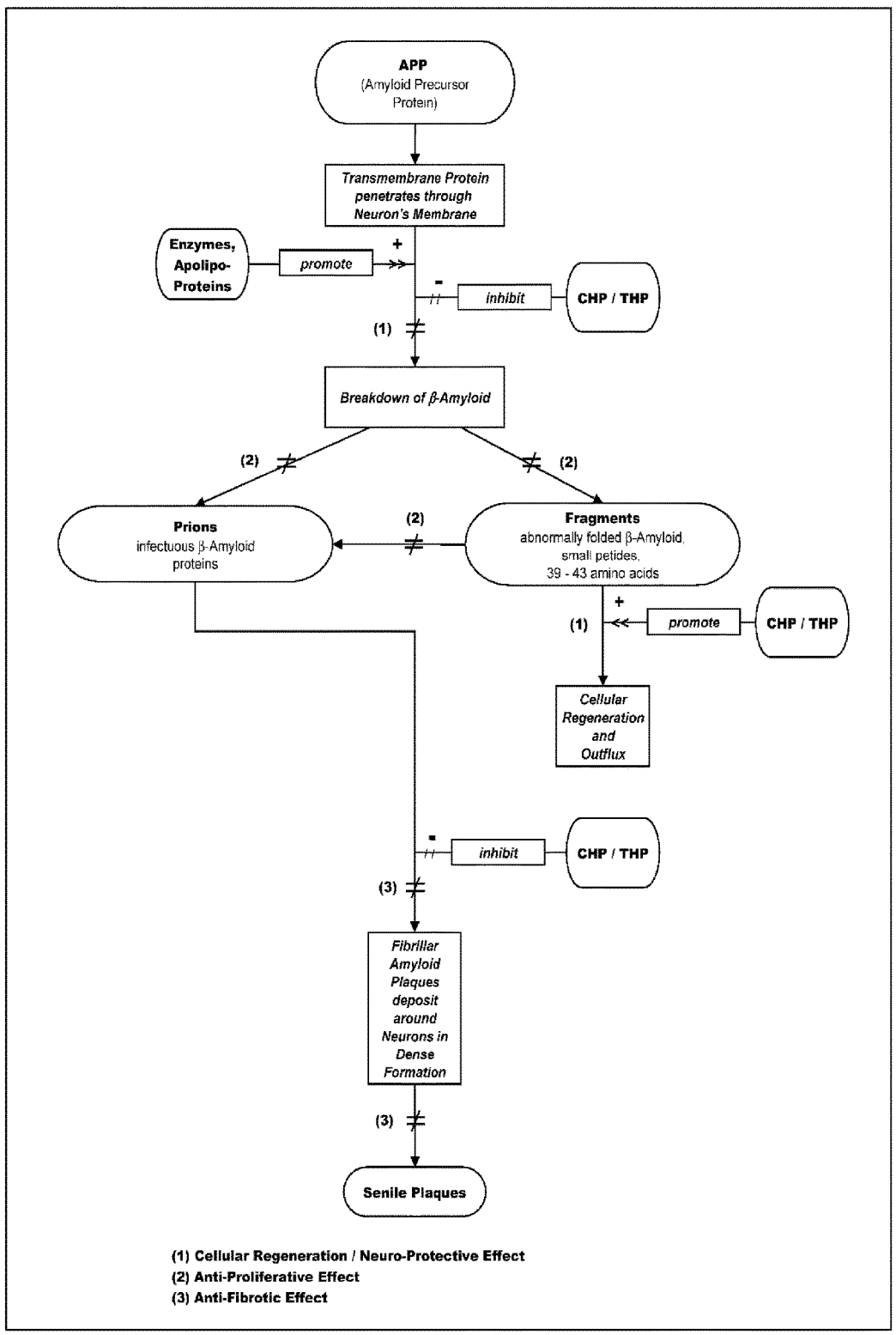

14.2

PROLINE OR PROLINE DERIVATIVES FOR THE TREATMENT OF DEMENTIA

The invention relates to pharmaceutical composition comprising proline derivatives, preferably Cis-4-hydroxy-I-proline (CHP) and trans-4-Hydroxy-L-proline (THP), or proline, or their salts, esters, isomers, racemates, enantiomers or pro-drugs thereof, and to the use of said compositions for the treatment of dementia, Alzheimer's and neurodegenerative diseases. The invention further relates to methods for producing said compounds, pharmaceutical agents and compositions.

The present invention is based on the surprising and unexpected development that Cis-4-hydroxy-I-proline (CHP) and trans-4-Hydroxy-L-proline (THP) can prevent, attenuate and/or therapeutically treat the symptoms of said dementia, Alzheimer's Disease and neurodegenerative diseases.

BACKGROUND OF THE INVENTION

Dementia is a loss of mental ability severe enough to interfere with normal activities of daily living, lasting more than six months, not present since birth, and not associated with a loss or alteration of consciousness. Dementia is a group of symptoms caused by gradual death of brain cells. The loss of cognitive abilities that occurs with dementia leads to impairments in memory, reasoning, planning, and behavior. While the overwhelming number of people with dementia are elderly, dementia is not an inevitable part of aging; instead, dementia is caused by specific brain diseases. Alzheimer's disease (AD) is the most common cause, followed by vascular or multi-infarct dementia. The prevalence of dementia is difficult to determine, partly because of differences in definition among different studies and partly because there is some normal decline in functional ability with age. The prevalence of dementia roughly doubles for every five years of age beginning at age 60. Dementia affects about 1% of people between ages 60 and 64, 5-8% of all people between ages 65 and 74, up to 20% of those between 75 and 84, and between 30% and 50% of those age 85 and older. About 60% of nursing home patients have dementia.

The Alzheimer's Association estimates that in 2007, 5.1 million Americans were living with a diagnosis of AD. That number expected to grow substantially as the population ages.

The cost of dementia can be considerable. While most people with dementia are retired and are not affected by income losses from their disease, the cost of care often is enormous. Financial burdens include lost wages for family caregivers, medical supplies and drugs, and home modifications to ensure safety. Nursing home care may cost several thousand dollars a month or more. The psychological cost is not as easily quantifiable but can be even more profound. The person with dementia loses control of many of the essential features of his life and personality, and loved ones lose a family member even as they continue to cope with the burdens of increasing dependence and unpredictability.

Dementia usually is caused by degeneration in the cerebral cortex, the part of the brain responsible for thoughts, memories, actions, and personality. Death of brain cells in this region leads to the cognitive impairment that characterizes dementia. The most common cause of dementia is AD, accounting for one-half to three-fourths of all cases. The brain of a person with AD becomes clogged with two abnormal structures called neurofibrillary tangles and senile plaques. Neurofibrillary tangles are twisted masses of protein fibers inside nerve cells (neurons). Senile plaques are composed of parts of neurons surrounding a group of proteins called beta-amyloid deposits. Why these structures develop is unknown. Current research indicates possible roles for inflammation, blood flow restriction, and molecular fragments known as free radicals.

Several genes have been associated with higher incidences of AD, although the exact role of these genes still is unclear. Discovered by researchers at Duke University in the early 1990s, potentially the most important genetic link to AD is on chromosome 19. A gene on this chromosome, called APOE (apolipoprotein E), codes for a protein involved in transporting lipids (fats) into neurons. Certain variations of this gene appear to increase the chance for developing AD and/or lower the age at which symptoms occur. Researchers believe that as many as seven other AD risk-factor genes exist. In 2007, scientists identified a possible risk factor in four new AD-related regions in the human genome. In these regions, one out of several hundred genes may be a risk factor. One gene called SORL 1 has drawn particular research attention. This gene is involved regulating the transport of certain proteins in the cell. As of 2009, the role SORL 1 in the development of AD remained under study.

Vascular dementia is estimated to cause from 5-30% of all dementias. It occurs from decrease in blood flow to the brain, most commonly due to a series of small strokes (multi-infarct dementia). Other cerebrovascular causes include vasculitis from syphilis, Lyme disease, or systemic lupus erythematosus (SLE); subdural hematoma; and subarachnoid hemorrhage. Because of the usually sudden nature of its cause, the symptoms of vascular dementia tend to begin more abruptly than those of Alzheimer's dementia. Symptoms may progress stepwise with the occurrence of new strokes. Unlike AD, the incidence of vascular dementia is lower after age 75.

Conditions that may cause dementia include: AIDS, Parkinson's disease, Lewy body disease, Pick's disease, Huntington's disease, Creutzfeldt-Jakob disease, brain tumor, hydrocephalus, head trauma, multiple sclerosis, prolonged abuse of alcohol or other drugs, vitamin deficiency: thiamin, niacin, or $B_{12}$, hypothyroidism, and hypercalcemia.

Consequences of Dementia and Alzheimer's Disease

Dementia is marked by a gradual impoverishment of thought and other mental activities. Losses eventually affect virtually every aspect of mental life. The slow progression of dementia is in contrast with delirium, which involves some of the same symptoms, but has a very rapid onset and fluctuating course with alteration in the level of consciousness. However, delirium may occur with dementia, especially since the person with dementia is more susceptible to the delirium-inducing effects of many types of drugs.

Symptoms of dementia include: Memory losses, impaired abstraction and planning, language and comprehension disturbances, poor judgment impaired orientation ability, decreased attention and increased restlessness, behavioral changes and psychosis, depression is common in the elderly and can be mistaken for dementia.

"Alzheimer's disease (AD)", also known in medical literature and is defined for the purposes of the present invention as the most common form of dementia. There is no cure for the disease, which worsens as progresses and eventually leads to death. Most often, AD is diagnosed in people over 65 years of age, although the less-prevalent early-onset Alzheimer's can occur much earlier. In 2006, there were 26.6 million sufferers worldwide. Alzheimer's is predicted to affect 1 in 85 people globally by 2050. Because AD cannot be cured and is degenerative, the sufferer relies on others for assistance. The role of the main caregiver is often taken by the spouse or a close relative. Alzheimer's disease is known for placing a great burden on caregivers; the pressures can be wide-ranging, involving social, psychological, physical, and economic elements of the caregivers life. In developed countries, AD is one of the most costly diseases to society.

The cause for most Alzheimer's cases is still essentially unknown (except for 1% to 5% of cases where genetic differences have been identified). Several competing hypotheses exist trying to explain the cause of the disease:

Cholinergic Hypothesis

The oldest, on which most currently available drug therapies are based, is the cholinergic hypothesis, which proposes that AD is caused by reduced synthesis of the neurotransmitter acetylcholine. The cholinergic hypothesis has not maintained widespread support, largely because medications intended to treat acetylcholine deficiency have not been very effective. Other cholinergic effects have also been proposed, for example, initiation of large-scale aggregation of amyloid, leading to generalised neuroinflammation.

Amyloid Hypothesis

In 1991, the amyloid hypothesis postulated that beta-amyloid (βA) deposits are the fundamental cause of the disease. Support for this postulate comes from the location of the gene for the amyloid precursor protein (APP) on chromosome 21, together with the fact that people with trisomy 21 (Down Syndrome) who have an extra gene copy almost universally exhibit AD by 40 years of age. Also, a specific isoform of apolipoprotein, APOE4, is a major genetic risk factor for AD. Whilst apolipoproteins enhance the breakdown of beta amyloid, some isoforms are not very effective at this task (such as APOE4), leading to excess amyloid buildup in the brain. Further evidence comes from the finding that transgenic mice that express a mutant form of the human APP gene develop fibrillar amyloid plaques and Alzheimer's-like brain pathology with spatial learning deficits.

Tau Hypothesis

The tau hypothesis is the idea that tau protein abnormalities initiate the disease cascade. In this model, hyperphosphorylated tau begins to pair with other threads of tau. Eventually, they form neurofibrillary tangles inside nerve cell bodies. When this occurs, the microtubules disintegrate, collapsing the neuron's transport system. This may result first in malfunctions in biochemical communication between neurons and later in the death of the cells.

Other Hypotheses

Herpes simplex virus type 1 has also been proposed to play a causative role in people carrying the susceptible versions of the apoE gene. Another hypothesis asserts that the disease may be caused by age-related myelin breakdown in the brain. Iron released during myelin breakdown is hypothesised to cause further damage. Homeostatic myelin repair processes contribute to the development of proteinaceous deposits such as beta-amyloid and tau. Oxidative stress and dys-homeostasis of biometal (biology) metabolism may be significant in the formation of the pathology.

Biochemistry of Alzheimer's Disease

Enzymes act on the APP (amyloid precursor protein) and cut it into fragments. The beta-amyloid fragment is crucial in the formation of senile plaques in AD. Alzheimer's disease has been identified as a protein misfolding disease (proteopathy), caused by accumulation of abnormally folded amyloid beta and amyloid tau proteins in the brain. Plaques are made up of small peptides, 39-43 amino acids in length, called beta-amyloid (Aβ). Beta-amyloid is a fragment from a larger protein called amyloid precursor protein (APP), a transmembrane protein that penetrates through the neuron's membrane. APP is critical to neuron growth, survival and post-injury repair. In Alzheimer's disease, an unknown process causes APP to be divided into smaller fragments by enzymes through proteolysis. One of these fragments gives rise to fibrils of beta-amyloid, which form clumps that deposit outside neurons in dense formations known as senile plaques. In Alzheimer's disease, changes in tau protein lead to the disintegration of microtubules in brain cells.

AD is also considered a tauopathy due to abnormal aggregation of the tau protein. Every neuron has a cytoskeleton, an internal support structure partly made up of structures called microtubules. These microtubules act like tracks, guiding nutrients and molecules from the body of the cell to the ends of the axon and back. A protein called tau stabilises the microtubules when phosphorylated, and is therefore called a microtubule-associated protein. In AD, tau undergoes chemical changes, becoming hyperphosphorylated; it then begins to pair with other threads, creating neurofibrillary tangles and disintegrating the neuron's transport system.

Pharmacological Approaches for the Treatment of Dementia and Alzheimer's Disease Treatment of dementia begins with treatment of the underlying disease, where possible. The underlying causes of nutritional, hormonal, tumor-caused, and drug-related dementias may be reversible to some extent. Treatment for stroke-related dementia begins by minimizing the risk of further strokes through smoking cessation, aspirin therapy, and treatment of hypertension, for instance. Alzheimer's disease is, as of 2009, incurable; however, early diagnosis and prompt intervention can slow decline from AD and extend the period during which people the disease can maintain independent functioning. As of 2009, the United States Food and Drug Administration (FDA) had approved five prescription drugs for the treatment of AD symptoms. Four of these are used to treat mild to moderate AD. They are galantamine (Razadyne formerly known as Reminyl), rivastigmine (Exelon), donepezil (Aricept), and tacrine (Cognex). Tacrine, however, is rarely prescribed because of safety issues. These drugs all act by increasing the level of chemical signaling molecules (neurotransmitters) in the brain to help compensate for decreased communication ability among nerve cells. The fifth drug, memantine (Namenda), is used to treat moderate to severe AD. It acts by regulating a chemical in the brain called glutamate.

None of these drugs cure or stop AD. In some individuals, they do slow the progression of symptoms by modestly increasing cognition and improving the individual's ability to perform normal activities of daily living. Slowing or reversing dementia is an area of active research. Clinical trials of new drugs and therapies are ongoing.

Antioxidants, which act to protect against oxidative damage caused by free radicals, have been shown to inhibit toxic effects of beta-amyloid in laboratory tissue cultures. Vitamin E, an antioxidant, is thought to delay AD onset. However, it is not yet clear whether this is due to the specific action of vitamin E on brain cells or to an increase in the overall health of those taking it.

Research is being conducted to determine if vitamin E or other antioxidants may delay or prevent AD.

*Ginkgo* extract, derived from the leaves of the *Ginkgo biloba* tree, appeared to be one of the more promising alternative treatments for AD. A 1997 study of patients with dementia seemed to show that *ginkgo* extract could improve their symptoms, although the study was criticized for certain flaws in its method. Unfortunately, a large-scale, well-designed, follow-up study released in 2008 showed that *Ginkgo* extract neither prevented nor delayed AD.

Some alternative practitioners advise people with AD to take supplements of phosphatidylcholine, vitamin $B_{12}$, gotu kola, *ginseng*, St. John's Wort, rosemary, saiko-keishi-to-shakuyaku (A Japanese herbal mixture), and folic acid. As of 2009, none of these alternative therapies met the safety and effectiveness standards of conventional Western medicine as a treatment for AD. Therefore Dementia Diseases are a significant problem in the world. Although modest advances have been made in dementia detection and treatment, no drug universally successful preventive or therapeutic method is currently available. Unfortunately, that none of the developed and used drugs and method can cure or stop dementia diseases particularly Alzheimer, in both men and women. In the fight against dementia diseases, numerous techniques have been developed and are subject of current research directed to understanding the nature and cause of the disease and to providing methods for the control or cure thereof. Although a number of agents have been evaluated, the prevention and treatment of dementia diseases remains fraught with complications which often present an array of suboptimal treatment choices.

There is a great need for pharmaceutical therapies that can be used to treat patients with the above mentioned disorders, including patients who do not respond to currently available therapies, as well as for pharmaceutical therapies that improve the efficacy of currently available treatment regimes. Pharmacological strategies to have efficacy on the prophylaxis, prevention, attenuation, reduction, elimination and/or therapeutical treatment the symptoms of said dementia and/or Alzheimer's would therefore have an enormous impact on the quality of life (QoL) and on public health.

SUMMARY OF THE INVENTION

In light of the prior art, the technical problem underlying the present invention is to provide alternative or improved chemical compounds which demonstrate anti-dementia and/or anti-Alzheimer's treatments, and from these compounds generate a pharmaceutical composition which could then be used for the prophylaxis, prevention, reduction, attenuation, elimination and or therapy the symptoms of said dementia and Alzheimer's Disease (AD). It is also an object of the present invention to provide an anti-dementia and anti-alzheimer's composition which can be administered with other pharmaceutical agents using the different routes of administrations.

It is also an object of the present invention to provide a method for the early diagnosis of the dementia, neurodegenerative diseases, neuromuscular degenerative disorders and/or Schizophrenia by the determination of the compound of the invention in the biological materials such as blood, and Cerebrospinal Fluid (CSF).

This problem is solved by the features of the independent claims. Preferred embodiments of the present invention are provided by the dependent claims.

The present invention therefore relates to a pharmaceutical composition comprising a proline derivative selected from cis-4-hydroxy-L-proline (CHP) or trans-4-hydroxy-L-proline (THP), or derivatives thereof, or proline, for use as a medicament in the treatment of dementia.

The invention further provides pharmaceutical compositions, which contain a therapeutically effective amount of proline or proline derivatives or their salts, esters, isomers or prodrugs with or without the combination with other agents. In particular, this invention relates to methods for the prophylaxis, prophylaxis, prevention, reduction, attenuation, elimination and or therapy the symptoms of said dementia and alzheimer of said dementia and Alzheimer's diseases by administration of proline or a proline derivative preferably cis-4-hydroxy-I-proline, 4-hydroxy-1-methyl-proline, 1-methyl-4-phenylamine carbonyloxy proline or 1-methyl-4-phenylamine carbonyloxy-proline, or one of the salts, or isomers, esters, or prodrugs thereof in combination with a pharmaceutical agent.

Other preferred proline derivatives which may be used according to the invention are cis-4-hydroxymethyl-I-proline, trans-4-hydroxymethyl-D-proline, trans-4-hydroxymethyl-I-proline, trans-4-methyl-I-proline and cis-3-Amino-I-proline or any corresponding salts thereof. Proline and its derivatives, as used according to the invention, are known compounds which are commercially available or can be prepared using chemical or biotech methods. The preferred proline derivatives used include esters especially methyl, ethyl, isopropyl, butyl or isobutyl esters.

More particularly the invention relates to oral, transmucosal, transbuccal, local, intravenous, transdermal and intranasal dosage form administrations of cis-4-hydroxy-L-proline (CHP), its salts, isomers, enantiomers and/or derivatives.

In light of the prior art the technical problem underlying the present invention was to provide methods and compositions and/or alternative and/or chemical compounds for the prophylaxis, prevention, reduction, attenuation, elimination and or therapy of the symptoms of said dementia, Alzeheimer's Disease (AD), neurodegenerative and/or neuromuscular diseases.

It is also an object of the present invention to provide an anti-dementia and/or anti-alzheimer's compositions which can be administered with or without other pharmaceutical agents using the different routes of administrations.

Therefore, one object of the invention is to provide a pharmaceutical composition comprising cis-4-hydroxy-I-proline, its derivatives, salts, isomeres, and/or enantiomers thereof for use as a medicament in the prophylaxis, prevention, reduction, attenuation, elimination and or therapy the symptoms of said dementia and Alzeheimer's Disease (AD) characterised in that said treatment comprises preferably oral, transmucosal, transbuccal, parental, transdermal, rectal or intranasal administration of said pharmaceutical composition to a subject in need of said treatment.

It is also an object of the invention is to provide a composition wherein the carrier is selected from the group consisting of fillers, diluents, binders, humectants, disintegrants, dissolution retarders, absorption enhancers, wetting agents, adsorbents, lubricants and combinations thereof.

In a preferred embodiment of the invention the proline derivative or derivative of CHP or THP is defined as being selected from the group consisting of cis-4-hydroxy-L-proline (CHP), trans-4-hydroxy-L-proline (THP), 4-hydroxy-1-methyl-proline, 1-methyl-4-phenylamine carbonyloxy-proline, 1-methyl-4-phenylamine carbonyloxy-proline, cis-4-hydroxymethyl-I-proline, trans-4-hydroxymethyl-D-proline, trans-4-hydroxymethyl-I-proline, trans-4-methyl-I-proline, cis-3-Amino-1-proline, 1-Methyl-4-phenylaminocarbonyl-oxy-proline-ethylester, 1-Methyl-4-phenylaminocarbonyl-oxy-proline-isobutylester, 4-Hydroxy-1-methyl-proline-ethylester, 4-Hydroxy-1-methyl-proline-isobutylester, 4-Hydroxy-1-methyl-proline-ethylester, 4-Hydroxy-proline ethylester, 4-Hydroxy-proline-isobutylester, cis-4-Hydroxy-L-proline-ethylester, Cis- 4-Hydroxy-L-proline-iso-butylester, 4-Hydroxy-1,1-dimethyl-proline-ethylester-iodide, Hydroxyproline-ethylester, 4-Hydroxy-1,1-dimethyl-proline-iso-butylester-iodide, 4-Hydroxy-1-cyclohexyl-proline-isobutyl-ester, 4-Hydroxy-1-diphenylmethyl-proline-isobutylester-hydrobromide, 4-Hydroxy-1-methyl-proline, 4-Hydroxy-1-alkyl-prolineester amide (alkyl: methy, ethyl, propyl, pentyl, hexyl, heptyl, octyl, and nonyl), 4-Hydroxy-1-diphenylmethyl-proline-isobutyl-ester-hydrobromide. This embodiment encompasses the salts, esters, isomers, racemates, enantiomers or pro-drugs thereof.

In a preferred embodiment of the invention the proline derivative is cis-4-hydroxy-L-proline (CHP). This embodiment encompasses the salts, esters, isomers, racemates, enantiomers or pro-drugs thereof.

In a preferred embodiment of the invention the proline derivative is trans-4-hydroxy-L-proline (THP). This embodiment encompasses the salts, esters, isomers, racemates, enantiomers or pro-drugs thereof.

In a preferred embodiment of the invention the treatment of dementia is a prophylactic treatment.

In a preferred embodiment of the invention the treatment of dementia is carried out in subjects at risk of developing Alzheimer's, neurodegenerative disease, neuromuscular disease or Schizophrenia, or to subjects with down syndrome or other genetic disorders.

The invention therefore provides methods and compositions for use in the prophylaxis, prevention, reduction, attenuation, elimination and or therapy the symptoms of said dementia and Alzeheimer's Disease (AD).

The term "treatment" may relate to prophylaxis, prevention, stabilisation, attenuation, therapy, follow-up and/or aftercare of dementia diseases. Prophylaxis is a preferred embodiment.

The term "proline or a proline derivative" encompasses proline, its derivatives as understood by a skilled person, in particular those described herein, in addition to salts, isomeres, and/or enantiomers thereof, or racemates, or pro-drugs, whereby the preferred proline derivatives include esters, especially methyl, ethyl, isopropyl, butyl or isobutyl esters.

More particularly the invention relates to oral, transmucosal, intravenous, transdermal and intranasal dosage form administrations of cis-4-hydroxy-L-proline (CHP), its salts, isomeres, and/or other derivatives for the prophylaxis, prevention, stabilisation, diagnosis, attenuation, therapy, follow-up and/or aftercare of dementia diseases, Alzheimer's Disease, neurodegenerative and/or neuromuscular disorders The invention involves the surprising and unexpected teaching that a compound, namely non-derivatized CHP whose pharmacological properties have been described in this invention, has an effect on the prophylaxis, prevention, stabilisation, diagnosis, attenuation, therapy, follow-up and/or aftercare of dementia, Alzheimer's diseases, schizophrenia, neurodegenerative diseases and/or parkinson.

Methods and compositions for the prophylaxis, prevention, stabilisation, diagnosis, attenuation, therapy, follow-up and/or aftercare of dementia diseases are described. More specifically, the invention demonstrates that oral administration of the agent proline, cis-4-hydroxy-l-proline, their derivatives, salts, and/or isomeres is effective to prophylaxis, prevent, stabilize the dementia diseases.

In particular embodiments, the invention thus demonstrates a method of treating a human for the prophylaxis, prevention, stabilisation, attenuation, therapy of Alzheimer's disease comprising oral composition of cis-4-hydroxy-l-prolin (CHP) to the human at effective dosage.

The invention further provides the methods for the administration of CHP and/or other compound of the invention for healthy subject and patients as follows:

1. The administration of CHP at an early stage to healthy volunteers/subjects at a young age, subjects with high risk to alzheimer's disease and neurodegenarative disease (Down Syndrome, genetic history) will maintain physiological levels of CHP in the blood/cerebral fluid, and brain tissue and prevent the development of Alzheimer's disease, and other neurodegenerative, and neuromuscular degenerative disorders.

2. The administration of CHP at early stage of Alzheimer's Disease will normalize the CHP levels in the blood/cerebral fluids, and brain tissues at the physiological level and stabilise Alzheimer's disease, other neurodegenerative, and neuromuscular degenerative disorders.

3. CHP administration at advanced stages of Alzheimer's Disease, other neurodegenerative, and neuromuscular degenerative disorders will elevate and normalize the CHP level in blood/cerebral fluids, and brain tissues at the physiological level and stabilize and treat the disease.

In some specific embodiments, the agent proline, cis-4-hydroxy-l-proline (CHP) their derivatives, salts, and/or isomeres is in a pharmaceutically acceptable carrier and administered at a dose of between about 1 mg/kg BW per day to about 400 mg/kg BW/day.

In one embodiment the medical use of the pharmaceutical composition according to the present invention is characterised by administration of the composition at a dose of between about 3 mg/kg BW per day to about 250 mg/kg BW per day.

In other embodiments the invention encompasses a dose of between 0.02 mg/kg BW to 8 mg/kg BW per day, preferably 0.3 mg/kg BW to 4 mg/kg BW per day, preferably 0.3 mg/kg BW to 6 mg/kg BW, more preferably 0.7 mg/kg BW to 10 mg/kg BW per day.

In one embodiment the medical use of the pharmaceutical composition according to the present invention is characterised in that the SR composition is administered at a single dose of between 50 to 800 mg of CHP.

In one embodiment the medical use of the pharmaceutical composition according to the present invention is characterised in that the SR composition is administered at a single dose of between 800 to 1200 mg, preferably about 1000 mg, of CHP.

In a specific embodiment, the invention thus provides a method of treating a human for prophylaxis, prevention, stabilisation, attenuation, therapy of Alzheimer's disease comprising oral transmucosal composition of proline, cis-4-hydroxy-l-prolin (CHP), their derivatives, salts, and/or isomers to the human at effective dosage.

In other aspects of the invention, the method may further comprise administering a pharmaceutical composition comprises transmucosal composition of cis-4-hydroxy-l-prolin (CHP) to a human for prophylaxis, prevention, stabilisation, attenuation, therapy of dementia diseases at effective amounts.

In accordance with the present invention, an anti-dementia/anti-Alzheimer's disease agent are cis-4-hydroxymethyl-l-proline, trans-4-hydroxymethyl-D-proline, trans-4-hydroxymethyl-l-proline, trans-4-methyl-l-proline and cis-3-amino-l-proline or any corresponding salts thereof.

The method comprises administering a pharmaceutical composition essentially comprising of proline, cis-4-hydroxy-l-proline (CHP), their derivatives, salts, and/or isomers or a pharmaceutically acceptable salt thereof in combination with a second agent selected from the group of at least one member of a pharmaceutical antioxidants such as Vitamin E, amino acids such as arginine, neurotransmitters not limited to glutamate, aspartate acetylcholine, catecholamines, 5-HT, GABA and glycine, anticoagulant not limited to acetyl salicylic acid, NMDA receptor antagonists such as ketamine/norketamine, pharmaceutical agents such as carnitine, methyl carnitine, carnitine derivates, galantamine, rivastigmine, donepezil, tacrine and memantine or a pharmaceutically acceptable salt thereof, antiparkinson drugs, anti-AIDS medicaments, antianxiety, and/or anti-schizophrenia wherein the combined amount of said agents is sufficient.

The method of the invention may be achieved through a method that comprises oral administration of a single daily dose of the agent proline, cis-4-hydroxy-I-proline (CHP), their derivatives, salts, and/or isomeres.

Alternatively, multiple doses per day of the agent may be administered. In specific embodiments, a single intranasal administration each day of the agent proline, cis-4-hydroxy-I-prolin (CHP), their derivatives, salts, and/or isomeres is significant for prophylaxis, prevention, stabilisation, attenuation, therapy of dementia diseases/symptoms at effective amounts.

In alternative embodiments, intranasal, intravenous, trans-dermal, rectal, intra-vaginal, depot formulation, administration of proline, cis-4-hydroxy-I-proline (CHP), their derivatives, salts, and/or isomers is significant for prophylaxis, prevention, stabilisation attenuation, therapy of dementia diseases/symptoms at effective amounts are contemplated.

In one alternative embodiment, the invention thus provides a method of treating a human patient for prophylaxis, prevention, stabilisation attenuation, therapy of dementia treatment, comprising intra-nasally administering a composition comprising cis-4-hydroxy-I-proline to the patient at a dosage sufficient to prophylaxis, prevent, stabilize, attenuate, therapy the Alzheimer's syndromes.

In another alternative embodiment, the invention thus provides a method for treating a human patient for prophylaxis, prevention, stabilisation, attenuation, therapy of dementia treatment, comprising transdermally administering a composition comprising cis-4-hydroxy-I-proline (CHP) to the patient at a dosage sufficient to prophylaxis, prevention, stabilisation, attenuation, and/ortherapy the Alzheimer's syndromes.

In another alternative embodiment, the invention thus provides a method for treating a human patient for prophylaxis, prevention, stabilisation, attenuation, therapy of dementia treatment, comprising parenteral administering a composition comprising cis-4-hydroxy-I-proline (CHP) to the patient at a dosage sufficient for prophylaxis, prevention, stabilisation attenuation, therapy of the Alzheimer's syndromes, neurodegenerative and/or neuromuscular degenerative disorders.

In another alternative embodiment, the invention thus provides a method for treating a human patient for prophylaxis, prevention, stabilisation, attenuation, therapy of dementia treatment, comprising rectal administering a composition comprising cis-4-hydroxy-I-proline (CHP) to the patient at a dosage sufficient to prophylaxis, prevent, stabilize for prophylaxis, prevention, stabilisation attenuation, and/or therapy of the Alzheimer's disease syndromes, neurodegenerative and/or neuromuscular degenerative disorders.

In another alternative embodiment, the invention thus provides a method for treating a human patient for prophylaxis, prevention, stabilisation, attenuation, therapy of dementia treatment, comprising locally administering a composition comprising cis-4-hydroxy-I-proline (CHP) to the patient at a dosage sufficient to prophylaxis, prevent, stabilize for prophylaxis, prevention, stabilisation attenuation, and/or therapy of the the Alzheimer's disease (AD) syndromes, neurodegenerative and/or neuromuscular degenerative disorders.

In another alternative embodiment, the invention thus provides a method for treating a human patient for prophylaxis, prevention, stabilisation, attenuation, therapy of dementia treatment, comprising intravaginally administering a composition comprising cis-4-hydroxy-I-proline (CHP) to the patient at a dosage sufficient to prophylaxis, prevent, prophylaxis, prevent, stabilize, attenuate, therapy the Alzheimer's disease (AD) syndromes, neurodegenerative and/or neuromuscular degenerative disorders.

In other embodiments, a pharmaceutical composition containing the agent proline, cis-4-hydroxy-I-proline, their derivatives, salts, enantiomers, and/or isomeres in a pharmaceutically acceptable carrier can be administered in dosage forms a sublingual formulations, orodispersible tablets (ODT), orodispersible films (ODF), orodispersible granules (micro-pellets), fast oral trans-mucosal (FOT), rapid film, capsules dosage form known to those skilled in the art of pharmaceutical formulation. A method for reducing the amount of anti-Alzheimer's disease agents or pharmaceutically acceptable salt thereof required to treat a patient affected with Alzheimer's disease (AD), comprising further administering to a patient being treated with anti-Alzheimer's disease (AD) drug or pharmaceutically acceptable salt thereof an amount of cis-4-hydroxy-1-proline (CHP) or a pharmaceutical acceptable salt thereof.

Also contemplated herein is a kit comprising a carrier for delivering Cis-4-hydroxy-I-proline (CHP) orally, transbuccally, transmucosally, parenterally, locally, transdermally, intranasally, and/or inhallatory containing in close confinement herein one or more components, wherein: a) a first component contains CHP; and b) a second component contains at least one member of a pharmaceutical composition essentially comprising of proline, cis-4-hydroxy-I-proline (CHP), their derivatives, salts, and/or isomeres, or a pharmaceutically acceptable salt thereof in combination with a second agent selected from the group of at least one member of a pharmaceutical antioxidants such as Vitamin E, amino acids such as arginine, neurotransmitters not limited to glutamate, aspartate acetylcholine, catecholamines, 5-HT, GABA and glycine, anticoagulant not limited to acetyl salicylic acid, NMDA receptor antagonists such as ketamine/ketamine, pharmaceutical agents such as carnitine, methyl carnitine, carnitine derivates, galantamine, rivastigmine, donepezil, tacrine and memantine or a pharmaceutically acceptable salt thereof, drugs for the treatment of AIDS, Parkinson, Anxiety, and/or Schizophrenia wherein the combined amount of said agents is sufficient.

In other embodiments, also contemplated herein is a diagnostic kit comprising of device with reagents for the determination of the concentration of cis-4-hydroxy-I-proline (CHP) and/or trans-4-hydroxy-I-proline (THP) in blood and/or urine of the subject.

In one embodiment the medical use of the pharmaceutical composition according to the present invention is characterised by transbuccal administration. The preferred buccal route of drug delivery provides the direct access to the systemic circulation through the jugular vein bypassing the first pass hepatic metabolism leading to high bioavailability. Other advantages such as excellent accessibility, low enzymatic activity, suitability for drugs or excipients that mildly and reversibly damage or irritate the mucosa, painless administration, easy withdrawal, facility to include permeation enhancer/enzyme inhibitor or pH modifier in the formulation, versatility in designing as multidirectional or unidirectional release system for local or systemic action. In one embodiment the medical use of the pharmaceutical composition according to the present invention is characterised by sublingual administration.

In one embodiment the medical use of the pharmaceutical composition according to the present invention is characterised by administration of oral dry powder, preferably to the oral cavity. In a preferred embodiment the pharmaceutical composition for use as a medicament according to the present invention is characterised in that the cis-4-hydroxymethyl-I-proline, trans-4-hydroxymethyl-D-proline, trans-4-hydroxymethyl-I-proline, trans-4-methyl-I-proline and cis-3-Amino-I-proline or any corresponding salts.

In a preferred embodiment the pharmaceutical composition for use as a medicament according to the present invention is characterised in that the salt of cis-4-hydroxy-L-proline (CHP), cis-4-hydroxymethyl-I-proline, trans-4-hydroxymethyl-D-proline, trans-4-hydroxymethyl-I-proline, trans-4-methyl-I-proline and cis-3-Amino-I-proline or any corresponding salts.

Salts relate preferably to an organic acid, preferably selected from an acetic, trifluoroacetic, propionic, succinic, glycolic, stearic, lactic, malic, tartaric, citric, ascorbic, or amino acid salt.

In further embodiments of the invention the pharmaceutical composition for use as a medicament according to the present invention is characterised in that the CHP amino acid salt is arginate, asparginate, or glutamate.

In further embodiments of the present invention the dementia to be treated include dementia caused by Alzheimer's Disease (AD), AIDS, Parkinson's disease, Lewy body disease, Pick's disease, Huntington's disease, Creutzfeldt-Jakob disease, brain tumor, hydrocephalus head trauma, multiple sclerosis, prolonged abuse of alcohol or other drugs, vitamin deficiency: thiamin, niacin, or B12 hypothyroidis, hypercalcemia.

The pharmaceutical composition for use as a medicament according to the present invention is characterised in that the composition is administered at a dosage sufficient to prevent (prophylaxis), reduce, attenuate, eliminate and/or therapeutically treat the symptoms of said dementia.

In one embodiment the medical use of the pharmaceutical composition according to the present invention is characterised by administration of a single dose of said composition.

In one embodiment the medical use of the pharmaceutical composition according to the present invention is characterised by administration of a multiple dose of said composition.

In one embodiment the medical use of the pharmaceutical composition according to the present invention is characterised by administration of the composition at a dose of between about 5 mg/kg BW per day to about 300 mg/kg BW per day.

In other embodiments the invention encompasses a dose of between 0.05 mg/kg BW to 10 mg/kg BW per day, preferably 0.1 mg/kg BW to 5 mg/kg BW per day, preferably 0.5 mg/kg BW to 4 mg/kg BW, more preferably 0.9 mg/kg BW to 3 mg/kg BW per day.

In one embodiment the medical use of the pharmaceutical composition according to the present invention is characterised in that the SR composition is administered at a single dose of between 100 to 500 mg of CHP.

In one embodiment the medical use of the pharmaceutical composition according to the present invention is characterised in that the SR composition is administered at a single dose of between 200 to 800 mg, preferably about 600 mg, of CHP.

In a further aspect of the invention the medical use of the pharmaceutical composition according to the present invention is characterised in that the composition is administered in combination with opioid therapy in cancer patients with pain.

In one embodiment the medical use of the pharmaceutical composition according to the present invention is characterised by administration of a pharmaceutically effective dose of a second agent, preferably selected from the group of at least one member of a pharmaceutical antioxidants such as Vitamin E, amino acids such as arginine, neurotransmitters not limited to glutamate, aspartate acetylcholine, catecholamines, 5-HT, GABA and glycine, anticoagulant not limited to acetyl salicylic acid, NMDA receptor antagonists such as ketamine/ketamine, pharmaceutical agents such as carnitine, methyl carnitine, carnitine derivates, galantamine, rivastigmine, donepezil, tacrine and memantine or a pharmaceutically acceptable salt thereof, wherein the combined amount of said agents is sufficient.

The invention therefore relates to a pharmaceutical composition for use as a medicament according to the present invention, comprising CHP, salts and/or derivative thereof, and one or more pharmaceutically acceptable oral transmucosal carrier substances.

In a preferred embodiment the pharmaceutical composition for use as a medicament according to the present invention, comprises CHP to treat the subject of CHP deficiency.

In a preferred embodiment the pharmaceutical composition for use as a medicament according to the present invention, comprises CHP, isomers, salts and/or derivative thereof, and one or more pharmaceutically acceptable oral transbuccal carrier substances.

The buccal systems preferably exhibit muco-adhesive properties upon contact with saliva, resulting in secure adhesion to the application site. The platform can be designed to either dissolve or to remain in its origin form and lose adhesion after a certain amount of time. The second option is intended to be removed from the oral cavity upon loss of adhesion.

In a preferred embodiment the pharmaceutical composition for use as a medicament according to the present invention, comprises CHP, salts and/or derivative thereof, and one or more pharmaceutically acceptable oral sublingual carrier substances.

In a preferred embodiment the pharmaceutical composition for use as a medicament according to the present invention, comprises CHP, salts and/or derivative thereof, and one or more pharmaceutically acceptable carrier substances for an oral dry powder.

The invention also encompasses a method of treating a human patient for dementia and/or Alzheimer's Disease (AD) comprising intranasal, transdermal, spray inhalation, rectal, intravenous, topical and/or local administration of a composition comprising CHP, its salt, and/or derivative to said patient at a dosage sufficient to prophylaxis, prevention, reduce, attenuate, eliminate and/or therapy the symptoms of said dementia and AD.

The invention therefore encompasses a device for patient self-administration of CHP, its isomeres, enantiomers, salt, and/or derivative comprising a nasal spray or powder inhaler containing an aerosol spray formulation of CHP, its salt, and/or derivative and a pharmaceutically acceptable dispersant, wherein the device is metered to disperse an amount of the aerosol formulation by forming a spray that contains a dose of CHP effective to reduce or eliminate the symptoms of dementia.

The invention therefore encompasses a kit for administration of a medicament comprising in close confinement at least a) CHP, salts and/or derivatives thereof and b) a device for self-administration of an intranasal formulation, and optionally c) a second agent selected the group of at least one member of a pharmaceutical antioxidants such as Vitamin E, amino acids such as arginine, neurotransmitters not limited to glutamate, aspartate acetylcholine, catecholamines, 5-HT, GABA and glycine, anticoagulant not limited to acetyl salicylic acid, NMDA receptor antagonists such as ketamine/ketamine, pharmaceutical agents such as carnitine, methyl carnitine, carnitine derivates, galantamine, rivastigmine, donepezil, tacrine and memantine or a pharmaceutically acceptable salt thereof, wherein the combined amount of said agents is sufficient.

The invention encompasses a kit for administration of a medicament comprising in close confinement at least a) CHP, salts and/or derivatives thereof and b) a device for self-administration of a transdermal formulation such as a transdermal patch, and optionally c) a second agent selected from the group. The invention encompasses a pharmaceutical composition comprising S-Ketamine, salts and/or derivatives thereof for use as a neuro-protective medicament in subjects with brain and/or spinal cord injuries, characterised in that said treatment comprises oral transmucosal administration of the group of at least one member of a pharmaceutical antioxidants such as Vitamin E, amino acids such as arginine, neurotransmitters not limited to glutamate, aspartate acetylcholine, catecholamines, 5-HT, GABA and glycine, anticoagulant not limited to acetyl salicylic acid, NMDA receptor antagonists such as ketamine/ketamine, pharmaceutical agents such as carnitine, methyl carnitine, carnitine derivates, galantamine, rivastigmine, donepezil, tacrine and memantine or a pharmaceutically acceptable salt thereof, wherein the combined amount of said agents is sufficient.

The invention encompasses a pharmaceutical composition comprising CHP, salts and/or derivatives thereof for use as a medicament in treatment of depression and/or CNS-disorders, characterised in that said treatment comprises oral transmucosal administration of said pharmaceutical composition to a subject in need of said treatment.

The invention also encompasses a method of treating a human patient for dementia and Alzheimer's Disease (AD) comprising orally administering a composition comprising trans-4-hydroxy-4-I-proline (THP), cis-4-hydroxymethyl-I-proline, trans-4-hydroxymethyl-D-proline, trans-4-hydroxymethyl-I-proline, trans-4-methyl-I-proline and cis-3-Amino-I-proline), to said patient at a dosage sufficient to treat the symptoms of said dementia and/or Alzheimer's Disease (AD).

Administration and Dosage

Pharmaceutically acceptable organic salts of CHP include salts prepared from organic acids such as acetic, trifluoroacetic, propionic, succinic, glycolic, stearic, lactic, malic, tartaric, citric, ascorbic, and amino acid salts such as arginate, asparginate, and glutamate, and combinations comprising one or more of the foregoing salts.

The compounds of the invention are defined to include pharmaceutically acceptable derivatives or prodrugs thereof. A pharmaceutically acceptable derivative or prodrug means any pharmaceutically acceptable salt, ester, salt of an ester, or other derivative of a compound of this invention, which upon administration to a recipient is capable of providing or provides (directly or indirectly) a compound of this invention. The pharmaceutical compositions of this invention may be administered orally, parenterally, by inhalation spray, topically, rectally, nasally, buccally, vaginally or via an implanted reservoir.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of sterile injectable preparation.

The pharmaceutical compositions may be orally administered in any orally acceptable dosage form including but not limited to, oral transmucosal carriers, buccal delivery compositions, sublingual formulations, Orodispersible Tablets (ODT), Orodispersible Films (ODF), Orodispersible Granules (Micro-Pellets), Fast Oral Transmucosal (FOT), capsules, tablets, an aqueous suspensions and solutions.

The pharmaceutical compositions may also be administered in the form of suppositories for rectal administration.

Topical administration of the pharmaceutical compositions of this invention is especially useful when the desired treatment involves areas or organs readily accessible by topical application carriers for topical administration of the compounds of this invention include, but are not limited to, mineral oil, and olive oil.

The pharmaceutical compositions may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions of the present invention may conveniently be presented in unit dosage form and may be prepared by any methods well known in the art of pharmacy. The amount of active ingredient that can be combined with a carrier material to produce a single dosage form will vary depending upon the host being treated, the particular mode of administration. The amount of active ingredient that can be combined with a carrier material to produce a therapeutic effect.

Generally, out of one hundred percent, this amount will range in some embodiments from about 1 percent to about ninety-nine percent of active ingredient, in some embodiments from about 5 percent to about 90 percent, and in some embodiments from about 10 percent to about 30 percent.

The selected dosage level will depend upon a variety of factors including the activity of the particular compound of the present invention employed, or the ester, salt or amide thereof, the route of administration, the time of administration, the rate of excretion of the particular compound being employed, the duration of treatment, other drugs, compounds and/or materials used in combination with the particular compound employed, the age, gender, weight, condition, general health and prior medical history of the patient being treated, and like factors well known in the medical art.

In general, a suitable daily dose of a compound of the invention will be that amount of the compound that is the lowest dose effective to produce a prophylactic and/or therapeutic effect. Such an effective dose will be generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In some embodiments, the active compound will be administered once daily.

In another aspect of the invention, the compounds of the invention are administered alone or co-administered with another therapeutic agent. As used herein, the phrase "co-administration" refers to any form of administration of two or more different therapeutic compounds such that the desired effect is obtained. The different therapeutic compounds may be administered either in the same formulation or in separate formulation, either concomitantly or sequentially. Thus, an individual who receives such treatment may benefit from a combined effect of different therapeutic compounds. Co-administration includes simultaneous or sequential administration of two or more compounds which may have synergistic, additive and/or different therapeutic effects.

In one embodiment the invention comprises a method for the diagnosis of dementia comprising measuring the levels of proline, CHP, THP or other compounds of the invention in a sample obtained from a subject.

In one embodiment the method for the diagnosis of dementia of the invention comprises or consists of the following steps:

a) Providing or obtaining a sample, preferably a bodily fluid, such as a urine, blood, serum or plasma sample, from a subject exhibiting one or more symptoms of dementia, or a neurodegenerative disease, or other condition described herein, b) Bringing said sample into contact with a reagent that can detect a molecule of proline, CHP, THP or other compounds of the invention, such as an antibody, or other binding or detecting reagent, c) Detecting and/or evaluating the presence, amount of, or absence of proline, CHP, THP or other compounds of the invention in said sample, wherein d) The amount of proline, CHP, THP or other compounds of the invention detected in the sample is indicative of a particular state of (presence or absence of) dementia.

The present invention also encompasses a corresponding treatment of dementia as step e) in a subject, preferably human subject, for example after the outcome of the diagnostic method has been obtained from steps a) to d. Possible treatments are known to a person skilled in the art. For example, dementia may be treated with the means of the invention and/or other agents as described herein.

The present invention further relates to a method for the treatment of dementia in a human subject, comprising:
having a sample of biological fluid obtained from the subject,
having an assay conducted on the sample, said assay comprising detecting proline, CHP, THP or other compounds of the invention in a sample obtained from a subject,
Detecting and evaluating the presence, amount of or absence of proline, CHP, THP or other compounds of the invention, and
treating the subject for dementia using one or more means for treatment, preferably those of the present invention.

DETAILED DESCRIPTION OF THE INVENTION

Definition of Terms

It should be understood that the purposes of the present invention, the following terms have the following meanings:

The term "dementia" is defined for the purpose of the present invention as loss of mental ability severe enough to interfere with normal activities of daily living, lasting more than six months, not present since birth, and not associated with a loss or alteration of consciousness. Dementia is a group of symptoms caused by gradual death of brain cells. The loss of cognitive abilities that occurs with dementia leads to impairments in memory, reasoning, planning, and behaviour. While the overwhelming number of people with dementia are elderly, dementia is not an inevitable part of aging; instead, dementia is caused by specific brain diseases. Alzheimer's disease (AD) is the most common cause, followed by vascular or multi-infarct dementia.

The term "causes of dementia" are defined for the purpose of the present invention as a disease caused by degeneration in the cerebral cortex, the part of the brain responsible for thoughts, memories, actions, and personality. Death of brain cells in this region leads to the cognitive impairment that characterizes dementia.

The term "Neurofibrillary tangles" is defined for the purposes of the present invention as Abnormal structures, composed of twisted masses of protein fibers within nerve cells, found in the brains of people with Alzheimer's disease.

The term "Neurotransmitter" is defined for the purposes of the present invention as a group of chemicals secreted by a nerve cell (neuron) to carry a chemical message to another nerve cell, often as a way of transmitting a nerve impulse. Examples of neurotransmitters include acetylcholine, dopamine, serotonin, and norepinephrine.

The term "Senile plaques" is defined for the purposes of the present invention as abnormal structures, composed of parts of nerve cells surrounding protein deposits, found in the brains of people with Alzheimer's disease.

The terms "treating dementia," "therapy," and the like refer generally to any improvement in the mammal having the dementia, wherein the improvement can be ascribed to treatment with the compounds of the present invention. The improvement can be either subjective or objective. For example, if the mammal is human, the patient may note improved vigour or vitality or decreased memory loss as subjective symptoms of improvement or response to therapy. Alternatively, the clinician may notice an improvement based on neurological and/or physical exam, laboratory parameters such as proline, CHP, THP, in blood, in biological materials and/or biomarkers or radiographic findings.

Some laboratory obtained results which the clinician may observe to check for any response to therapy include normalization of tests such as biomarkers and/or various enzyme levels. Alternatively, other tests can be used to evaluate objective improvement such as sonograms, nuclear magnetic resonance testing and positron emissions testing.

"Prophylaxis of dementia" can be evaluated by any accepted method of measuring whether symptoms has been slowed or diminished. This includes direct observation and indirect evaluation such as subjective symptoms or objective signs as discussed above. In addition prophylaxis of dementia can also be evaluated by the treatment of the deficiency of CHP and/or THP and/or the compound of this invention in the biological materials of the subject The term "Neurodegeneration" is defined for the purposes of the present invention as umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death Neurodegeneration can be found in many different levels of neuronal circuitry ranging from molecular to systemic.

There are links between neurodegenerative disorders:

Genetics: Many neurodegenerative diseases are caused by genetic mutations, most of which are located in completely unrelated genes. In many of the different diseases, the mutated gene has a common feature—a repeat of the CAG nucleotide triplet. CAG encodes for the amino acid glutamine. A repeat of CAG results in a polyglutamine (polyQ) tract. Diseases showing this are known as polyglutamine diseases.

Protein misfolding: Several neurodegenerative diseases are classified as proteopathies as they are associated with the aggregation of misfolded proteins.

Alpha-synuclein: Can aggregate to form insoluble fibrils in pathological conditions characterized by Lewy bodies, such as Parkinson's disease, dementia with Lewy bodies, and multiple system atrophy. Alpha-synuclein is the primary structural component of Lewy body fibrils. In addition, an alpha-synuclein fragment, known as the non-Abeta component (NAC), is found in amyloid plaques in Alzheimer's disease.

Tau: Hyperphosphorylated tau protein is the main component of neurofibrillary in Alzheimer's disease.

Beta amyloid: The major component of senile plaques in Alzheimer's disease. Parkinson's disease and Huntington's disease are both late-onset and associated with the accumulation of intracellular toxic proteins. Diseases caused by the aggregation of proteins are known as proteinopathies, and they are primarily caused by aggregates in the following structures:

Cytosol, e.g. Parkinson's & Huntington's.

Nucleus, e.g. Spinocerebellar ataxia type 1 (SCA1).

Endoplasmic reticulum (ER), (as seen with neuroserpin mutations that cause familial encephalopathy with neuroserpin inclusion bodies).

Extracellularly excreted proteins, amyloid-β in Alzheimer's disease.

The term "Membrane damage" is defined for the purposes of the present invention as damage to the membranes of organelles by monomeric or oligomeric proteins, which could also contribute to these diseases. Alpha-synuclein can damage membranes by inducing membrane curvature, and extensive tubulation and vesiculation were observed when these proteins were incubated with artificial phospholipid vesicles.

The term "cognition" is defined in science for the purposes of the present invention as a mental processing that includes the attention of working memory of comprehending and producing language, calculating, reasoning, problem solving and decision making.

The term "cerebrum" is defined for the purposes of the present invention as the tissue comprises a large portion of the brain. It lies in front or on top of the brainstem and in humans is the largest and best-developed of the five major divisions of the brain. The cerebrum is the newest structure in the phylogenetic sense, with mammals having the largest and best-developed among all species. In larger mammals, the cerebral cortex is folded into many gyri (ridges) and sulci (furrows), which has allowed the cortex to expand in surface area without taking up much greater volume. In humans, the cerebrum surrounds older parts of the brain. Limbic, olfactory, and motor systems project fibers from the cerebrum to the brainstem and spinal cord. Cognitive and volitive systems project fibers from the cerebrum to the thalamus and to specific regions of the midbrain. The neural networks of the cerebrum facilitate complex behaviors such as social interactions, thought, judgement, learning, working memory, and in humans, speech and language.

The term cerebellum ("little brain") for the purposes of the invention as a structure that is located at the back of the brain, underlying the occipital and temporal lobes of the cerebral cortex. Although the cerebellum accounts for approximately 10% of the brain's volume, it contains over 50% of the total number of neurons in the brain. Historically, the cerebellum has been considered a motor structure, because cerebellar damage leads to impairments in motor control and posture and because the majority of the cerebellum's outputs are to parts of the motor system. Motor commands are not initiated in the cerebellum; rather, the cerebellum modifies the motor commands of the descending pathways to make movements more adaptive and accurate.

The cerebellum is involved in the following functions: maintenance of balance and posture, coordination of voluntary movements, motor learning, cognitive functions. The term "brainstem" is defined for the purposes of the present invention as, area at the base of the brain that lies between the deep structures of the cerebral hemispheres and the cervical spinal cord. It is divided into three sections: midbrain (mesencephalon), pons (metencephalon), and medulla oblongata (myelencephalon). The brainstem houses many of the control centres for vital body functions, such as swallowing, breathing, and vasomotor control.

The term "limbic system (or paleomammalian brain)" is defined for the purposes of the present invention as a complex set of brain structures that lies on both sides of the thalamus, right under the cerebrum. It is not a separate system, but a collection of structures from the telencephalon, diencephalon, and mesencephalon. The limbic system includes the hippocampus, amygdala, anterior thalamic nuclei, septum, habenula, limbic cortex and fornix. It supports a variety of functions, including emotion, behavior, motivation, long-term memory and olfaction. It appears to be primarily responsible for our emotional life, and has a great deal to do with the formation of memories.

The term "nerve cells" is defined for the purposes of the present invention as cells that originate, process, transmit, and receive nerve impulses. They are connected to other neurons or to cells in muscles, organs, or glands. Nerve impulses travel electrically along the neuron and are transmitted by chemical messengers (neurotransmitters) to the next neuron across a tiny gap, called a synapse, between the neuron and the adjacent cell, which is known as the target cell. In addition to neurons, the nervous system contains large numbers of other types of cell, called neuroglia, which protect, nourish, and support neurons. In addition to features common to all cells, such as a nucleus and organelles such as mitochondria, endoplasmic reticulum and Golgi apparatus. neurons have specialized projections, known as nerve fibres (axons), that carry nerve signals. Neurons in the brain form densely packed clusters. Neurons in the spinal cord and around the body form long communication tracts.

The term "neuromuscular disease" is defined for the purposes of the present invention as a disorder that affects the peripheral nervous system. The peripheral nervous system includes muscles, the nerve-muscle (neuromuscular) junction, peripheral nerves in the limbs, and the motor-nerve cells in the spinal cord. Other spinal cord or brain diseases are not considered "neuromuscular" diseases. Patients with neuromuscular diseases can have weakness, loss of muscle bulk, muscle twitching, cramping, numbness, tingling, and a host of other symptoms. Problems with the nerve-muscle junction can also cause droopy eyelids, double vision, and weakness that worsen with activity. Some neuromuscular disorders can also cause difficulty with swallowing and sometimes with breathing.

The terms "Health-related quality of life" (HRQL)/Quality of Life is defined for the purposes of the present invention as: an individual's satisfaction or happiness with domains of life insofar as they affect or are affected by "health" as defined above. HRQL can be distinguished from quality of life as we defined it earlier in that it concerns itself primarily with those factors that fall under the purview of health care providers and health care systems. Generally speaking, then, assessment of HRQL represents an attempt to determine how variables within the dimension of health (e.g., a disease or its treatment) relate to particular dimensions of life that have been determined to be important to people in general (generic HRQL) or to people who have a specific disease (condition-specific HRQL). Most conceptualizations of HRQL emphasize the effects of disease on physical, social/role, psychological/emotional, and cognitive functioning. Symptoms, health perceptions, and overall quality of life are often included in the concept domain of HRQL.

The term "Loose connective tissue" is defined for the purposes of the present invention as primarily located beneath epithelial membranes and glandular epithelium, binding these epithelia to other tissues, contributing to the formation of organs. Loose connective tissue (LCT) consists of an abundance of amorphous ground substance, a loose, multidirectional weave of extracellular fibers, an abundance of different types of fixed and wandering connective tissue cells. This type of connective tissue proper, with the help of its extracellular fibers, tightly binds epithelia to underlying tissue and physically supports the blood vessels and nerves that supply the subepithelial area. However, because loose connective tissue is primarily ground substance and cells, its overwhelming functions are related to these components: loose connective tissue serves as the principal site of rapid fluid and gas exchange between blood and local tissue and the medium in which the fluid infiltration and cell migration of the inflammatory response takes place.

The term "reticular connective tissue" is defined for the purposes of the present invention as a type of tissue found in the body that is supported with a branching framework of collagen fibers known as reticular fibers. These fibers are present in many types of connective tissue and are particularly heavily concentrated in reticular connective tissue. Some examples of structures in the body that include this type of connective tissue include the liver, spleen, and lymph nodes. In reticular connective tissue, cells that secrete type III collagen work together to create a stable lattice of fibers. The fibers provide support and stability to other types of cells. While the lattice itself is fixed in place through the connections between the fibers and the cells, other types of cells along with fluids can move freely across and through the lattice. This allows for free exchanges between cells, while still providing a reinforcing framework that will support an organ or lymph node.

The term "dense connective tissue" is defined for the purposes of the present invention as connective tissues classified into two categories based on the arrangement of the fibrous elements of the extracellular matrix: Dense irregular connective tissue in which collagen and elastic fibers are found running in all different directions and planes. Within the matrix the fibroblast is the major cell type and is responsible for the repair and maintenance of the matrix (Dense Irregular CT). Dense regular connective tissue in which the extracellular fibers all run in the same direction and plane. It is further classified relative to function and by the type of fibers present. If the matrix consist mainly of collagen, it provides great tensile strength and can withstand tremendous pull in the direction that the fibers run without stretching. This type of dense regular connective tissue is found in the tendon, which connects muscles to bones or cartilage (Tendon 1). Between bundles of eosinophilic collagen, fibroblasts are readily observed (Tendon 2). Ligaments connect bones to bones in the movable joints. Since bony tissue has no flexibility, the connective tissue must provide it and therefore elastic fibers are now found in the matrix; collagen is also present to provide tensile strength (Ligament 1). Histologically, ligaments consist of bundles of eosinophilic collagen, fibroblast, and yellowish elastin fibers (often with a "ribbon candy" morphology) (Ligament 2).

The term "mitochondrial dysfunction" is defined for the purposes of the present invention as the most common form of cell death in neurodegeneration is through the intrinsic mitochondrial apoptotic pathway. There is strong evidence that mitochondrial dysfunction and oxidative stress play a causal role in neurodegenerative disease pathogenesis, including in four of the more well known diseases Alzheimer's, Parkinson's, Huntington's, and amyotrophic lateral sclerosis.

The term "axonal transport" is defined for the purposes of the present invention as axonal swelling and spheroids, which have been observed in many different neurodegenerative diseases. This suggests that defective axons are not only present in diseased neurons, but also that they may cause certain pathological insult due to accumulation of organelles. Axonal transport can be disrupted by a variety of mechanisms including damage to: kinesin and cytoplasmic dynein, microtubules, cargoes, and mitochondria. When axonal transport is severely disrupted a degenerative pathway known as Wallerian-like degeneration is often triggered. The term "programmed cell death (PCD)" is defined for the purposes of the present invention as the death of a cell in any form, mediated by an intracellular program. There are, however, situations in which these mediated pathways are artificially stimulated due to injury or disease.

The term "Alzheimer's disease (AD)", is defined for the purposes of the present invention as the most common form of dementia. There is no cure for the disease, which worsens as progresses and eventually leads to death. The term "neuroprotection" is defined for the purposes of the present invention as a widely explored treatment option for many central nervous system (CNS) disorders including neurodegenerative diseases, stroke, traumatic brain injury, and spinal cord injury. Neuroprotection aims to prevent or slow disease progression and secondary injuries by halting or at least slowing the loss of neurons. Despite differences in symptoms or injuries associated with CNS disorders, many of the mechanisms behind neurodegeneration are the same. Common mechanisms include increased levels in oxidative stress, mitochondrial dysfunction, excitotoxicity, inflammatory changes, iron accumulation, and protein aggregation. Of these mechanisms, neuroprotective treatments often target oxidative stress and excitotoxicity—both of which are highly associated with CNS disorders. Not only can oxidative stress and excitotoxicity trigger neuron cell death but when combine they have synergistic effects that cause even more degradation than on their own. Thus limiting excitotoxicity and oxidative stress is a very important aspect of neuroprotection. Common neuroprotective treatments are glutamate antagonists and antioxidants, which aim to limit excitotoxicity and oxidative stress respectively.

The term "antipsychotic Drugs" is defined for the purposes of the present invention as a class of medicines used to treat psychosis and other mental and emotional conditions.

The term "fibrosis" is defined for the purposes of the present invention as formation of fibrous tissue. The following types of fibrosis are known:

Congenital hepatic fibrosis a developmental disorder of the liver marked by formation of irregular broad bands of fibrous tissue containing multiple cysts formed by disordered terminal bile ducts, resulting in vascular constriction and portal hypertension.

Cystic fibrosis, of the pancreas a generalized hereditary disorder of infants, children, and young adults, with widespread dysfunction of exocrine glands, signs of chronic pulmonary disease, obstruction of pancreatic ducts by eosinophilic concretions and consequent pancreatic enzyme deficiency, and other symptoms.

Endomyocardial fibrosis idiopathic myocardiopathy seen endemically in parts of Africa and less often in other areas, characterized by cardiomegaly, thickening of the endocardium with dense, white fibrous tissue that often extends to involve the inner third or half of the myocardium, and congestive heart failure.

Idiopathic pulmonary fibrosis chronic inflammation and progressive fibrosis of the pulmonary alveolar walls, with progressive dyspnea and potentially fatal lack of oxygen or right heart failure. The acute form is called Hamman-Rich syndrome.

Mediastinal fibrosis is fibrous mediastinitis; development of white, hard fibrous tissue in the upper portion of the mediastinum, sometimes obstructing the air passages and large blood vessels.

Nodular Subepidermal Fibrosis

1. Benign fibrous histiocytoma as a type of benign fibrous histiocytoma marked by subepidermal formation of fibrous nodules as a result of productive inflammation.

2. Pleural fibrosis as fibrosis of the visceral pleura so that part or all of a lung becomes covered with a thick layer of nonexpansible fibrous tissue; fibrothorax is a more extensive form. and leads to cirrhosis.

The term "EMT" is defined for the purposes of the present invention as a cellular process that transforms normal functioning cells into myofibroblast cells, which produce components of scar tissue. In the normal process of tissue repair, EMT promotes healing of tissues and is shut down once healing has occurred. However, recurring insult and injury, such as that which occurs in chronic disease, results in an imbalance of growth factors (elevated levels of CTGF) and dysfunctional signaling, leading to persistent EMT. Research shows that CTGF drives EMT occurring in multiple types of tissues including kidney, lung, and liver.

The term "CTGF, also known as CCN2 or connective tissue growth factor" is defined for the purposes of the present invention as a matricellular protein of the CCN family of extracellular matrix-associated heparin-binding proteins (see also CCN intercellular signaling protein). CTGF has important roles in many biological processes, including cell adhesion, migration, proliferation, angiogenesis, skeletal development, and tissue wound repair, and is critically involved in fibrotic disease and several forms of cancers. CTGF is associated with wound healing and virtually all fibrotic pathology. It is thought that CTGF can cooperate with TGF-β to induce sustained fibrosis, and to exacerbate extracellular matrix production in association other fibrosis-inducing conditions. Overexpression of CTGF in fibroblasts promotes fibrosis in the dermis, kidney, and lung, and deletion of CTGF in fibroblasts and smooth muscle cells greatly reduces bleomycin-induced skin fibrosis. In addition to fibrosis, aberrant CTGF expression is also associated with many types of malignancies, diabetic nephropathy and retinopathy, arthritis, and cardiovascular diseases. Several clinical trials are now ongoing that investigate the therapeutic value of targeting CTGF in fibrosis, diabetic nephropathy, and pancreatic cancer.

The term "Genetic Material" is defined for the purposes of the present invention as the genetic material of a cell or an organism refers to those materials found in the nucleus, mitochondria and cytoplasm, which play a fundamental role in determining the structure and nature of cell substances, and capable of self-propagating and variation. The genetic material of a cell can be a gene, a part of a gene, a group of genes, a DNA molecule, a fragment of DNA, a group of DNA molecules, or the entire genome of an organism.

The term "Glutathione S-transferases (GSTs)" is defined for the purpose of the present invention, as previously known as ligandins, comprise a family of eukaryotic and prokaryotic phase II metabolic isozymes best known for their ability to catalyze the conjugation of the reduced form of glutathione (GSH) to xenobiotic substrates for the purpose of detoxification.

Clinical Significance of GST

In addition to their roles in cancer development and chemotherapeutic drug resistance, GSTs are implicated in a variety of diseases by virtue of their involvement with GSH.

The term "Proline" is defined for the purpose of the present invention as a compound (abbreviated as Pro or P) is an α-amino acid, one of the twenty DNA-encoded amino acids. It is not an essential amino acid, which means that the human body can synthesize it.

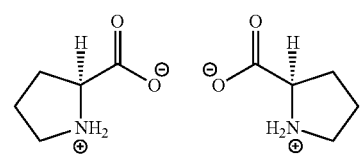 [SMILES: O=C([O-])[C@@H]1CCC[NH2+]1 ; O=C([O-])[C@H]1CCC[NH2+]1]

Zwitterionic structure of both proline enantiomers: (S)-proline (left) and (R)-proline.

The term "cis-4-hydroxy-I-proline" or "CHP" is defined for the purposes of the present invention as the structural formula: C5H9 NO3, and a molecular weight: 131.13 Dalton, preferably present as a crystalline white powder. It is the Cis-isomer of 4-hydroxy-I-proline.

The "trans-4-hydroxy-I-proline" or "THP" is an uncommon amino acid. THP differs from proline by the Presence of a hydroxyl (OH) group attached to the C (gamma) atom.

THP is produced by hydroxylation of the amino acid proline. It is not directly coded by DNA, however, and is hydroxylated after protein synthesis. THP is a major component of the protein collagen. Hydroxyproline and proline play key roles for collagen stability. They permit the sharp twisting of the collagen helix. It helps provide stability to the triple-helical structure of collagen by forming hydrogen bonds. Hydroxyproline is found in few proteins other than collagen. The only other mammalian protein which includes hydroxyproline is elastin. Proline hydroxylation requires ascorbic acid.

Structural differences between cis and trans 4-hydroxy-L-proline:

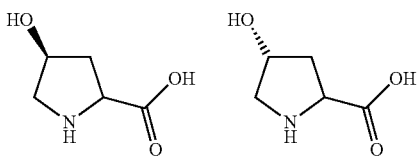

On the left is shown cis-4-OH-L-proline, on the right trans-4-OH-L-proline.

The term "animal" refers to an organism with a closed circulatory system of blood vessels and includes birds, mammals and crocodiles. The term "animal" used here also includes human subjects.

An "immunologically effective amount" is the quantity of a compound, composition or carrier system of the present invention which is effective in yielding the desired immunologic response.

Additional "carriers" may be used in the "carrier system" of the present invention, and include any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the carrier systems.

The term "biomarker" is defined for the purposes of the present invention as tests that can be used to follow body processes and diseases in humans and animals. They can be used to predict how a patient will respond to a medicine or whether they have, or are likely to develop, a certain disease. It is a characteristic that is objectively measured and evaluated as an indicator of normal biologic processes, pathogenic processes, or pharmacologic responses to a therapeutic intervention. It is surprisingly and unexpected that according to the present invention and the examples in this invention the levels of CHP in blood and/or cerebrospinal fluid CSF predict the likelihood that a patient with mild memory problems will go on to develop dementia due to Alzheimer's disease.

The term "multi-target therapeutic agent" is defined for the purposes of the present invention as component impacts separate targets to create a combination effect. The targets can reside in the same or separate pathways within individual cell, or in separate tissues.

The phrase "pharmaceutically-acceptable" refers to molecular entities and compositions that do not produce an allergic or similar untoward reaction when administered to a human. The term "pharmaceutically acceptable salt" refers to those salts of compounds which retain the biological effectiveness and properties of the free bases and which are obtained by reaction with inorganic acids such as hydrochloric acid, hydrobromic acid, sulphuric acid, nitric acid, phosphoric acid, methanesulphonic acid, ethane sulphonic acid, toluene sulphonic acid, salicylic acid and the like. A "pharmaceutical agent" is to be understood as any medicament, intended for use in the diagnosis, cure, mitigation, treatment, or prevention of disease in humans or animals.

An "immunologically active substance" is to be understood as any substance that leads to an immune response in a human or animal patient.

The term "disease" is defined for the purposes of the present invention as a pathological condition of a part, organ, or system of an organism resulting from various causes, such as infection, genetic defect, or environmental stress, and characterized by an identifiable group of signs or symptoms. The term "prophylaxis" is defined for the purposes of the present invention as a measure taken to maintain health and prevent the spread of disease.

The term "Therapeutic Drug Monitoring TDM" is defined for the purposes of the present invention as the clinical laboratory measurement of a chemical and/or biological parameter that, with appropriate medical interpretation, which will directly influence drug prescribing procedures. Otherwise, TDM refers to the individualization of drug dosage by maintaining plasma or blood drug concentration within a targeted therapeutic range or window.

The term "Prophylactic Drug Monitoring PDM" is defined for the purposes of the present invention as the clinical laboratory measurement of a chemical and/or biological parameter that, with appropriate medical interpretation, which will directly influence drug prescribing procedures as measure taken to maintain health and prevent the disease and/or its spread. Otherwise. PDM refers to the individualization of drug dosage by maintaining plasma or blood drug concentration within a targeted prophylactic range or window.

The term "patient" is defined for the purposes of the present invention that includes both humans and other animals, particularly mammals, and other organisms. Thus the methods are applicable to both human therapy, vaccinations, and veterinary applications. In the preferred embodiment the patient is a mammal, the most preferred being a human.

The terms "treating cancer," "therapy," and the like refer generally to any improvement in the mammal having the cancer wherein the improvement can be ascribed to treatment with the compounds of the present invention. The improvement can be either subjective or objective. For example, if the mammal is human, the patient may note improved vigour or vitality or decreased pain as subjective symptoms of improvement or response to therapy. Alternatively, the clinician may notice a decrease in tumour size or tumour burden based on physical exam, laboratory parameters, tumour markers or radiographic findings.

The term "administered" is defined for the purposes of the present invention as the administration of a therapeutically effective dose of the candidate agents of the invention to a cell either in cell culture or in a patient. Accordingly the composition of the invention is administered to cells, tissues of subjects.

The term "therapeutically effective dose" is defined for the purposes of the present invention as a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art.

The term "replacement therapy" is defined for the purposes of the present invention as therapy designed to compensate for a lack or deficiency of CHP and/or THP arising from certain dysfunction, or from losses. Replacement will entail administration of CHP and/or THP and/or any of the compounds of the invention.

The term "cells" is defined for the purposes of the invention as the smallest structural unit of an organism that is capable of independent functioning considering of one or more nuclei, cytoplasm, and various organelles, all surrounded by a semipermeable cell membrane.

The term "cancer" is defined for the purposes of the invention refers as all types of cancer or neoplasm or malignant tumours found in mammals, including carcinomas and sarcomas. Examples of cancers are cancer of the brain, breast, cervix, colon, head & neck, kidney, lung, non-small cell lung, melanoma, mesothelioma, ovary, sarcoma, stomach, uterus and Medulloblastoma.

The term "pharmaceutical composition" is to be construed broadly and is defined for the purposes of the present invention as optionally comprises of one or more pharmaceutically acceptable adjuvants, excipients, carriers, buffers, diluents and/or customary pharmaceutical auxiliary substances. The composition of the present invention is administered in a pharmaceutically acceptable formulation. The present invention pertains to any pharmaceutically acceptable formulations, such as synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes. In addition to the said composition and the pharmaceutically acceptable polymer, the pharmaceutically acceptable formulation of the invention can comprise additional pharmaceutically acceptable carriers and/or excipients.

The term "pharmaceutically acceptable carrier" is defined for the purposes of the present invention to include any and all solvents dispersion medicoatings, antibacterial and anti fungal agents, isotonic and absorption delaying agents, and the like that are physiologically compatible. For example, the carrier can be suitable for injection into the cell, tissues, organs and/or blood. Excipients include pharmaceutically acceptable stabilizers and disintegrants.

In another embodiment, the pharmaceutically acceptable formulations comprise lipid-based formulations. Any of the known lipid-based drug delivery systems can be used in the practice of the invention. For instance, multivesicular liposomes (MVL), multilamellar liposomes (also known as multilamellar vesicles or MLV), unilamellar liposomes, including small unilamellar liposomes (also known as unilamellar vesicles or SUV), large unilamellar liposomes (also known as large unilamellar vesicles or LUV), multivesicular siosomes (MVS), multilamellar siosomes (MLS), unilamellar siosomes including small unilamellar siosomes can all be used so long as a sustained release rate of the carrier system composition of the invention can be established.

The term "therapeutic carrier system" of the present invention can include pharmaceutically acceptable salts of the components therein. Pharmaceutically acceptable salts include the acid addition salts that are formed with inorganic acids such as hydrochloric or phosphoric acids, or such organic acids as acetic, tartaric, mandelic and the like. Salts formed with the free carboxyl groups of the pharmaceuticals and/or additives and/or adjuvants derivatives can also be derived from inorganic bases such as sodium, potassium, ammonium, calcium or ferric hydroxides, and such organic bases as isopropylamine, trimethylamino, 2-ethylamino ethanol, histidine, procaine and the like. Physiologically tolerable carriers are well known in the art. Exemplary liquid carriers are sterile aqueous solutions which contain no materials in addition to the active ingredients and water, or contain a buffer such as sodium phosphate at a physiological pH value, in a physiological amount of saline or both, for example phosphate-buffered saline. Further still, aqueous carriers can contain more than one buffer salt, as well as salts such as sodium and potassium chlorides, dextrose, propylene glycol, polyethylene glycol and other solutes. Liquid compositions can also contain liquid phases in addition to and to the exclusion of water. Exemplary examples of such additional liquid phases include glycerine, vegetable oils such as cotton seed oil, organic esters such as ethyl oleate, and water-oil emulsions A pharmaceutical carrier system may also, or alternatively, contain one or more drugs, which may be linked to a modulating agent or may be free within the composition. Virtually any drug may be administered in combination with a modulating agent as described herein, for a variety of purposes as described below.

Examples of types of drugs that may be administered with a modulating agent drugs (e.g., taxol or mitomycin C), anti-inflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsycotics, antipyretics, antiseptics, anti-signalling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympatho-mimetics, sedatives, stimulants, sympathomimetics, toxins (e.g., cholera toxin), tranquilizers and urinary anti-infectives.

Formulations for oral use may also be presented as hard gelatine capsules where in the active ingredient is mixed with an inert solid diluent, for example calcium carbonate, calcium phosphate or kaolin, or as soft gelatine capsules wherein the active ingredient is mixed with water or an oil medium, for example peanut oil, liquid paraffin or olive oil.

The term "drug delivery across the oral mucosa" is defined for the purposes of the present invention as a delivery system designed to deliver drugs systemically or locally via buccal mucosa.

Buccal delivery refers to the drug release which can occur when a dosage form is placed in the outer vestibule between the buccal mucosa and gingival. Buccal route of drug delivery provides the direct access to the systemic circulation through the jugular vein bypassing the first pass hepatic metabolism leading to high bioavailability. Other advantages such as excellent accessibility, low enzymatic activity, suitability for drugs or excipients that mildly and reversibly damage or irritate the mucosa, painless administration, easy withdrawal, facility to include permeation enhancer/enzyme inhibitor or pH modifier in the formulation, versatility in designing as multidirectional or unidirectional release system for local or systemic action.

The term "buccal dosage forms" is defined for the purposes of the present invention as the buccal dosage forms including buccal adhesive tablets, patches, films, semisolids (ointments and gels) and powders:

Buccal Mucoadhesive Tablets

Buccal mucoadhesive tablets are dry dosage forms that have to be moistened prior to placing in contact with buccal mucosa.

Patches and Films

Buccal patches consists of two laminates, with an aqueous solution of the adhesive polymer being cast onto an impermeable backing sheet, which is then cut into the required oval shape.

Semisolid Preparations (Ointments and Gels)

Bioadhesive gels or ointments have less patient acceptability than solid bioadhesive dosage forms, and most of the dosage forms are used only for localized drug therapy within the oral cavity.

The term "oral mucosa" is defined for the purposes of the present invention as the mucous membrane epithelium (and lamina propria) of the mouth. It can be divided into three categories.

Masticatory mucosa, para-keratinized stratified squamous epithelium, found on the dorsum of the tongue, hard palate and attached gingiva.

Lining mucosa, non-keratinized stratified squamous epithelium, found almost everywhere else in the oral cavity.

Buccal mucosa refers to the inside lining of the cheeks and is part of the lining mucosa.

Specialized mucosa, specifically in the regions of the taste buds on the dorsum of the tongue.

The term "sublingual delivery", is defined for the purposes of the invention as delivery system consisting of administration through the membrane of the ventral surface of the tongue and the floor of the mouth. They compromise of orally disintegrating or dissolving medications that are administering by being placed under the tongue. Drugs diffuse into the blood through tissues under the tongue.

The term "transmucosal drug delivery", is defined for the purpose of the present invention as the drug entering through, or across, a mucous membrane.

The term "mucous membranes (or mucosae or mucosas; singular mucosa)" is defined for the purpose of the invention as linings of mostly endodermal origin, covered in epithelium, which are involved in absorption and secretion. They line cavities that are exposed to the external environment and internal organs. They are at several places contiguous with skin: at the nostrils, the lips of the mouth, the eyelids, the ears, the genital area and the anus. The sticky, thick fluid secreted by the mucous membranes and glands is termed mucus.

The term mucous membrane refers to where they are found in the body and not every mucous membrane secretes mucus. The glans clitoridis, glans penis (head of the penis), along with the inside of the foreskin and the clitoral hood, are mucous membranes. The urethra is also a mucous membrane. The secreted mucus traps the pathogens in the body, preventing any further activities of diseases.

The term "transdermal drug delivery" is defined for the purposes of the present invention as, relating to, being, or supplying a medication in a form for absorption through the skin into the bloodstream.

The term "local drug delivery" is defined for the purposes of the present invention as relating to, being, or administration of a drug through all areas other than the sublingual and buccal delivery.

The term "fast oral transmucosal (FOT)" is defined for the purposes of the present invention as, relating to, being, or supplying medication in a form for absorption through all areas of buccal mucosa and the sublingual route into the bloodstream.

The term "orodispersible films (ODF)" is defined for the purposes of the present invention as strips of thin polymeric films disintegrating or dissolving instantaneously when administered to the oral cavity.

The term "rapid film" is defined for the purposes of the present invention as very thin film which is applied in the mouth. It is based on a water soluble polymers. The design can vary from single to multilayer systems.

The term "orodispersible tablets (ODT)" is defined for the purposes of the patent coated or uncoated tablets intended to be placed in the mouth where they disperse rapidly before being swallowed.

The term "orodispersible granules (micro-pellets)" is defined for the purposes of the patent as coated or uncoated particles for immediate or sustained release filled in stick packs or sachets intended to be placed in the mouth where they disperse rapidly before being swallowed.

The term "Aqueous suspensions" is defined for the purpose of the patent as compositions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinyl-pyrrolidone.

The term "Oily suspensions" is defined for the purpose of the invention as formulations which may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid. Dispersible powders and granules suitable for preparation of an aqueous suspension by the addition of water provide the active ingredient in a mixture with a dispersing or wetting agent, suspending agent and one or more preservatives. Suitable dispersing or wetting agents and suspending agents are exemplified, for example sweetening, flavouring and colouring agents, may also be present.

The pharmaceutical carrier systems of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters/partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain demulcent, preservatives, flavouring agents and colouring agents. The pharmaceutical carrier systems may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as absolution in 1, 3-butane diol.

For administration to patients, the active substances of the present invention are mixed with a pharmaceutically acceptable carrier or diluent in accordance with routine procedures. Therapeutic and/or immunologic formulations will be administered by intravenous infusion or by subcutaneous injection. The formulations can also contain, if desired, other therapeutic agents.

DESCRIPTION OF THE APPLICATION OF THE INVENTION

The invention relates also to compositions and methods for the treatment of the above mentioned pathological conditions. The compositions of the present invention can be administered prophylactically or therapeutically, preferably in an amount that is effective against the mentioned disorders, to a warm-blooded animal, for example a human, requiring such treatment, the compounds preferably being used in the form of pharmaceutical carrier systems.

Pharmaceutical composition according to the invention comprising proline, or proline derivatives, or their salts, or esters, or isomeres, or racemates, or enantiomers, or prodrugs thereof for use as medicament in the prophylaxis, prevention, reduction, attenuation, stabilisation, and/or elimination, of dementia, characterised in that said treatment comprises administration of said pharmaceutical composition to a subject in need of said treatment for dementia, and/or neurodegenerative diseases or neuromuscular degenerative disorders caused by or associated with one or more of the following pathological conditions:

Alzheimer, AIDS, Parkinson's disease, Lewy body disease, Pick's disease, Huntington's disease, Creutzfeldt-Jakob disease, brain tumor, hydrocephalus, head trauma, multiple sclerosis, prolonged abuse of alcohol or other drugs, vitamin deficiency: thiamin, niacin, or $B_{12}$, hypothyroidism, hypercalcemia. Pharmaceutical composition according to the invention is for use as a medicament characterised in that said treatment comprises administration of a pharmaceutically effective dose of a second agent.

The pharmaceutical composition for use as a medicament as described herein may be characterised in that a second agent is selected from the group consisting of at least one member of a pharmaceutical proline derivatives or their salts, or esters, or isomers, or enantiomers, or racemates, or pro-drugs, beta-myeloid inhibitors, Anti-CTGF therapeutics, amino acids such as arginine, carnitine/carnitine derivatives, neurotransmitters such a dopamine, vitamins, caffeine, antifibrotic agents, memory activating agents, neuroprotective agents, glutamate-antagonist glutathione, anti-Alzheimer's disease agents, rivastigmine, donepezil, memantine and tacrine, antioxidants, NMDA receptor antagonist, anti-AIDS drugs, antipsychotic drugs such as buspirone, antidepressants such as selective serotinin reuptake inhibitors (SSRIs) such as sertraline or paroxetine, mood stabilizers, anticonvulsant, antigens, antibodies, genetic materials such as siRNA, RNA, DNA, catecholamine's, hormones, sympatholytic (adrenergic blocking) agents such as ergot alkaloids.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intra-muscular administration and formulation.

In certain applications, the pharmaceutical carrier systems disclosed herein may be delivered via oral administration. As such, these carrier systems may be formulated with an inert diluent or with an assimilable edible carrier, or they may be enclosed in hard- or soft-shell gelatine capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like.

The tablets, troches, pills, capsules and the like may also contain the following: a binder, as gum tragacanth, acacia, cornstarch, or gelatine; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavouring agent, such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit.

For instance, tablets, pills, or capsules may be coated with shellac, sugar, or both. A syrup of elixir may contain the active compound sucrose as a sweetening agent, methyl and propylparabens as preservatives, a dye and a flavouring, such as cherry or orange flavour. Of course, any material used in preparing any dosage unit form should be pharmaceutically pure and substantially non-toxic in the amounts employed. In addition, the active compounds may be incorporated into sustained-release preparation and formulations.

Typically, these formulations contain at least 0.1% of the active compound of the invention or more, although the percentage of the active ingredient(s) may, of course, be varied and may conveniently be between about 1 or 2% and about 60% or 95% or more of the weight or volume of the total formulation. Naturally, the amount of active compound (s) in each therapeutically useful carrier system may be prepared is such a way that a suitable dosage will be obtained in any given unit dose of the compound.

Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable. For oral administration the carrier systems of the present invention may alternatively be incorporated with one or more excipients in the form of a mouthwash, dentifrice, buccal tablet, oral spray, or sublingual orally-administered formulation. Alternatively the carrier systems may be fashioned into a tablet or solution form that may be placed under the tongue or otherwise dissolved in the mouth.

In certain circumstances it will be desirable to deliver the pharmaceutical carrier systems disclosed herein parenterally, intravenously, intramuscularly, subcutaneously or even intraperitoneally. Solutions of the active compounds as free bases or as pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like.

In many cases, it will be preferable to include isotonic agents, for example, sugars or sodium chloride. Prolonged absorption of the injectable carrier systems can be brought about by the use in the carrier systems of agents delaying absorption, for example, aluminium monostearate and gelatine.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some necessary variation in the dosage will occur depending on the condition of the subject being treated. The person responsible for administration will, in any event, determine the appropriate dose for the individual subject. Moreover, for human administration, preparations should meet sterility, pyrogenicity, and the general safety and purity standards as required by national or regional offices of biologics standards.

Sterile injectable solutions are prepared by incorporating the active compounds in the required amount in the appropriate solvent with various ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The carrier systems disclosed herein may be formulated in a neutral or salt form.

Pharmaceutically-acceptable salts include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug-release capsules, and the like.

In certain embodiments, the pharmaceutical carrier systems may be delivered by intranasal sprays, inhalation, and/or other aerosol delivery vehicles. Likewise, the delivery of drugs using intranasal microparticle resins and lysophosphatidyl-glycerol compounds are also well-known in the pharmaceutical arts.

In certain embodiments, the inventors contemplate the use of nanocapsules, microparticles, microspheres, and the like, in the production of the carrier systems of the present invention. Such formulations may be preferred for the introduction of pharmaceutically-acceptable formulations of the carrier system or constructs disclosed herein.

The invention provides for pharmaceutically-acceptable nanocapsule formulations of the carrier systems of the present invention. Nanocapsules can generally entrap compounds in a stable and reproducible way. To avoid side effects due to intracellular polymeric overloading, such ultra fine particles (sized around 0.1 μm) should be designed using polymers able to be degraded in vivo. Biodegradable polyalkyl-cyanoacrylate nanoparticles that meet these requirements are contemplated for use in the present invention.

The subjects treated will typically comprise of mammals and will preferably be human Subjects. The compounds of the invention may be used alone or in combination.

Additionally, the treated compounds may be utilized with other types of treatments, e.g., cancer treatments. For example, the subject compounds may be used with other chemotherapies, e.g., tamoxifen, taxol, methothrexate, biologicals, such as antibodies, growth factors, lymphokines, or radiation, etc. Combination therapies may result in synergistic and/or additive results. The preferred indication is neurodegenerative, neuromuscular degenerative diseases especially the diseases identified previously.

DESCRIPTION OF THE PREFERRED ADVANTAGES OF THE INVENTION

The present invention is based on the surprising and unexpected discovery that administration of cis-4-hydroxy-l-proline CHP, or other compounds of the invention, can prevent, reduce and/or eliminate symptoms of Dementia and Alzheimer's disease and improvement the quality of life of the patients. Based on the results generated, but not limited to the examples in this invention through the performance of comprehensive in vitro and in vivo preclinical studies in animals, and clinical studies with CHP in healthy volunteers and patients: CHP has shown surprisingly the following:

Multi-Target Pharmacological Effects

Anti-Alzheimer and Anti Dementia Effects

Surprisingly and unexpected that the repeated administration of oral and/or intravenous CHP for (90-540 consecutive days/2-12 gram per day) als mono-therapy to patients with mild or moderate Alzheimer's disease and Dementia has shown significant improvement of the following conditions and quality of life in comparison to their status prior to the start of the treatment (Examples 11 and 12).

Cognitive conditions: Concentrating on things like reading a newspaper or watching television; remembering things; drug compliance; and awareness of self; Physical condition: Work capacity, daily activities (eating, dressing, washing, toilet, shopping, doing household jobs, travelling, walking), Emotional conditions: Feeling and mood; tense; worry; depression; pain; fatigue; enjoyment of activities; Social interactions: Family life, Other conditions: Sleeping; appetite, Quality of Life.

Treatment of CHP and THP Deficiencies

Surprisingly and unexpected that the CHP blood level required for prevention, attenuation, therapy, diagnosis follow-up, and/or aftercare of said dementia, Alzheimer's, neurodegenerative diseases, and neuromuscular degenerative disorders was achieved by the administration of the different pharmaceutical formulations of CHP formulations according to this invention.

In addition the treatment was adjusted using the Prophylactic and/or Therapeutic Drug Monitoring PDM/TDM following the determination of CHP and THP using a sensitive and selective HPLC for CHP and THP as biomarkers.

Surprisingly and unexpected that the prophylactic and/or treatment CHP-level in blood (>endogenous plasma level for the individual patients) could be achieved by the administration of low dose of oral CHP (Examples 3-5).

Anti-Fibrotic Activities

Surprisingly and unexpected according to this invention (example 12.4) that: CHP inhibited the hepatic fibrosis (Transforming growth factor beta 1 (CGFβ1), Procollagen type III, Collagen type IV, Apolopoprotein A1, Hyaluronic Acid, Laminin, Alpha-2-macroglobulin) in patients suffering from chronic liver diseases.

Anti-Proliferative Activities

Surprisingly and unexpected CHP has shown according to the examples in this invention anti-proliferative effects, in vivo anti-metastasis activities, anti-angiogenesis activities, cell cycle arrest, induction of proteolysis of FAK and ER Stress (there is strong evidence that mitochondrial dysfunction and oxidative stress play a causal role in neurodegenerative disease pathogenesis, including in four of the more well known diseases Alzheimer's, Parkinson's, Huntington's, and amyotrophic lateral sclerosis), inhibition of Na+/k+-ATPase, induction of ionic imbalance, inhibition of Epidermal Growth Factor Receptors EGFR, inhibition of Glutathione-S-Transferase (GST), inhibition of Collagen IV, an increase of the sensitivity of tumour cells to cytokines as tumour necrosis, acceleration of the terminal differentiation or apoptosis of the cells, activation the tyrosine kinase inhibitor (Examples 3-7).

Immunological Activities:

Surprisingly and unexpected CHP has shown increase of the immunological activities of interleukin-2, Interleukin-12, and Interferon-alpha. This means CHP has shown according to the results of the examples represented in this invention that it impacts separate targets to create a combination effect on the Alzheimer and Dementia. The targets can reside in the same or separate pathways within cell, or in separate tissues (Examples 12.1-12.4).

The invention further provides the methods for the administration of CHP and/or the compound of the invention for healthy subject and patients as follows:

1. Administration of CHP at an early stage to healthy volunteers/subjects at a young age, subjects with high risk to alzheimer's disease and neurodegenarative disease not limited to subjects with Down Syndrome, or with genetic Alzheimer's history with the effect to maintain the physiological levels of CHP and THP in the blood/cerebral fluid, and brain tissue and for the prophylactic development of Alzheimer's disease, and/or other neurodegenerative, and/or neuromuscular degenerative disorders.

2. Administration of CHP at early stage of the Alzheimer's Disease treats the deficiency of CHP/THP in blood, cells, biological fluids and tissues of the subject. The administration of CHP will normalize and maintain the CHP and THP levels in the blood/cerebral fluids, and brain tissues at the physiological level and stabilize and/or eliminate the Alzheimer's disease, other neurodegenerative, and/or neuromuscular degenerative disorders.

3. Administration of CHP at advanced stages of Alzheimer's Disease, other neurodegenerative, and neuromuscular degenerative disorders will treat the CHP/THP deficiency and normalize and maintain the CHP level in blood/cerebral fluids, and brain tissues at the physiological level and treat the disease.

The invention further provides the method for use of CHP and/or THP as biomarkers and tests that can be used to follow body processes and diseases in humans and animals.

They can be used to predict how a subject will respond to the administration of CHP and/or the composition according to this invention or whether they have, or are likely to develop, a certain disease. For example, the levels of CHP in blood and/or synovial fluid may be able to predict the likelihood that a patient with mild memory problems will go on to develop dementia due to Alzheimer's disease. Alzheimer's disease is, as of 2013, incurable; however, early diagnosis and prompt intervention can slow the progression of the disease. As of 2009, the United States Food and Drug Administration (FDA) had approved five prescription drugs for the treatment of AD symptoms. Four of these are used to treat mild to moderate AD. They are galantamine (Razadyne formerly known as Reminyl), rivastigmine (Exelon), donepezil (Aricept), and tacrine (Cognex). Tacrine, however, is rarely prescribed because of safety issues. None of these drugs cure or stop AD. In some individuals, they do slow the progression of symptoms by modestly increasing cognition and improving the individual's ability to perform normal activities of daily living. Existing therapies for dementia and Alzheimer's disease use high doses of drugs and resulting in severe side effects and poor quality of life. Unexpected and surprisingly according to the examples of this invention patients suffering from Alzheimer's diseases have shown very low blood concentrations of cis 4-Hydroxy-L-proline (CHP), and trans 4-Hydroxy-L-proline (THP) in comparison to healthy subjects.

The efficacy of cis 4-Hydroxy-L-proline (CHP) and trans 4-Hydroxy-L-proline (THP) on the prophylaxis and therapeutic efficacy on dementia and/or Alzheimer's and neuro degenerative disease seems to be caused through complex effects as a result of the multi-target mode of action of CHP and THP on the molecular and trans-membrane levels and the intracellular mechanisms of the cells. Therefore the inventor postulated, that one or more of the following pharmacological activities will provide the desired effects:

1. The administration of CHP will normalise the level of CHP and THP in blood and tissues through the compensation of the serious deficiencies of the CHP and THP concentrations in the blood, cerebrospinal, and brain of the patients suffering from dementia, Alzheimer's Diseases (AD), neuromuscular degenerative disorders such as Parkinson and CNS's disorders e.g. schizophrenia. This means the concentration of CHP and THP in blood and tissues will be adjusted by this replacement therapy to a physiological level range.

2. Modification of the nerve/cell membrane through the modification of the collagen biosynthesis in the brain cells and tissues by CHP. This will enable the achievement of the cellular physiological transport mechanisms (cellular influx and outflux), and will avoid the intracellular accumulation of endogenous proteins and other proteins, lipids and cell degradation products which may cause the molecular damages. 3. CHP/THP may act to increase the effectiveness of the intracellular maintenance mechanisms, such as by increasing and/or replacing production deficiencies of physiologically occurring compounds.

4. CHP/THP may act as a treatment agent that retards the cellular/intracellular ageing process by slowing the deteriorative processes and the molecular damage. 5. CHP/THP as prophylaxis agent for dementia and/or Alzheimer's disease (AD) may prevent the misrepair as a defective structure in the cell/nerve cell, which accumulates with time and causes gradually the disorganisation of a structure (tissue, cell, or molecule), which is the source of ageing.

6. Inhibition of glutathione-S-transferase (GST) by CHP: As it has been shown in the examples of this invention that CHP inhibits significantly GST. It is known that GST binds oncogenes and/or parts and fragments of the cells with glutathione in order to prepare them for the extracellular transport, Therefore an inhibition of GST could lead to a decrease of a tumor-cell and fragments spreading-effect. This will result in the reduced formation of metastases and plaques.

7. CHP/THP may promote the apoptosis due to a high level of cell transformation (including damage) and cell death, the concentration of potential intracellular material could possibly lead to intoxication.

8. CHP is incorporated into the proteins and prevents the folding of triple helical. As consequences of the effects of CHP on the collagen formation/inhibition:
 CHP will decrease the formation of normal folded collagen and this will result in the reduction of the fibrotic process and development.
 Accumulation of misfolded collagen in endoplasmatic reticulum (ER) resulting in ER-stress by pathway of unfolded protein response (UPR).
 ER-stress will lead to growth inhibition and induction of apoptosis. It is known that collagen IV is part of the cell membrane and part of the extracellular matrix. Tumour cells bind to the main-collagen domain of this glycoprotein (=collagen) to penetrate the cell. As a result of the above mentioned pharmacological effects of CHP, different indications are possible where the inhibition of collagen IV is of great advantage such as inhibition of this receptor in the cell membrane as very important with respect to all tumour diseases, all illnesses where transformation of normal tissue into connective tissue takes place (e.g. fibrosis), Sclerodermia/Marfan-Syndrom, metabolic illnesses, vascular illnesses, autoimmune diseases, neurological illnesses where normal nerve tissue is transformed into connective tissue (e.g. Alzheimer, Gliosen), additive application in the therapy with drugs that induce fibrosis, e.g. Bleomycin, Busulfan—additive/supportive therapy. CHP as inhibitor of collagen IV may prevent the formation of the different aggregates.

As examples:
 Several neurodegenerative diseases are classified as proteopathies as they are associated with the aggregation of misfolded proteins.
 Alpha-synuclein can aggregate to form insoluble fibrils in pathological conditions characterized by Lewy bodies, such as Parkinson's disease, dementia with Lewy bodies, and multiple system atrophy. Alpha-synuclein is the primary structural component of Lewy body fibrils. In addition, an alpha-synuclein fragment, known as the Non-Abeta component (NAC), is found in amyloid plaques in Alzheimer's disease.
 Hyperphosphorylated tau protein is the main component of neurofibrillary tangles in Alzheimer's disease.
 Beta amyloid is the major component of senile plaques in Alzheimer's disease.
 Parkinson's disease and Huntington's disease are both late-onset and associated with the accumulation of intracellular toxic proteins. Diseases caused by the aggregation of proteins are known as proteinopathies.

9. CHP inhibits the uptake of proline into the malignant cell based on competitive block of the relevant amino acid transport mechanism and the concentration of intracellular proline will be decreased. A decreased concentration of proline causes a decrease in the biosynthesis and availability of collagen IV for the malignant cell i.e. less collagen IV is available for the tumour cell's angiogenesis. Consequently the supply of nutritive substances is disturbed. This may also lead to a decreased growth of the tumour cells. This means, that the concentration and the aggregation of misfolded proteins will decrease.

Considering these results together with the recently reported and published hypothesis by Lary C. Walker, et al. m (JAMA Neurol. 2013 Mar. 1; 70(3): on the mechanism of Alzheimer's disease which says that "recent evidence indicates that, in a variety of neurodegenerative diseases, protein aggregation is initiated and the aggregation continue to proliferate, by a prion-like process of templated protein corruption, or seeding" it is logical to consider potential similarities in the mode of action and/or mechanisms of tumour proliferation, protein aggregation, and the prion-like process in Alzheimer's disease and other neurodegenerative disorders.

10. CHP disrupts the intracellular signal pathways. Focal adhesion kinase (FAK), proteolytic fragmentation and inactivation of FAK by CHP leads to reduction of FAK-activity and the loss of cell adherence and as a result induction of apoptosis 11. Affection of intracellular ion homeostasis and extracellular acidity: CHP effects extensive intracellular vacuolization in colon and pancreatic tumor cell lines by affecting intracellular ion homeostasis of $K+$, $Na+$ and $H+$ most likely involving $Na+/K+$-ATPase, which has been shown to be differentially expressed in tumor cells. Tumor cell proliferation may be further limited by the generation of a CHP-induced acidic extracellular environment and down regulation of the EGF receptor.

12. CHP seems to increase immunologically relevant pathways represented by increased levels of Interleukin1, Interleukin 6, Interleukin12 under CHP therapy. Dysregulated immune response has been linked to Alzheimer's disease (AD). Although direct causal relationships have not been established for all detrimental outcomes, the immune system has been indirectly implicated.

Cells and tissues have vital parts that wear out resulting in ageing. It is known that some neurological diseases are considered to be at high risk with increasing age, for example, AD, which is diagnosed in people over 65 years of age. Discovery of molecular basis of the processes involved in their pathology or creating and studying aging model systems may help our better understanding the aging processing.

Therefore the early improvement of the immunological status of healthy subjects and/or patients suffering or will suffer from dementia and/or Alzheimer's disease and neurodegenerative diseases may have positive effect in the prophylaxis, prevention, diagnosis, attenuation, therapy, follow-up and/or aftercare of said dementia and/or Alzheimer's disease.

13. Antifibrotic efficacy: According to the examples (Clinical Phase II-Ill study-No. IPSS B025-L) of this invention, CHP has shown antifibrotic efficacy in patients suffering from chronic liver diseases. The antifibrotic efficacy of CHP could be considered clinically as very relevant to prevent the accumulation of misfolded proteins, alpha synuclein, hyperphosphorylated tau protein and beta amyloid.

Advantages of Cis 4-Hydroxy-L-Proline (CHP) as Multitarget Agent for Prophylaxis, Prevention, Diagnosis, Attenuation, Therapy, Follow-Up and/or Aftercare of Said Dementia and/or Alzheimer's Disease Based on the surprisingly and unexpected results generated from the performed preclinical, pharmacological, and clinical studies with cis-4-Hydroxy-L-proline (CHP), trans 4-Hydroxy-L-proline (THP), their esters, salts, enantiomers, isomers, and derivatives in this invention, the inventor postulates that:

The administration of CHP as collagen modulator, antifibrotic agent, inhibitor of GST and collagen IV, inhibitor of intracellular signal pathways of the Focal Adhesion Kinase (FAK), affection properties of intracellular ion homeostasis and extra-cellular acidity, and immunological activities may effect the prophylaxis, prevention, attenuation, therapy, of said dementia and/or Alzheimer's disease through one or more of the following possible mode of action of CHP as Multi-Target-Agent to provide the desired efficacy:

1. Elevation/normalisation and/or compensation of the CHP and THP concentrations in blood, CNS fluids and tissues. This means the treatment of the CHP and/or THP serious deficiency in blood, tissues and CNS of human subjects.
2. Inhibition of the initiation, aggregation, and proliferation of the proteins in the brain which are responsible for causing the Alzheimer's disease, neurodegenerative and neuromuscular degenerative disorders and Schizophrenia.
3. Inhibition of the formation and deposits of beta-amyloid fragment in the brain.
4. Inhibition of the fibrillar amyloid plaques in the brain.
5. Inhibition of the formation of neurofibrillary tangles inside the nerve cell bodies.
6. Inhibition of the formation of sanile plaques in the brain tissues.
7. Inhibition of the protein misfolding disease (proteopathy), caused by accumulation of abnormally folded tau proteins in the brain.
8. Inhibition of the tauopathy which is caused by abnormal aggregation of the Tau protein.
9. Inhibition of the oxidative stress and dys-homeostasis of biometal (biology) metabolism.

Surprisingly and unexpected according to the results generated from the studies represented in the examples of this invention that the plasma half-life of CHP was approximately 4 times higher than the dosing interval, accumulation of CHP became extensive following oral administration and the accumulation of THP also reached a remarkable extent.

In addition surprisingly and unexpected that the simulation of plasma concentration-time curves of CHP and THP up to 19 days after administration was achieved with reasonable quality especially with regard to CHP. After approximately 48 h and 96 h, a steady state was observed for CHP and THP, respectively.

It is also surprisingly and unexpected that CHP cross the blood-brain barrier and that the concentration in the brain tissue is relatively high.

Furthermore it is surprisingly and unexpected that the maximal concentration of CHP in the brain following the oral administration is high, approximately 48% in comparison to the intravenous application. This is a great advantage for the patients to take the drug orally at home (out patients). They will enjoy shopping, traveling and practicing their daily activities. In addition will cut drastically the treatment costs.

Assessment of the experimental clinical studies in this invention with CHP in healthy volunteers and patients provided herein, has revealed unexpected a surprising and beneficial absence of the previously reported side effects following the repeated high doses (8 grams) of intravenous and oral CHP for long treatment periods for 180 to over 400 consecutive days.

The search of alternative for strategies for prophylaxis, prevention, diagnosis, attenuation, therapy, follow-up and/or aftercare of said dementia and/or Alzheimer's disease has focused on the administration of cis 4-Hydroxy-L-proline (CHP) and/or trans 4-Hydroxy-L-proline (THP), which have shown to increase the physiological level, to treat the serious deficiency and the pathological low concentration of CHP and THP in the blood of patients suffering from dementia and/or Alzheimer's disease.

The clinical utility of these agents stems from one or more effects of CHP and/or THP on the collagen modulation of CHP, antifibrotic efficacy, apoptotic/necrotic cell death, induction of ionic Imbalance, proteolysis of FAK/Induction of ER Stress, inhibition of Glutathione-S-Transferase (GST), inhibition of intracellular uptake of proline, increase of the immunological activities of interleukin-2, Interleukin-12, and Interferon-alpha, antiproliferative, antiangiogenesis and antimetastasis activities.

From a clinical standpoint, the amounts of CHP that are needed for effective normalisation and/or compensation of the low pathological concentrations of CHP and THP in blood, cerebral matrices and tissues at steady state level for the prophylaxis, prevention, diagnosis, attenuation, therapy, follow-up and/or aftercare of said dementia and/or Alzheimer's disease in patients will be relatively low and with or without mild side effects.

FIGURES

The figures provided herein represent examples of particular embodiments of the invention and are not intended to limit the scope of the invention. The following drawings form part of the present specifications and are included to further illustrate aspects of the present invention. The invention may be better understood by reference to the drawings in combination with the detailed description of the specific embodiments presented herein.

EXAMPLES

The examples provided herein represent practical support for particular embodiments of the invention and are not intended to limit the scope of the invention. The examples are covering the following areas on the Multi-Target-Effects of CHP and the compounds of the invention for the prophylaxis, prevention, attenuation, therapy, diagnosis follow-up, and/or aftercare of said dementia, Alzheimer's, neurodegenerative diseases, and neuromuscular degenerative Disorders:

Examples are to be considered as providing a further description of potentially preferred embodiments that demonstrate the relevant technical working of one or more non-limiting embodiments.

Examples—In-Vivo Pre-Clinical Investigations

Figure 1:
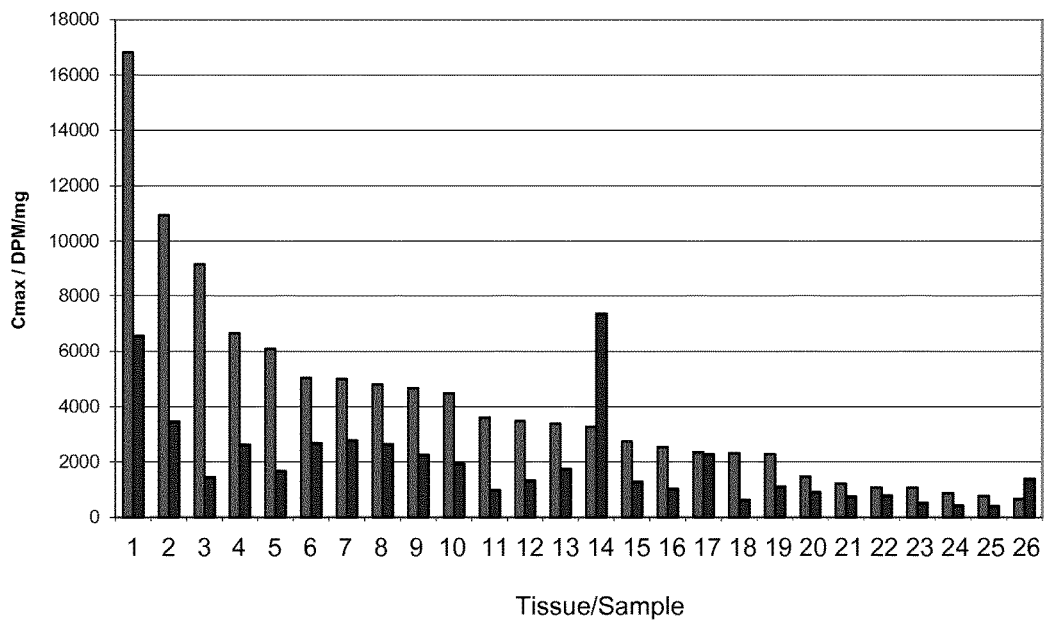
FIG. 1: Chart: Summary Cmax across 25 tissues and whole blood, following IV and oral administration of 50 µCi $^3$H-CHP (remaining carcass omitted)

Example 1: Tissue Distribution and Pharmacokinetic Study with CHP Study "Clinical Study in Mice on the Tissue Distribution and Pharmacokinetics of Single Dose of the Radiolabelled $^3$H-CHP-Study No.: IPSS C053"—(FIG. 1). This Study has been Designed and Performed According to this Invention Objectives:
1. Determination of $^3$H-CHP distribution in 25 tissues, remaining carcass and whole blood over time.
2. Determination of pharmacokinetic parameters of CHP.
3. Comparison of intravenous (IV), and oral routes of administration.
Materials and Methods:
$^3$H-CHP Labelling
CHP was labelled on the 4-prime position using tritium. The scintillation counting technique detects the tritium atom.

Therefore the counting technique detects CHP and some metabolites which incorporate the tritium. Metabolites which do not incorporate the tritium are not detected.

54 mice were enrolled. They were selected using inclusion and exclusion criteria, and were therefore highly standardised.

Dosing Regimen 48 animals were each administered 50 µCi $^3$H-CHP at the start of the experiment. This was termed time zero (00:00 hrs).

27 mice were dosed via the intravenous (IV) route.

21 mice were dosed via the oral route.

Six (6) animals were not administered with CHP. They form two control groups of 3 mice each.

Data Collection 3 mice were sacrificed following the SOP for anesthesia and according to the the following time intervals Sample Collection From each sacrificed mouse, the following samples were taken:

Whole BloodEyes & Harderian GlandsKidneys & Adrenal GlandsAortaLiverLungSpleenUrinary Bladder-Bone & Bone MarrowCaecumSmall IntestineLarge IntestineLymph Nodes (Mesenteric) Muscle, Pancreas-Brain & Pituitary GlandBrown FatSubcutaneous Fat-HeartThymousBoth TestesProstateSkinStomachThyroidSalivary GlandsRemaining CarcassUrine (collected if possible: in practise this was rare)

The remaining carcass sample consisted of the rest after removal of whole blood and the other tissues. Any material cleaned from other tissues listed above was also included. The collected remainings were homogenised before analysis.

Results

Summary of the Tissue Distribution Analysis Following Single Dose Administration of $^3$H-CHP The results from Example 1 are shown in FIG. 1

25 tissues, whole blood and remaining carcass samples were analysed.

50 µCi $^3$H-CHP was administered to each of the mice.

Remaining Carcass Following Single Dose Administration of $^3$H-CHP

Intravenous (IV) and Oral Administration

1. Following intravenous (IV) administration, the AUC-1 for remaining carcass made up 73.3% of the totaled AUC-1 for all tissues & samples. This left only 26.7% to be divided between all 25 tissues and whole blood.

2. Following oral administration, the AUC-1 for remaining carcass made up 61.8% of the totaled AUC-1 for all tissues & samples. This left only 38.2% to be divided between all 25 tissues and whole blood. This may be because: remaining carcass is primarily composed of connective tissue, and connective tissue is primarily composed of collagen Tissues primarily composed of collagen will be performing collagen synthesis, which will take place from procollagen.

3. CHP acts via incorporation into procollagen. This incorporation does not remove the tritium labelling. Procollagen has a high molecular weight, therefore is unlikely to move far from the site of bio-synthesis. This removes the incorporated CHP from circulation. Therefore a labelled CHP metabolite will accumulate in connective tissue, which makes up the majority of the remaining carcass. This effect will be useful when using CHP to treat cancer and Alzheimer's disease, neurodegenarative diseases, neuromuscular disorders and as antifibrotic agent. Patients with cancer and neurodegenerative and neuromuscular degenerative diseases would have collagen synthesis within the tumour and nerve cells in addition to endogenous collagen synthesis. As a result CHP will also concentrate in cancerous and fibrotic areas.

Accumulation of $^3$H-CHP following administration of single dose of $^3$H-CHP

The following tissues of interest accumulated particularly high CHP concentrations: Intravenous Application:

Pancreas, lymph nodes (mesenteric), kidneys & adrenal Glands, caecum, large intestine, small intestine, spleen, liver, urinary bladder.

Oral Application

Pancreas, stomach, kidneys & adrenal glands, small intestine, lymph nodes (mesenteric), spleen, caecum, bone & bone marrow, large intestine, and liver.

High concentration, Cmax and AUC-1 in the stomach have been observed in comparison to IV administration.

The $C_{max}$ following oral administration was 7.361 DPM/mg, which compares with 3.269 DPM/mg following IV administration.

The AUC-1 following oral administration was 27.297 DPM/mg, which compares with 10.493 DPM/mg following IV administration.

Accumulation of $^3$H-CHP in the Brain Following Administration of Single Dose of $^3$HCHP High concentration of $^3$H-CHP has been observed in the Brain & Pituitary Gland Concentration was observed in brain & pituitary gland. Therefore CHP can cross the blood-brain barrier.

Following IV administration, the Cmax was 876 DPM/mg. This compares with 4 DPM/mg in the control.

Following oral administration, the $C_{max}$ was 419 DPM/mg. This compares with 1 DPM/mg in the control.

Surprisingly and unexpected that CHP cross the blood-brain barrier and that the concentration in the brain tissue is relatively high.

Furthermore it is surprisingly and unexpected that the maximal concentration of CHP in the brain following the oral administration is high, approximately 48% in comparison to the intravenous application.

Figure 2:
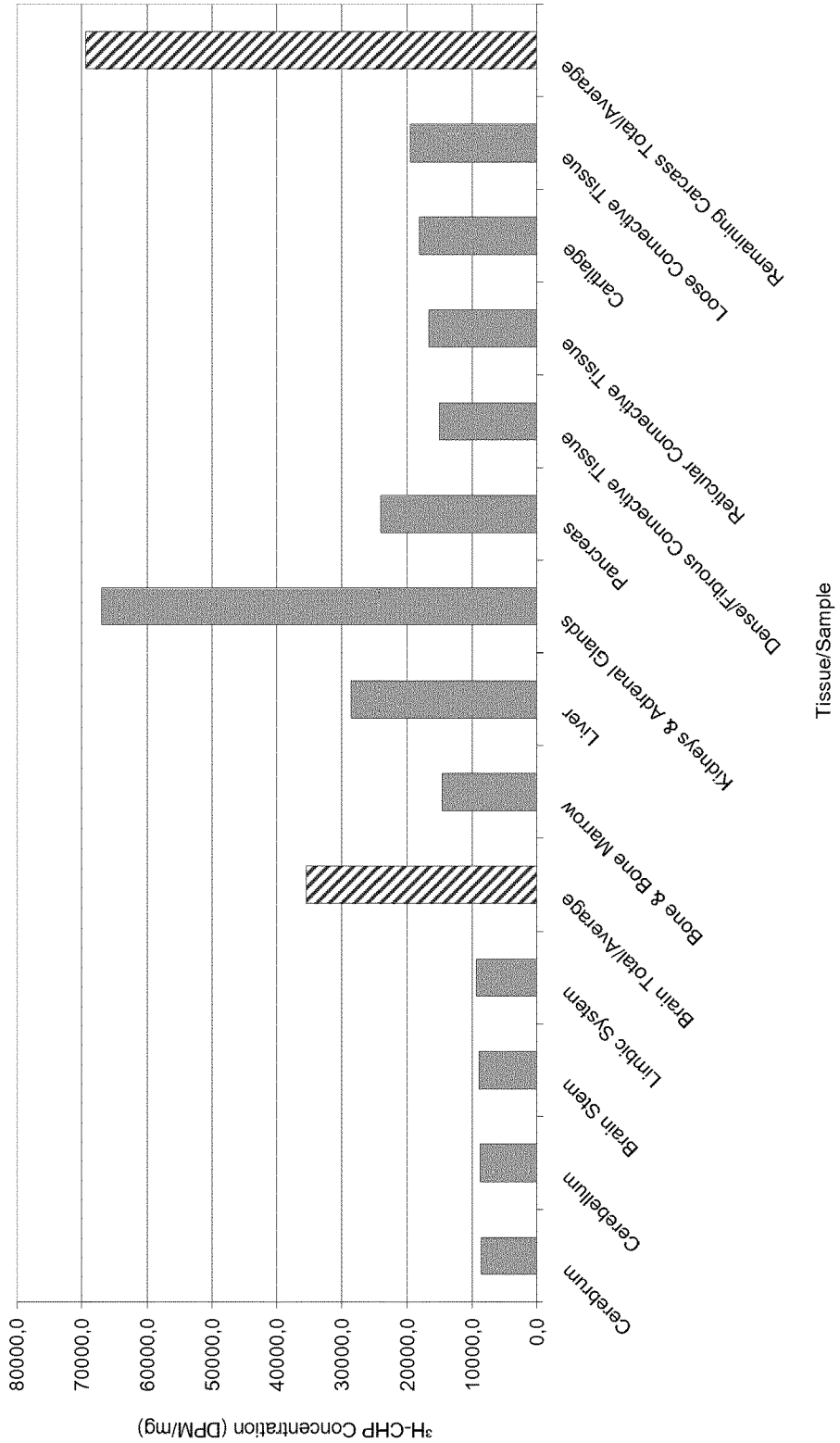
FIG. 2: Representation of the $^3$H-CHP concentration data collected from study No. E015

Example 2. A Study in Mice on the Tissue Distribution, Bioaccumulation and Pharmacokinetics in Tissues, Connective and BrainTissues Following Multiple Dose Administration of $^3$H-CHP Study No. IPSS E015 (FIG. 2)

According to this invention the study has been designed and performed as follows:

From each mouse sacrificed, the following organs & tissues samples were taken:

Liver, kidney, pancreas, limbic system, spinal fluid, brain stem, cerebrum, cerebellum, cartilage, ligaments and tendons (dense or fibrous connective tissue), loose connective tissue, and reticular connective tissue (supports lymph nodes, bone marrow, and spleen)

Summary of Tissue Distribution Analysis

The results from Example 2 are represented in FIG. 2.

The following tissues of interest were found to have particular high levels of $^3$H-CHP accumulation: kidneys and adrenal glands liver, pancreas loose connective tissue cartilage, reticular connective tissue, dense/fibrinous connective tissues.

Discussion on the Results of the Examples 1 and 2 "Clinical Tissue Distribution and Pharmacokinetics Studies" Following Single Dose of $^3$H-CHP-Study No.: IPSS C053, and Repeated Dose of $^3$H-CHP for 7 Consecutive Days—Study No.: E015

CHP has shown surprisingly and unexpected according to the examples in this invention the following findings after the repeated dose administration of oral aquous-solution of $^3$H-CHP to the animals:

Excellent penetration of the BBB as the target for the effects of CHP. in the Brain CNS, and muscles The high tissue distribution in the brain is indicative for the effective transportation of CHP via amino acid proline transporters to the brain cells.

High concentration and bioavailability in cerebrum, cerebelium, brain stem, limbic system and spinal fluid (14.9% AUC as % of total administered CHP) which will allow the prophylaxis, prevention, diagnosis, attenuation, therapy, follow-up and/or aftercare of said dementia, Alzheimer's and neurodegenerative diseases.

High concentration and bioavailability in loose connective tissues, cartilage, reticular connective tissue, dense/fibrous connective tissue, bone and bone marrow (35% AUC as % of total administered CHP) which will allow in addition to the high AUC in Brain and CNS the prophylaxis, prevention, diagnosis, attenuation, therapy, follow-up and/or aftercare of said degenerative neuromuscular diseases such as, Multiple Sclerosis, Osteoarthritis Degenerative Disc Disease, Charcot-Marie-Tooth Disorder, Neuropathy, Amyotrophic Lateral Sclerosis, ALS-Lou Gehrig's Disease, Spinocerebellar Ataxia, Friedreich Ataxia, Friedreich Ataxia, Muscular Dystrophy, Duchenne Muscular Dystrophy, and Spastic Paraplegia.

High Half-Life time (32.30-42.70 hours) in cerebrum, cerebelium, brain stem and limbic system which will be of great advantage to achieve steady state level and long mean residence time (MRT) of CHP in the different brain tissues.

In addition this will support the following hypothesis postulated by the inventor of this invention for the following possible mode of action of CHP/THP:

Removal, recovery and compensation of the serious deficiencies of the CHP and THP concentrations in the blood, cerebrospinal, and brain of the patients suffering from dementia and Alzheimer' Diseases (AD). This means the normalisation of the pathological blood and tissue concentrations of CHP and THP to the physiological level.

Modification of the nerve/cell membrane through the modification of the collagen biosynthesis in the brain to be able to achieve, restore and/or maintain the physiological transport mechanisms (cellular influx and outflux), which will avoid the membrane and intracellular accumulation of endogenous proteins and other degradation products which may cause the molecular damage, dementia, Alzheimer's, neurodegenerative and/or neuromuscular degenerative diseases.

CHP/THP may act to increase the effectiveness of the intracellular maintenance mechanisms, such as by increasing and/or replacing production deficiencies of physiologically occurring compounds.

CHP/THP may be used as a treatment agent that retards the cellular/intracellular ageing process by slowing the deteriorative processes and the molecular damage.

CHP/THP as prophylaxis agent for dementia and/or Alzheimer's disease (AD) may prevent the misrepair as a defective structure in the cell/nerve cell, which accumulates with time and causes gradually the disorganisation of a structure (tissue, cell, or molecule), which is the source of ageing.

CHP has shown surprisingly and unexpected high concentration and bioavailability, and excellent tissue distribution in the dense/fibrous connective tissues, reticular connective tissues, cartilage, and loose connective tissues as the targets for the treatment of neuromuscular disease as defined for the purposes of the present invention as a disorder that affects the peripheral nervous system. The peripheral nervous system includes muscles, the nerve-muscle (neuromuscular) junction peripheral nerves in the limbs, and the motor-nerve cells in the spinal cord.

Examples—In-Vivo—Clinical Investigations in Healthy Subjects and Patients

Examples 3-13

Pharmacokinetics of CHP and THP in Healthy Volunteers and Patients

According to the examples No. 3-13 in this invention, the pharmacokinetics (absorption, distribution and excretion) of CHP and THP in healthy subjects and patients suffering from Cancer, Alzheimer's disease, and Dementia have been investigated. The following ICH-GCP Phase I, II-III clinical studies in this invention have been performed in GCP certified clinical centres in Germany and other European countries.

1. Title: Safety, Tolerability and Pharmacokinetic Profile of Single Ascending Doses of Oral cis-4-hydroxy-L-proline (CHP) in Healthy Volunteers:
GALMED Study No: 1001-68 (Example No. 3).
2. Title: Single Dose Absolute Bioavailability (IV solution) and Safety Study of CHP in Healthy Volunteers: GALMED Study No: 0302-72 (Example No. 4).
3. Title: Multiple Dose Ascending Bioavailability and Safety Study (Phase I) with Oral CHP: GALMED study No: 0202-71 (Example No. 5).
4. Title: Measurement of α-Glutathione-S-Transferase following multiple dose administration of CHP study 0202-71 (Example No. 6).
5. Title: Measurement of Collagen-IV following multiple dose administration of CHP-Study 0202-71 (Example 7).
6. Title: Determination of Pre-dose endogenous blood plasma concentrations of CHP in healthy volunteers Study 0202-71 (Example 8).
7. Title: Determination of the pre-dose endogenous blood plasma concentrations of THP in healthy volunteers Study 0202-71 (Example 9)
8. Title: Comparisons between the abnormal and pathological endogenous blood concentrations of CHP and THP in patients with Alzheimer's disease (AD) in comparison with healthy subjects (Example 10).
9. Title: Evaluation of the efficacy, safety and Quality of Life (QoL) of 25 Clinical Cases in patients with advanced cancer disease treated with oral and intravenous formulations of Cis-4-Hydroxy-L-Proline (CHP) (Example 11).
10. Title Phase II—CHP as antitumour agent in patients with resected colorectal cancer and liver metastasis (Example 12.1).
11. Title: Phase II—CHP in patients with locally advanced or metastatic pancreatic cancer (Example 12.2).
12. Title: Evaluation of safety and efficacy of CHP in patients with urogenital Cancer (Example 12.3).
13. Title: Phase II—CHP in patients with chronic viral hepatitis, chronic alcohol liver diseases without cirrhosis or primary sclerosing cholangitis (Example 12.4).
14. Title: Quality of Life, physical, and cognitive conditions—Alzheimer—Dementia Measure (Example 13).

Examples 3 and 4

Figure 3:
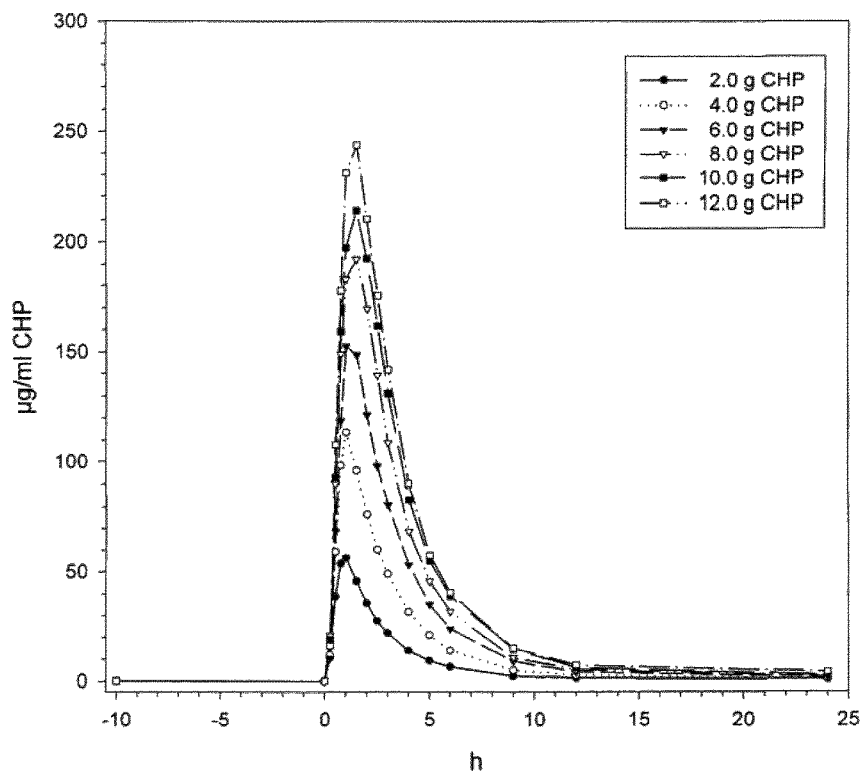
FIG. 3: CHP concentration (y-axis) against time (x-axis) following oral doses of 2 g-12 g CHP in 6 healthy volunteers
Figure 4:
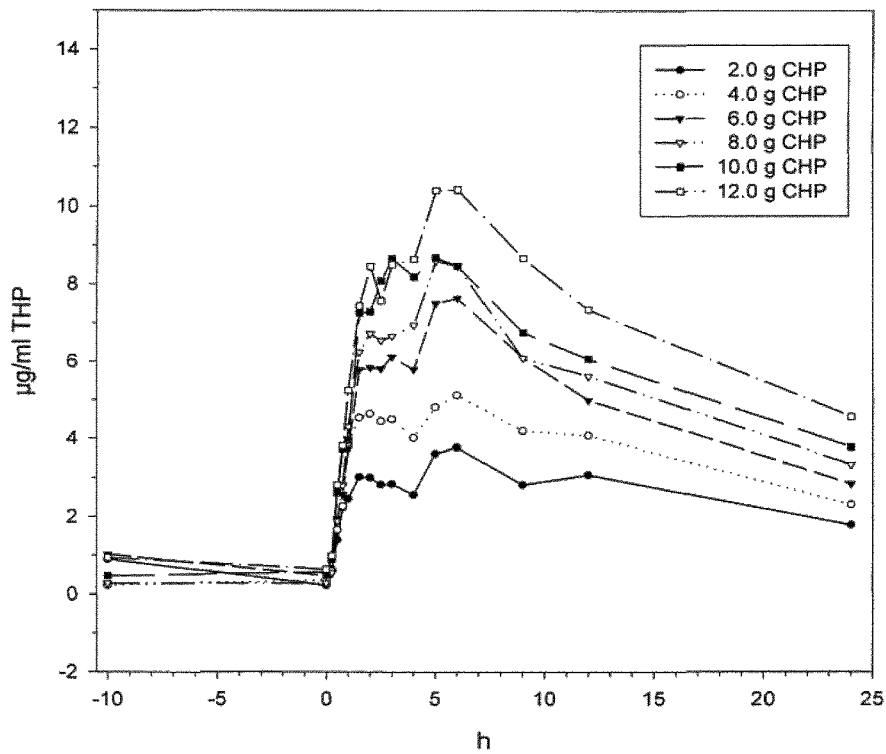
FIG. 4: THP concentration (y-axis) against time (x-axis) following oral doses of 2 g-12 g CHP in 6 healthy volunteers

Example 3 study title Safety, tolerability and pharmacokinetic profile of single ascending doses of oral cis-4-hydroxy-L-proline (CHP) in healthy volunteers Galmed study no. 1001-68-. Results FIGS. 3 and 4.

Example 4

Figure 5:
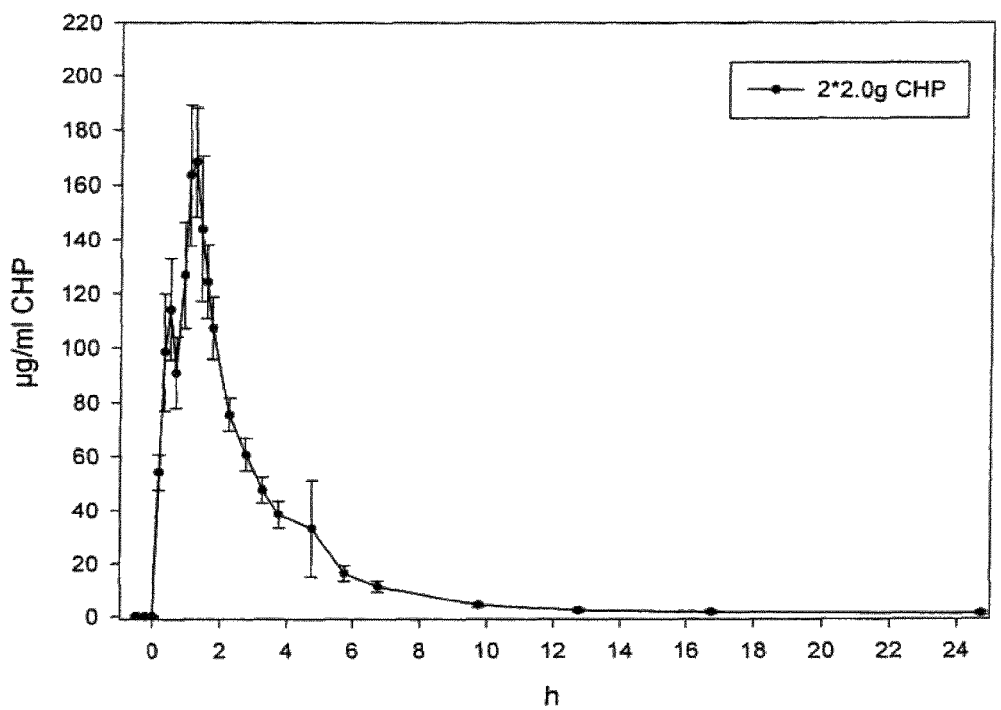
FIG. 5: Means and Standard Deviations of CHP plasma concentrations (2×2.0 g CHP) n=6
Figure 6:
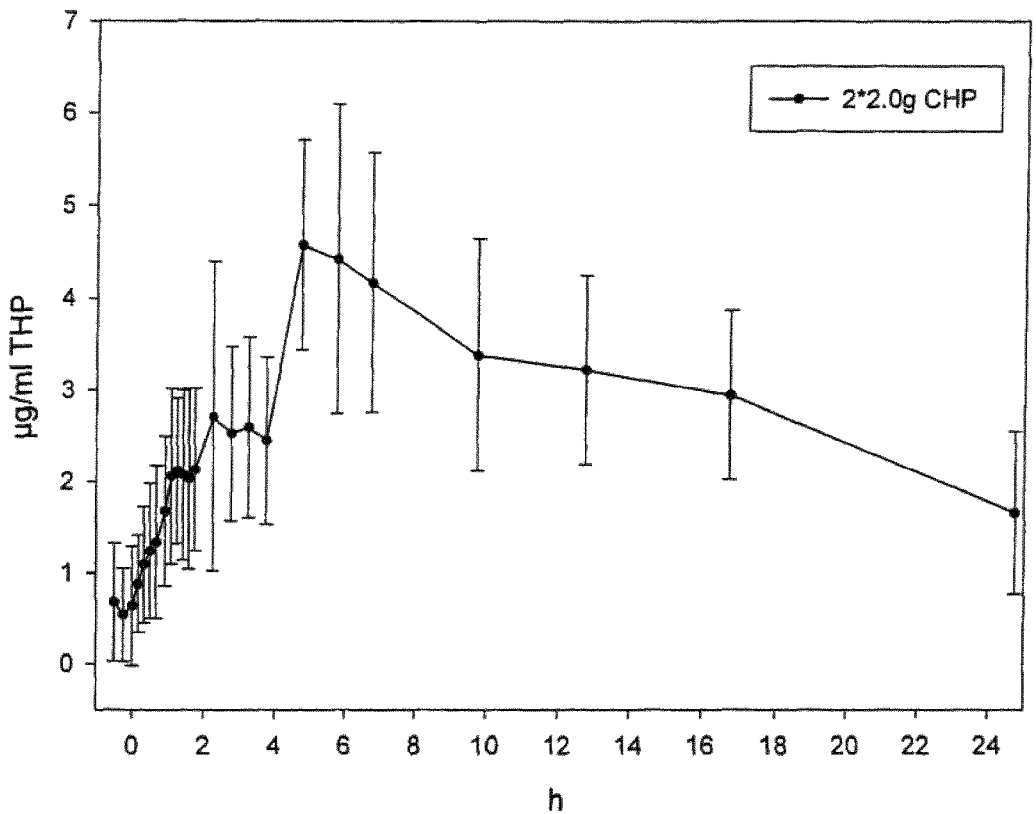
FIG. 6: Means and standard deviations of THP plasma concentrations (2×2.0 g CHP), n=6)

Study title: Single Dose Absolute Bioavailability (intravenous IV solution) and Safety Study of CHP in Healthy Volunteers-GALMED Study No: 0302-72. Results are in (FIGS. 5 and 6)

According to example 3 in this invention, the following ICH-GCP Clinical Phase I study has been performed in healthy volunteers:

Methods and Materials—Example 3

Six healthy volunteers (male, caucasian—18-45 years old) were recruited from the GCP-Galmed clinical centre. All healthy volunteers provided written informed consent prior to study participation. The study was approved by the independent Ethical Committee.

All volunteers were orally administered 2, 4, 6, 8, 10 and 12 grams of CHP with a wash out period of at least one week between doses of CHP.

The following blood and urine samples were collected for determination of the pharmacokinetics parameters of CHP and THP:

10 hours and immediately prior to administration of CHP (0 Hour), and at 0.25, 0.5, 1, 1.5, 2, 2.5, 3, 4, 5, 6, 12 and 24 hours after administration of CHP.

Urine was collected for the determination of the CHP and THP concentrations and the calculation of the elimination parameters of CHP and THP.

Example 4—Study Title: Single Dose Absolute Bioavailability (Intravenous IV Solution) and Safety Study of CHP in Healthy Volunteers-GALMED Study No: 0302-72—Results (FIGS. 5 and 6)

According to example 4 in this invention, the following ICH-GCP Clinical Phase I study has been performed in healthy volunteers:

Methods and Materials—Example 4

Six healthy volunteers (male, caucasian—18-45 years old) were recruited from the GCP-Galmed clinical centre. All healthy volunteers provided written informed consent prior to study participation. The study was approved by the independent Ethical Committee. Single doses of CHP were intravenously administered: 2.0 g, 4.0 g (2×2.0 g). Each dose level was administered to all healthy volunteers. There was a washout period of at least one week between doses.

Results from Example 3 and 4

Absorption, Distribution and Excretion of CHP in Healthy Subjects Following Oral Application (Examples 3 and 4)

Surprisingly and unexpected according to the examples 3 and 4 in this invention that CHP has shown dose linearity correlations for the pharmacokinetic parameters AUC, and Cmax for a broad range of doses 2 g-12 g.

1. Cis 4-Hydroxy-L-Proline (CHP) dose linearity correlations after oral administration of CHP (2 g-12 g) in healthy subjects
2. Cmax and CHP dose have shown dose linearity.
3. AUC(0-∞) and CHP dose have shown dose linearity
4. Cmax correlates linear with AUC(0-∞) accordingly.
5. Tmax averaged 1.24 h, with a standard deviation of 0.22 h (coefficient of variation 17.8%). There is a slight positive correlation between Tmax and CHP dose.
6. Elimination half life of CHP averaged 3.70 h, with a low standard deviation of 0.41 h (coefficient of variation: 10.9%). There is a slight positive correlation between elimination half life and CHP dose. However the range (1.02 h) is similar to the standard deviations (average: 0.58 h).
7. Volume of distribution of CHP averaged 63.94 l, with a low standard deviation of 10.73 l (coefficient of variation: 16.8%). There is a slight positive correlation between volume of distribution and CHP dose.
8. Mean residence time (MRT) of CHP averaged 4.15 h, with a low standard deviation of 0.26 h (coefficient of variance: 6.2%).
9. Oral clearance of CHP averaged 199.72 ml/min, with a low standard deviation of 12.05 ml/min (coefficient of variance: 6.0%).
10. Metabolism of CHP: The liver microsomal enzyme system metabolizes cis-4-Hydroxy-L-proline (CHP), cis 4-involving isomerisation, hydroxylation and demethylation Absorption, Distribution and Excretion of THP in Healthy Subjects (Examples 3 and 4)

Surprisingly and unexpected according to the examples in this invention that THP has shown dose linearity correlations for the pharmacokinetic parameters AUC, and Cmax following the administration of for a broad range of CHP doses 2 g-12 g.

1. Trans 4-Hydroxy-L-Proline (THP) dose linear correlations after oral administration of CHP (2 g-12 g) in healthy subjects
2. Cmax and THP have shown dose linearity.
3. AUC(0-∞) and THP have shown dose linearity
4. Cmax correlates linear with AUC(0-∞) accordingly.
5. $T_{max}$ averaged 4.92 h, with a low standard deviation of 0.51 h (coefficient of variation: 10.4%)
6. Volume of distribution of THP averaged 804.70 l, with a standard deviation of 202.91 l (coefficient of variation: 25.2%).
7. Oral clearance of THP averaged 798.42 ml/min, with a standard deviation of 192.68 m f/min (coefficient of variation: 24.1%).
8. Tmax of THP averaged 4.92 h, with a low standard deviation of 0.51 h (coefficient of variation: 10.4%).
9. Elimination half life of THP averaged 14.81 h, with a low standard deviation of 1.94 h (coefficient of variation: 13.1%).
10. Mean residence time of THP averaged 23.24 h, with a low standard deviation of 2.54 h (coefficient of variation: 10.93%).

Safety Data from Example 3 and 4

The following safety parameters were determined at the pre- and post-study examinations:
1. Vital signs
2. Clinical laboratory: Blood chemistry, Haematology, Coagulation, Urinalysis
3. Adverse events (Signs and Symptoms) have been recorded in each of the two treatment periods.

Based on the parameters and findings mentioned above, the following could be stated on the safety of CHP administered orally and intravenously to healthy volunteers:

Vital parameters, clinical chemistry, haematological and urinalysis findings were all within the normal range.

Example 5—Study Title: Multiple Dose Ascending Bioavailability and Safety Study Phase 1 with Oral CHP-GALMED Study No: 0202-71

According to this example in this invention, the following ICH-GCP Clinical Phase I study has been performed in healthy volunteers:

12 healthy Caucasian males were recruited (age: 18-45 years).

Multiple doses of CHP were orally administered:
4×2.0 g CHP per day, for 14 consecutive days (total daily dose=8.0 g CHP)
4×3.0 g CHP per day, for 14 consecutive days (total daily dose=12.0 g CHP) Each dose level was administered to all volunteers.

Objectives

To determine the pharmacokinetic parameters and safety of CHP and THP in plasma following oral administration of multiple doses of 8 g CHP (4×2 g) and 12 g CHP (4×3 g)—4× daily, τ=6 h, respectively, in 12 healthy subjects on Day 1 and Day 14.

To model and simulate plasma concentrations of CHP and THP during Days 1 to 14.

Results from Example 5 and Discussion:

Below are the relevant generated pharmacokinetic parameter for CHP and THP.

Pharmacokinetics of CHP (4×2.0 g CHP/day)
$C_{max}$ (µg/ml) 52.33+/−10.71
$t_{max\,(h)}$ 0.98+/−0.27
$t_{1/2\,(h)}$ 34.25+/−19.71
MRT (0-inf) h 9.33+/−3.96

Pharmacokinetics of THP (4×2.0 g CHP/Day)
$C_{max}$ (µg/ml) 9.56+/−2.23
$t_{max(h)}$ 1.50+/−0.59
$t_{1/2\,(h)}$ 12.40+/−5.28
MRT (0-inf) h 19.13+/−4.71

Conclusion on the Pharmacokinetics of CHP and THP Following the Multiple Dose of Oral CHP 1. Surprisingly and unexpected that the pharmacokinetic parameters of CHP and THP have shown relatively low interpatients-variability although the patients were under treatment with other medications e.g for diabetes, hypertension, analgetic drugs . . . etc. This is an advantage for the adjustment of the dose and the optimisation of the treatment scheme using CHP. In addition it is indicative for lack of drug-drug interactions of CHP with the other concomitant medications especially by elderly patients.
2. Surprisingly and unexpected that the plasma half-life of CHP was long (34.25+/−19.71 h) and the accumulation of CHP became extensive following oral administration. Accumulation of THP also reached a remarkable extent. This will have positive impact on the accelerated efficacy of CHP and THP.
3. In addition surprisingly and unexpected that after approximately 48 h and 96 h, a steady state was observed for CHP and THP, respectively.
4. Surprisingly and unexpected that the CHP blood level required for prevention, attenuation, therapy, diagnosis follow-up, and/or aftercare of said dementia, Alzheimer's, neurodegenerative diseases, and neuromuscular degenerative disorders could be achieved by the administration of the different pharmaceutical formulations of CHP formulations according to this invention. In addition the treatment could be adjusted using the Propylactic and/or Therapeutic Drug Monitoring PDM/TDM following the determination of CHP and THP using a sensitive and selective HPLC or ELISA assay for CHP with or without THP as biomarkers.

5. Surprisingly and unexpected that the prophylactic CHP-level in blood (>endogenous plasma level for the individual patients) has been achieved by the administration of low dose of oral CHP (=/>50 mg as multiple dose).

6. The pharmacokinetic parameters AUCss, t, Css, max and Css, ave for CHP and THP were increased by approximately 50% when the administered dose was increased from 2.0 g up to 3.0 g (administration 4× daily).

7. The median times to reach peak plasma CHP and THP concentration, tss, max, were the same for the two respective treatments. Css, min of CHP and THP was 36 and 24% lower, respectively, if 2.0 g of CHP was administered. This is indicative of dose-proportional characteristics.

8. The plasma half-life of CHP was approximately 4 times higher than the dosing interval, accumulation of CHP became extensive following oral administration. Accumulation of THP also reached a remarkable extent.

9. In addition surprisingly and unexpected the simulation of plasma concentration-time curves of CHP and THP up to 19 days after administration was achieved with reasonable quality especially with regard to CHP. After approximately 48 h and 96 h, a steady state was observed for CHP and THP, respectively.

Figure 7:
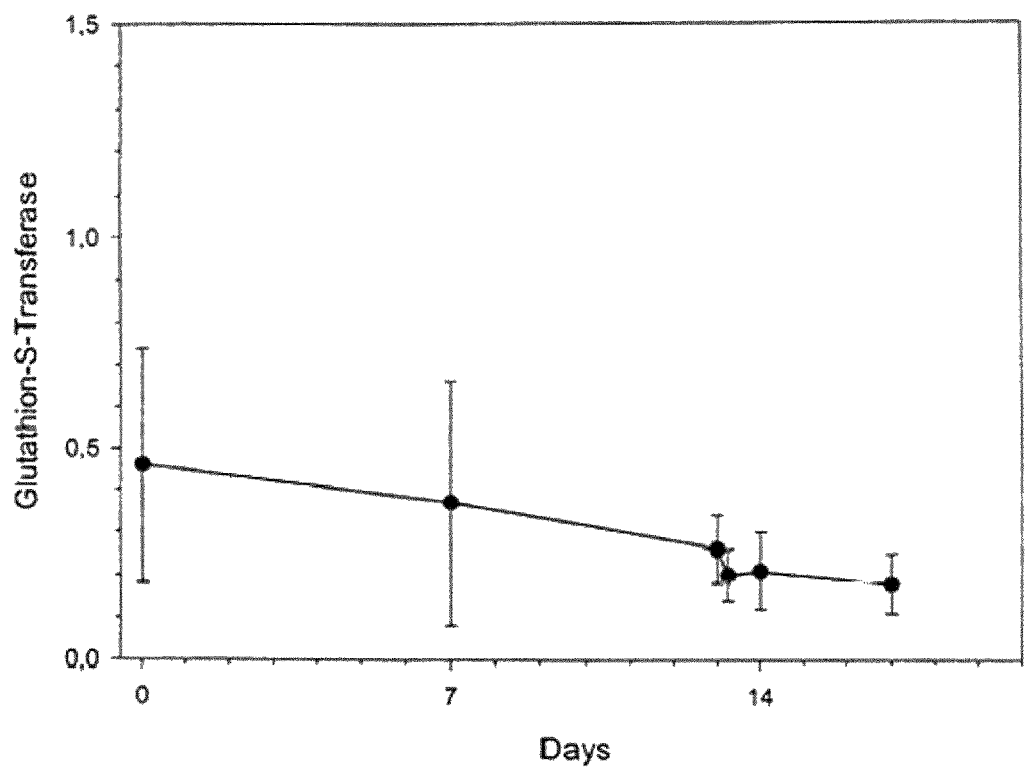
FIG. 7: Means and standard deviations of Glutathione-S-Transferase after administration of CHP (4×2.0 g CHP/day; 14 days)—(Study 0202-71).

Example 6—Measurement of α-Glutathione-S-Transferase Following Multiple Dose Administration of CHP (Study 0202-71)—(FIG. 7)

Study title: Measurement of α-Glutathione-S-Transferase following multiple dose administration of CHP (Study 0202-71)

According to the examples in this invention, the following ICH-GCP Clinical Phase I study has been performed in healthy volunteers:

12 healthy Caucasian males were recruited (age: 18-45 years). Multiple doses of CHP were orally administered:

4×2.0 g CHP per day, for 14 consecutive days (total daily dose=8.0 g CHP)

4×3.0 g CHP per day, for 14 consecutive days (total daily dose=12.0 g CHP)

Each dose level was administered to all volunteers.

Objectives

To determine the effect of CHP on the blood concentration of Alpha Glutathione S-Transferase (α-GST) following the administration of:

4×2.0 g CHP per day, for 14 consecutive days (total daily dose=8.0 g CHP)

4×3.0 g CHP per day, for 14 consecutive days (total daily dose=12.0 g CHP)

Each dose level was administered to all volunteers.

Results and Discussion

Surprisingly and unexpected that CHP inhibits significantly the α-GST levels in blood of the healthy volunteers. The results of estimation of α-GST levels are shown in FIG. 7.

The decrease in α-GST levels observed was found to be highly significant. The P-value obtained was 0.0017, indicating a 99.8% that the decreased observed was not the result of chance. A one-sample two-sided t-test was used, using the data from day 0-day 17.

There is no effect of liver cell damage caused by CHP.

Glutathione-S-transferase (GST) molecules bind oncogenes and/or parts of the tumour cells with Glutathione in order to prepare them for the extracellular transport, an inhibition of GST could lead to decrease of a tumor-cell spreading-effect, resulting in the reduced formation of metastases. Because of increased binding of GSH, it cannot be used for other intracellular purposes, which leads to an intoxication of the cell. The binding to parts of the tumour cell might lead to transformed information in the cell resulting in its dysfunction.

Figure 8:
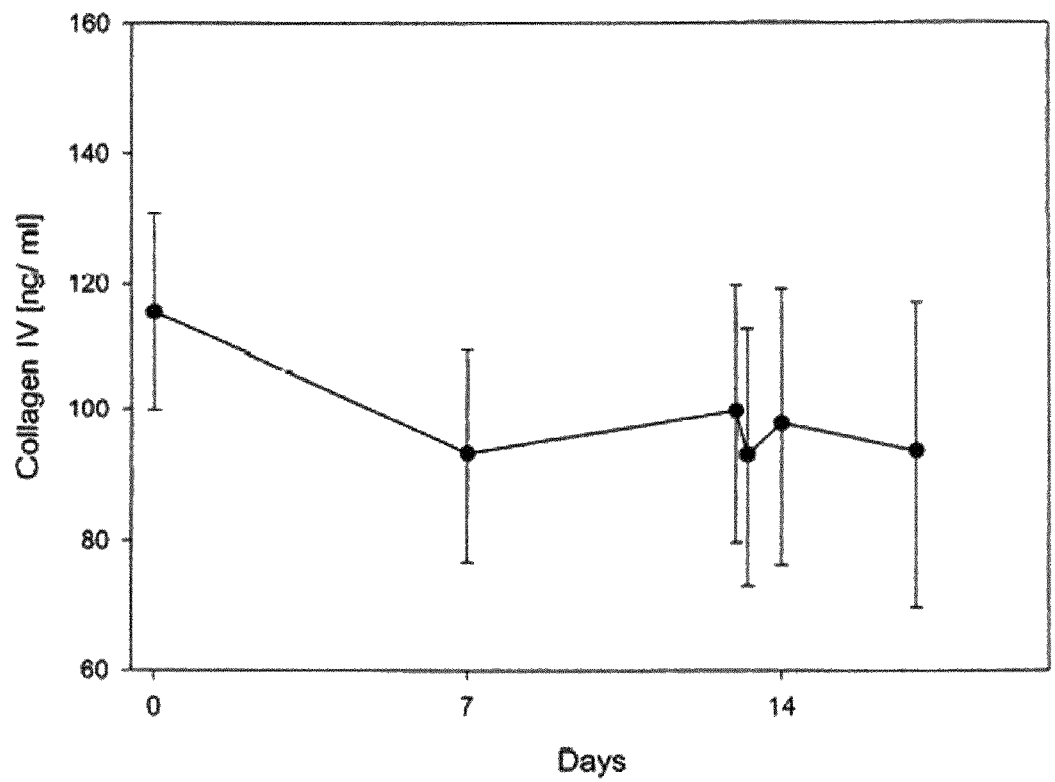
FIG. 8: Means and standard deviations of Collagen IV after administration of CHP (4×2.0 g CHP/day; 14 days)—(Study 0202-71)
Figure 9:
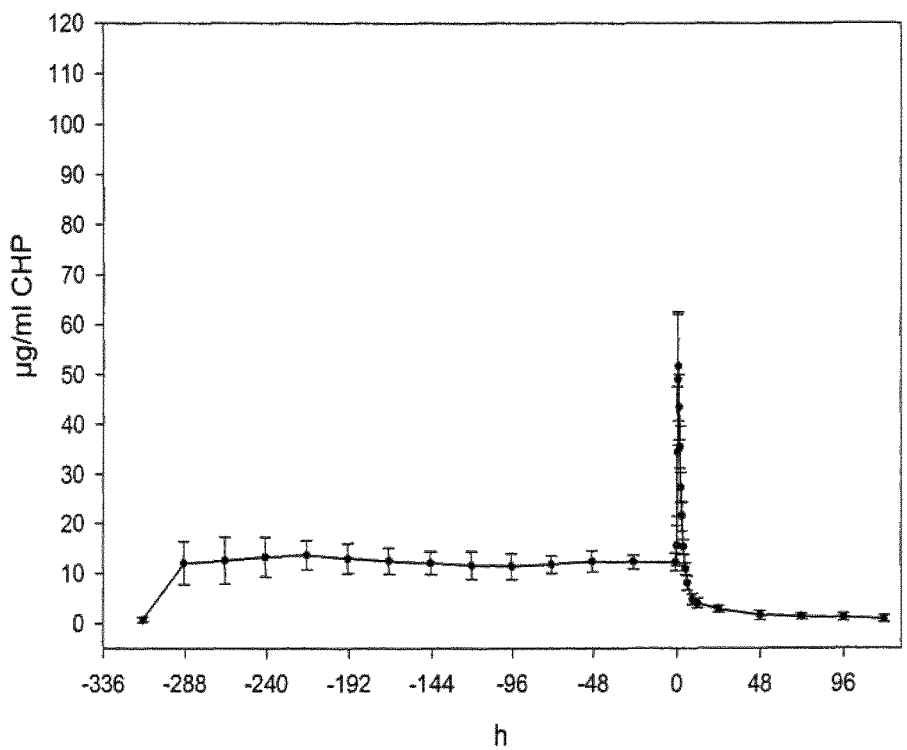
FIG. 9: Means and standard deviations of CHP plasma concentrations following the administration of (4×.2.0 g CHP/day over 14 consecutive days, n=12)
Figure 10:
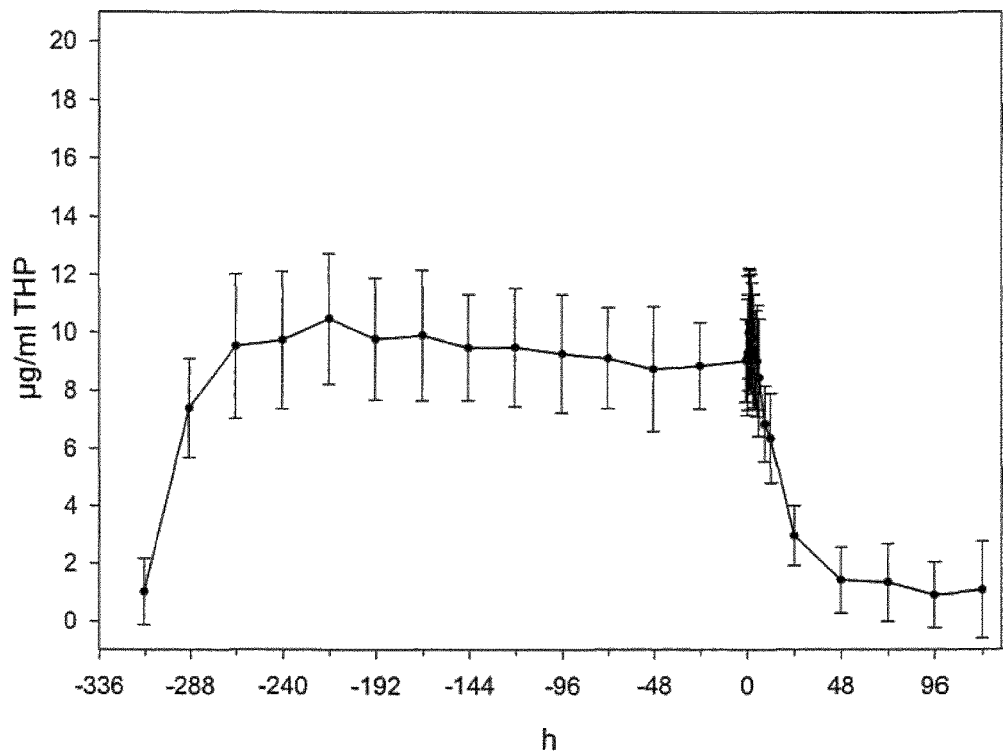
FIG. 10: Means and standard deviations of THP plasma concentrations following the administration of (4×.2.0 g CHP/day over 14 consecutive days, n=12)

Example 7—Study Title: Measurement of Collagen-IV Following Multiple Dose Administration of CHP-Study 0202-71—(FIG. 8)

Results from Example 7 and Discussion

Surprisingly and unexpected that CHP inhibits significantly the collagen IV levels in blood of the healthy volunteers.

The decrease in Collagen-IV levels observed was found to be highly significant. Using a one-sample two-sided t-test, a P-value of 0.0016 was obtained, indicating a 99.8% that the decreased observed was not the result of chance. Using a one-sample two-sided Wilcoxon-test, a P-value of 0.0047 was obtained, indicating a 99.5% that the decreased observed was not the result of chance.

Collagen IV forms the framework of basement membranes and is one of the earliest components to be deposited during their development. In healthy livers, collagen IV is restricted to the periportal region, but with the development of liver fibrosis, it is deposited throughout the liver lobule.

Serum collagen IV levels correlate with the extent of collagen IV deposition in the liver, and increased serum levels seem to indicate that active fibrosis is occurring. Collagen IV might be a valuable biomarker of Alzheimer's disease and neurodegenerative diseases due to the fibrotic process in the brain tissues.

It will be assumed a direct correlation between the blood level of collagen IV and the formation and/or progression of Alzheimer's disease.

Collagen IV is a more relevant analyte than the chemical markers tested routinely. It offers new possibilities in stratifying patients and in monitoring therapy and recovery.

Figure 11:
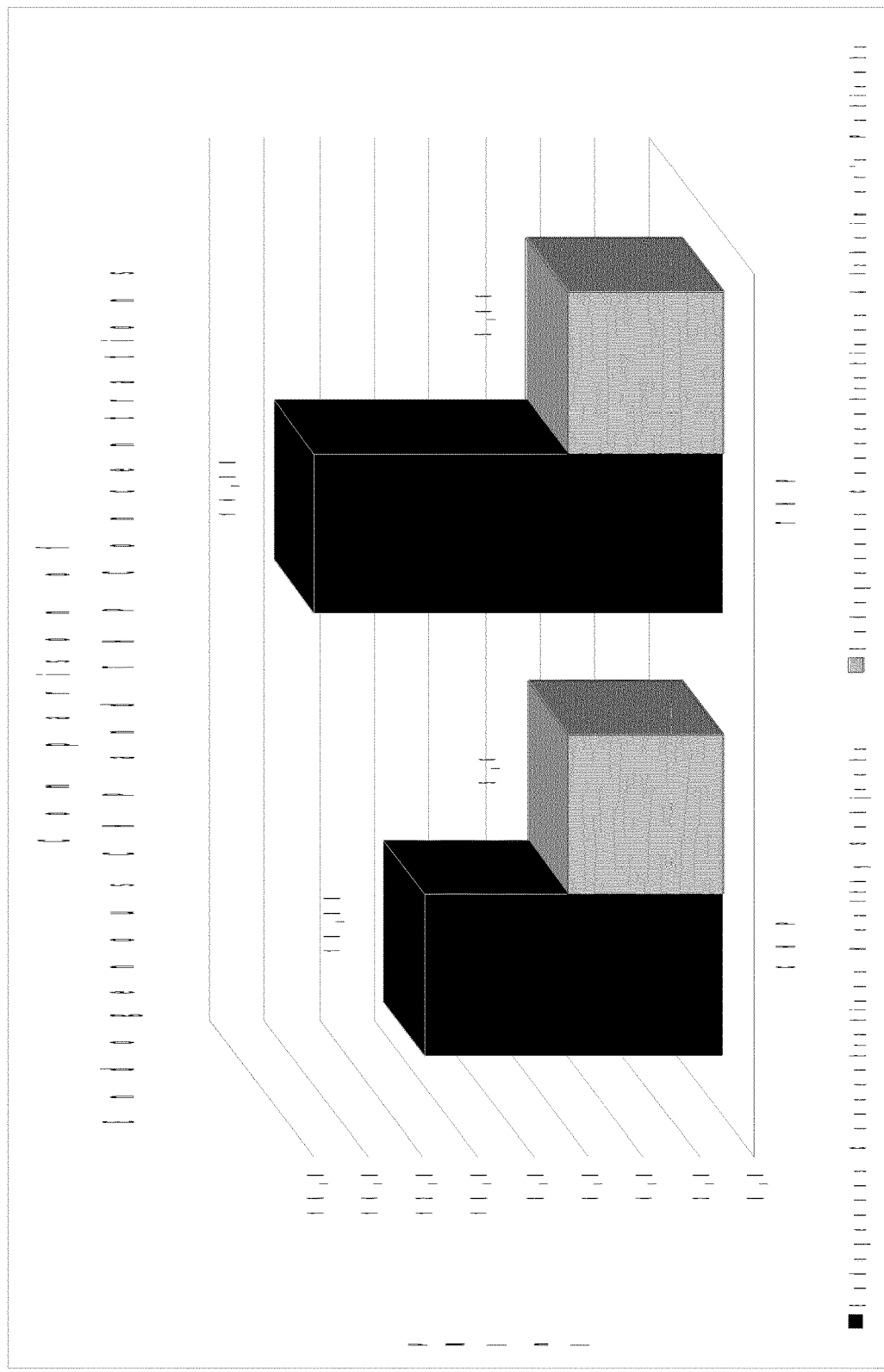
FIG. 11: Comparison of endogenous CHP and THP plasma/blood concentrations in healthy subjects and Alzheimers patients
Figure 12:
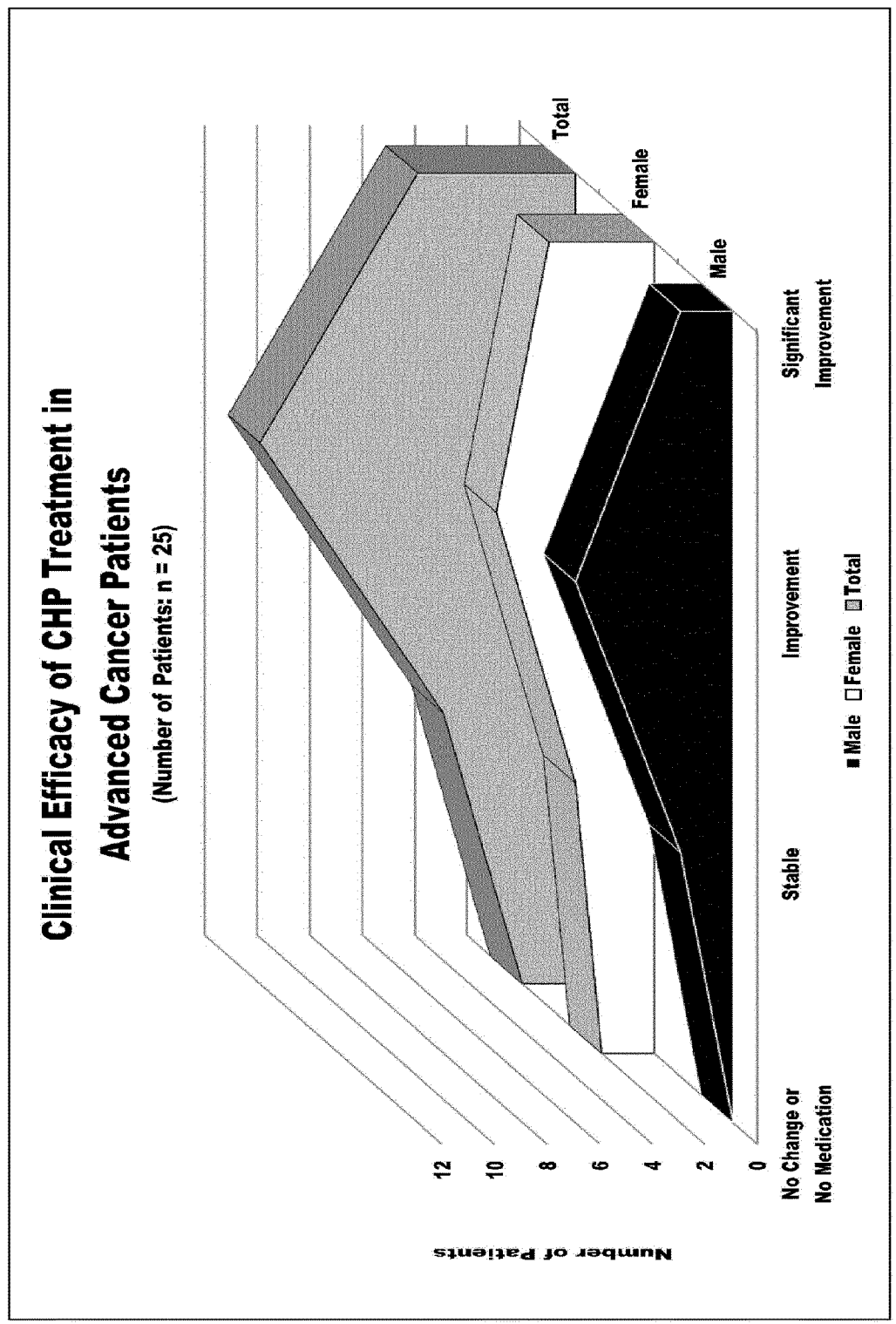
FIG. 12: Clinical efficacy of CHP treatment in advanced cancer patient FIG. 13.1: CHP treatment—mild Alzheimer subjective assessments; Overall physical conditions FIG. 13.2 CHP treatment—mild Alzheimer subjective assessments; Cognitive conditions FIG. 13.3: CHP treatment—mild Alzheimer subjective assessments; Quality of Life (QoL)

Example 8—Study Title: Determination of Pre-Dose Endogenous Concentrations of CHP in Healthy Volunteers (Study 0202 71) (FIG. 11)

According to the examples in this invention, the following ICH-GCP Clinical Phase I study has been performed in healthy subjects for the assessment of the pharmacokinetic profiles of CHP and THP and the determination of the pre-dose endogenous CHP blood plasma concentrations, which were measured for all healthy volunteers directly before CHP administration using a validated, sensitive and selective HPLC bioanalytical method. This was performed prior to all CHP administrations (i.e. for 2.0 g and 3.0 g).

The mean endogenous CHP concentration in healthy subjects, calculated across all dose groups, was 0.71±0.56 μg CHP/ml of plasma.

24 readings were taken in total.

Concentration of CHP in blood is approximately 2-fold the concentration in plasma (plasma makes up about 50-55% of the overall content of blood), thus 1.420±1.12 μg CHP/ml blood, which is equivalent to 10.834±8.54 μM CHP/ml blood This compares to an average $C_{max}$ of 30.29±13.91 μg CHP/ml plasma, equivalent to 462.2±212.1 μM CHP/ml blood.

As a percentage of the average $C_{max}$, the pre-dose endogenous concentration was $$2.3\% \pm 1.9\% \left(\frac{0.71}{30.29} \pm \frac{0.56}{30.29}\right).$$

Example 9—Study Title: Determination of Pre-Dose Endogenous Concentrations of THP in Healthy Volunteers (Study 0202 71)—(FIG. 11)

According to the examples in this invention, the following ICH-GCP Clinical Phase I study has been performed in healthy volunteers for the assessment of the pharmacokinetic profiles of THP and to determine the pre-dose endogenous THP plasma concentrations, which were measured for all healthy volunteers directly before CHP administration using a validated, sensitive and selective HPLC bioanalytical method. This was performed before both CHP administrations (i.e. for 2.0 g and 3.0 g).

The mean endogenous THP concentration in healthy subjects, calculated across all dose groups, was 0.97±1.15 μg CHP/ml of plasma. 24 readings were taken in total.

Concentration of THP in blood is approximately 2-fold the concentration in plasma (plasma makes up about 50-55% of the overall content of blood), thus 1.94±2.3 μg THP/ml blood, which is equivalent to 14.80±17.5 μM THP/ml blood.

As a percentage of the average $C_{max}$, the pre-dose endogenous concentration was 8.1%±9.6%.

Example 10—Comparisons Between the Pathological Endogenous Blood Concentrations of CHP and THP in Patients with Alzheimer's Disease (AD) with the Normal Concentrations in Healthy Subjects Summary of the Data of Endogenous Concentrations of CHP and THP in Blood and Biological Samples of Alzheimer's Patients and Healthy Subjects Collected in the Examples of this Invention:

Cis 4-Hydroxy-L-Proline (CHP)

The following pathological endogenous CHP (cis 4-Hydroxy-L-proline) concentrations have been detected and quantified in patients with Alzheimer's disease:

Blood: Gender: Both, Age: Adult (>18 years old), Value: 5.6±0.7 μM CHP/ml blood

Cerebrospinal Fluid (CSF): Gender: Both, Age: Adult (>18 years old). Value: 2.8±0.6 μM CHP/ml CSF.

The following normal endogenous CHP (cis 4-Hydroxy-L-proline) concentration has been detected in healthy male subjects:

Blood: Gender: Both, Age: Adult (>18 years old), Value: 10.8±8.5 μM CHP/ml blood Conclusion: Surprisingly and unexpectedly Alzheimer's patients are suffering from a serious deficiency of endogenous CHP in blood and biological materials. The mean endogenous concentration of cis 4-Hydroxy-L-proline (CHP) in blood of patients with Alzheimer's disease is 5.6 μM CHP/ml blood. Compared to the concentration found in healthy subjects of 10.8 μM CHP/ml blood, this is equivalent to a decrease of 48.1%.

Trans 4-Hydroxy-L-proline (THP)

The following pathological endogenous concentrations of THP (trans 4-Hydroxy-L-proline) have been detected and quantified in patients with Alzheimer's disease.

Blood: Gender: Both, Age: Adult (>65 years old), Value: 5.66±0.7 μM THP/ml blood The following normal endogenous THP (trans 4-Hydroxy-L-proline) concentrations have been detected and quantified in healthy human subjects:

Blood (Own Results, Ref. "Example 9")

Gender: Both, Age: Adult (>18 years old), Value: 14.8±17.5 μM THP/ml blood

Blood (Published Results from Other Sources)

Gender: Male, Age: Adult (>18 years old), Value: 20.0±11.0 μM THP/ml blood

Gender: Female, Age: Adult (>18 years old), Value: 16.0±9 μM THP/ml blood

Conclusion

Since the THP concentration in healthy subjects as well as the gender differences reported in the external published data are relatively low, we base our further evaluation solely on our own data. Surprisingly and unexpectedly Alzheimer's patients are suffering from a serious deficiency of THP in blood and biological materials. The mean endogenous concentration of trans 4-Hydroxy-L-proline (THP) in blood of patients with Alzheimer's disease is 5.66 μM THP/ml blood. Compared to the concentration found in healthy subjects of 14.8 μM THP/ml blood, this is equivalent to a decrease of 61.8%.

Summary of the Abnormal and Pathological Endogenous Blood Concentrations of CHP and THP in Patients with Alzheimer's Disease (AD) in Comparison with Healthy Subjects (FIG. 11)

1. The endogenous concentration of CHP (cis 4-Hydroxy-L-prolin) in blood of healthy subjects is 10.8 μM CHP/ml blood, in patients with Alzheimer's disease this concentration is 5.6 μM CHP/ml blood, equivalent to a decrease of 48.1%. (FIG. 11).
2. The endogenous concentration of THP (trans 4-Hydroxy-L-prolin) in blood of healthy subjects is 14.8 μM THP/ml blood, in patients with Alzheimer's disease this concentration is 5.7 μM THP/ml blood, equivalent to a decrease of 61.8%. (FIG. 11)

Consequences of cis 4-hydroxy-I-proline (chp) and trans4-hydroxy-I-proline (thp) deficiencies in the blood of alzheimer's patients:

Substances that traverse the walls of brain capillaries must move through the endothelial cell membranes. Accordingly, molecular entry into the brain should be determined by an agent's solubility in lipids, the major constituent of cell membranes. Nevertheless, many ions and molecules not readily soluble in lipids do move quite readily from the vascular space into brain tissue. A molecule like glucose, the primary source of metabolic energy for neurons and glial cells, is an obvious example. This paradox is explained by the presence of specific transporters for glucose and other critical molecules and ions.

CHP has shown surprisingly and unexpected according to the examples 1 and 2 in this invention the following findings after the repeated dose administration of oral aqueous solution of $^3$H-CHP to the animals: 1. Excellent penetration of the BBB as the target for the effects of CHP in the brain CNS, and muscles High concentration and bioavailability in cerebrum, cerebelium, brain stem, limbic system and spinal fluid (14.9% AUC as % of total administered CHP) which will allow the prophylaxis, prevention, diagnosis, attenuation, therapy, follow-up and/or aftercare of said dementia, Alzheimer's and neudegenerative diseases. With regard to the high bioavailability and the tissue distribution of CHP in the brain it is relevant to consider the blood supply in the brain for the delivery and targeting of CHP to the tissues of interest.

Based on the surprisingly and unexpected results generated from the examples in this invention the inventor postulated that the serious deficiencies on the concentrations of CHP and THP in blood of Alzheimer's patients may have, but not limited to the following consequences:

The cells and tissues including the brain's tissues and the cerebrospinal fluid (CSF) of the human subject will not be supplied with the sufficient physiological amounts of CHP and THP required for the maintenance of the cellular and intracellular mechanisms and the prevention of the accumulation of cross-linked protein damages cells and tissues.

Accordingly the multi pharmacological effects and functions of CHP and THP in the body will be dysregulated, and therefore this will cause a number of disorders e.g. protein misfolding (proteopathy), senile plaques, and tauopathy. These cellular and intracellular disorders and molecular damages in the brain/CNS may cause the Alzheimer's Disease (AD), dementia and/or other neurodegenerative diseases.

Example 11—Study Title: Evaluation of the Efficacy, Safety and Quality of Life (QoL) of 25 Clinical Cases in Patients with Advanced Cancer Disease Treated with Oral and Intravenous Formulations of Cis-4-Hydroxy-L-Proline (CHP)

25 patients (15 female and 10 male) have been treated with oral and/or intravenous CHP:
Mean age was over 60 years with maximum of 82 and minimum of 36 years.
15 Patients considered as "elderly patients"—60-82 years (60%)
Patients 50-60 years (20%)
No further demographic data were documented.
Complete clinical case documents have been prepared for each patient.

TABLE 1

Quality of Life Data for all 25 patients involved in study on CHP

| Patient Number | Gender | Age | Quality of Life (QoL) |
|---|---|---|---|
| 1 | Male | 73 | Significant improvement |
| 2 | Male | 52 | Improvement |
| 3 | Female | 50 | Significant improvement |
| 4 | Female | 60 | Improvement |
| 5 | Male | 69 | Improvement |
| 6 | Female | 36 | Significant improvement |
| 7 | Female | 66 | Significant improvement |
| 8 | Female | 70 | Improvement |
| 9 | Female | 43 | No change |
| 10 | Male | 44 | Improvement |
| 11 | Male | 68 | Improvement |
| 12 | Male | 56 | Improvement |
| 13 | Female | 63 | Stable |
| 14 | Male | 38 | Stable |
| 15 | Male | 82 | Stable |
| 16 | Male | 67 | Significant improvement |
| 17 | Female | 59 | Significant improvement |
| 18 | Female | 49 | Didn't take medication |
| 19 | Male | 67 | Improvement |
| 20 | Female | 66 | Improvement |
| 21 | Female | 69 | Improvement |
| 22 | Female | 54 | Improvement |
| 23 | Female | 70 | Improvement |
| 24 | Female | 67 | Stable |
| 25 | Female | 64 | Stable |

Results on Safety, Toxicity and Quality of Life Following the Treatment with CHP
No deviations of clinical relevance were shown in safety parameters, by any patient.
No adverse events or side effects occurred were clinically relevant relating to toxicity parameters.
Quality of life was measured using a validated quality of life questionnaire.
Summary of the Results from Example 11
Surprisingly and unexpected that the long-term treatment (1-13 month) with high dose (2-22 gram/day) of CHP as monotherapy has been well tolerated In 25 patients no toxic side effects or serious adverse events have been recorded. Under therapy with CHP in oral and/or parenteral form there was significant improvement in Quality of Life for 18 patients (72%) who were examined with advanced cancer. 11 of these patients were elderly patients (over 60 years) These patients managed and/or experienced the following physical and mental improvements:
Going back to work, Doing house work, Experiencing hobbies, Going on holidays, Pain relief, Improved appetite, Gain of weight
Also most of the patients showed a quite long time of stable disease (meaning no progression, no ascites, no obstruction, no extremely increased level of pain) keeping in mind their advanced disease. Patients who showed tumour progress, probably because of a delay in starting the treatment, not taking the medication (patient No 18) or because the disease itself was too advanced. In one case healing was achieved. According to the examples of this invention, this was surprisingly and unexpected enormous success.

Example 12 (Includes the Summary of the Phase II Clinical Studies 1-4)

According to the example No. 12 in this invention, the safety, efficacy and Quality of Life (QoL) of CHP as monotherapy have been investigated in patients suffering from cancer, chronic liver diseases (liver fibrosis) and mild Alzheimer's disease/dementia The following four (4) ICH-GCP
Phase II-Ill clinical studies in this invention have been performed in GCP certified clinical centres in Germany and other European countries.

Title: Phase II—CHP as antitumour agent in patients with resected colorectal cancer and liver metastasis; 60 patients—Study IPSS-A04 (Example 12.1).

Title: Phase II—CHP in patients with locally advanced or metastatic pancreatic cancer—14 patients Study IPSS B013 (Example 12.2).

Title: Evaluation of safety and efficacy of CHP in patients with urogenital Cancer—25 patients—Study IPSS-D002 (Example 12.3).

Title: Phase II—CHP in patients with chronic viral hepatitis, chronic alcohol liver diseases without cirrhosis or primary sclerosing cholangitis 45 patients—Study IPSS-B025 (Example 12.4).

Objectives of the ICH-GCP Clinical Studies (Example 12.1-12.4))

According to the examples in this invention, the objectives of these studies were:

Assessment the efficacy and safety of CHP as monotherapy have been investigated in patients suffering from cancer, chronic liver diseases (liver fibrosis) and mild Alzheimer's disease/dementia.

The following validated evaluation systems have been used:
1. Evaluation of Quality of Life as measured by the FACT questionnaires.
2. Evaluation of the toxicity and safety of CHP treatment as measured by the Common Toxicity Criteria CTC.
   Subjective assessments mild Alzheimer' patients: Overall physical conditions, Cognitive conditions, Quality of Life (QoL)

Target Parameters:
0. Quality of Life
1. Evaluation of toxicity and safety
2. Occurrence of clinical adverse events
3. Safety laboratory blood and urine parameters:
4. Haematological, biochemical, and selected immune functions
5. Liver enzyme parameters: GOT, GPT, γ-GT, LAP and AP (alkaline phosphatase)
6. Kidney function:
7. Creatinine, urea, uric Acid
8. Pharmacokinetic parameters of CHP Surprisingly and unexpected that CHP has shown in the ICH-GCP clinical studies IPSS-A04, IPSS-B013, and IPSS-D002 anti-tumour activities in patients suffering from adenocarcinoma and liver metastases, pancreatic cancer and bladder cancer.

It is also surprisingly and unexpected that CHP has shown in the study IPSS-B025-anti-fibrotic efficacy in patients suffering from chronic liver diseases. These results are very relevant for the purpose of this invention for the use of CHP as one the compounds of this invention for the prophylaxis, prevention attenuation, therapy, of said dementia, neurodegenerative disorders, Alzheimer's disease and/or neuromuscular diseases.

It is surprisingly and unexpected that in addition to the antitumour, antimetastasis and anti-angiogenesis activities of CHP shown in the examples 23-27 (clinical studies IPSS-A04, IPSS-B013, and IPSS-D002) in this invention, that CHP have shown as well anti-fibrotic activities in the clinical study (IPSS-B025-L).

Accordingly, It is also surprisingly and unexpected that CHP may inhibit the fibrillar amyloid plaques, the formation and deposits of beta-amyloid fragment, and the sanile plague in the brain which may be responsible for the cause of dementia and Alzheimer's disease.

It is also surprisingly and unexpected that CHP have shown in all clinical studies excellent tolerability although most of the patients were elderly and over 60 years old. According to the study protocols for the performance of these studies, oral and intravenous CHP as monotherapy have been administered to the patients at high doses e.g. 8 gram/day for approximately 180 consecutive days. A number of patients have received the medication for approximately 18 months as mono therapy.

Only mild side effects such as nausea and/or vomiting have been observed.

It is also surprisingly and unexpected that according to the evaluation of the toxicity and safety as measured by the Common Toxicity Criteria CTC, cis-4-hydroxy-I-proline (CHP) has not cause any nephrotoxicity, neurotoxicity, hepatotoxicity, cardiotoxicity and/or laboratory abnormalities. Vital parameters, clinical chemistry, haematological and urinalysis findings were in some cases marginally out of the normal range but were without clinical relevance. In addition no drug-drug interactions have been observed by the co-administration of CHP with drugs used by the patients (mostly elderly) for the different therapeutic indications.

In addition it is surprisingly and unexpected that according to the evaluation of the quality of life questionnaires, CHP has improved drastically the patients QoL. The majority of the patients (elderly) reported according to the QoL-questionnaires remarkable improvement of their mental and physical conditions.

Figure 13:
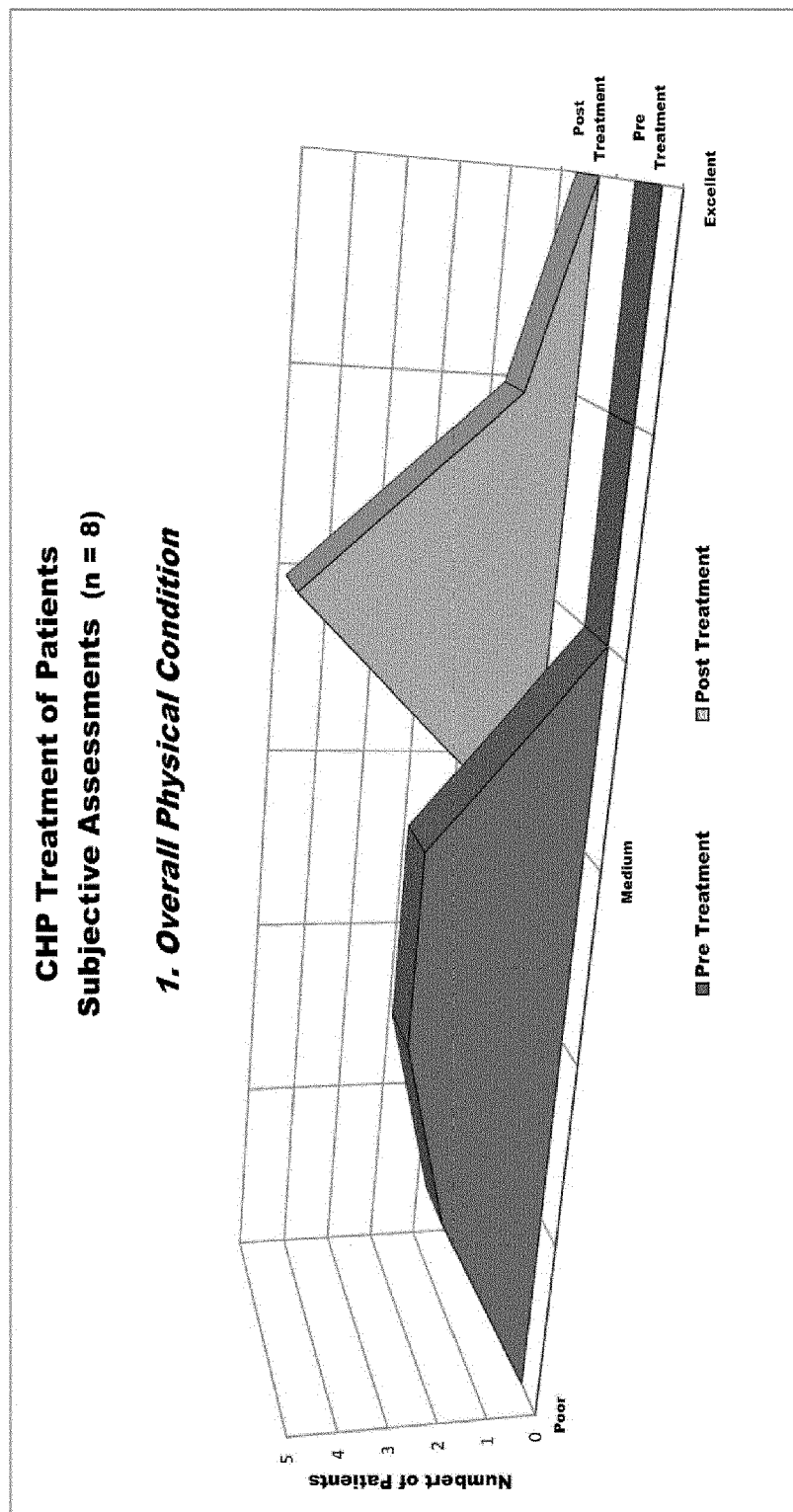
Figure 13:
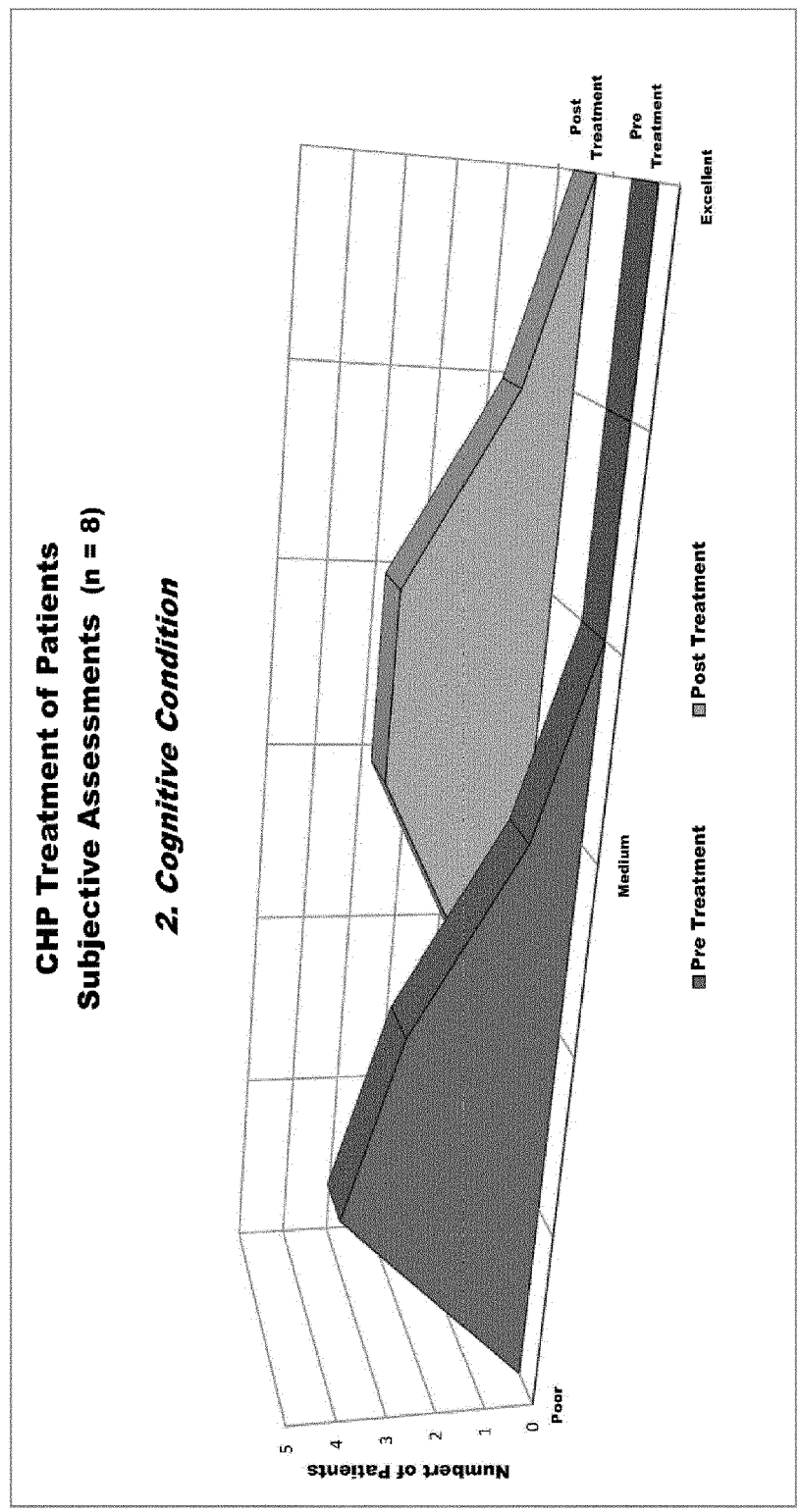
Figure 13:
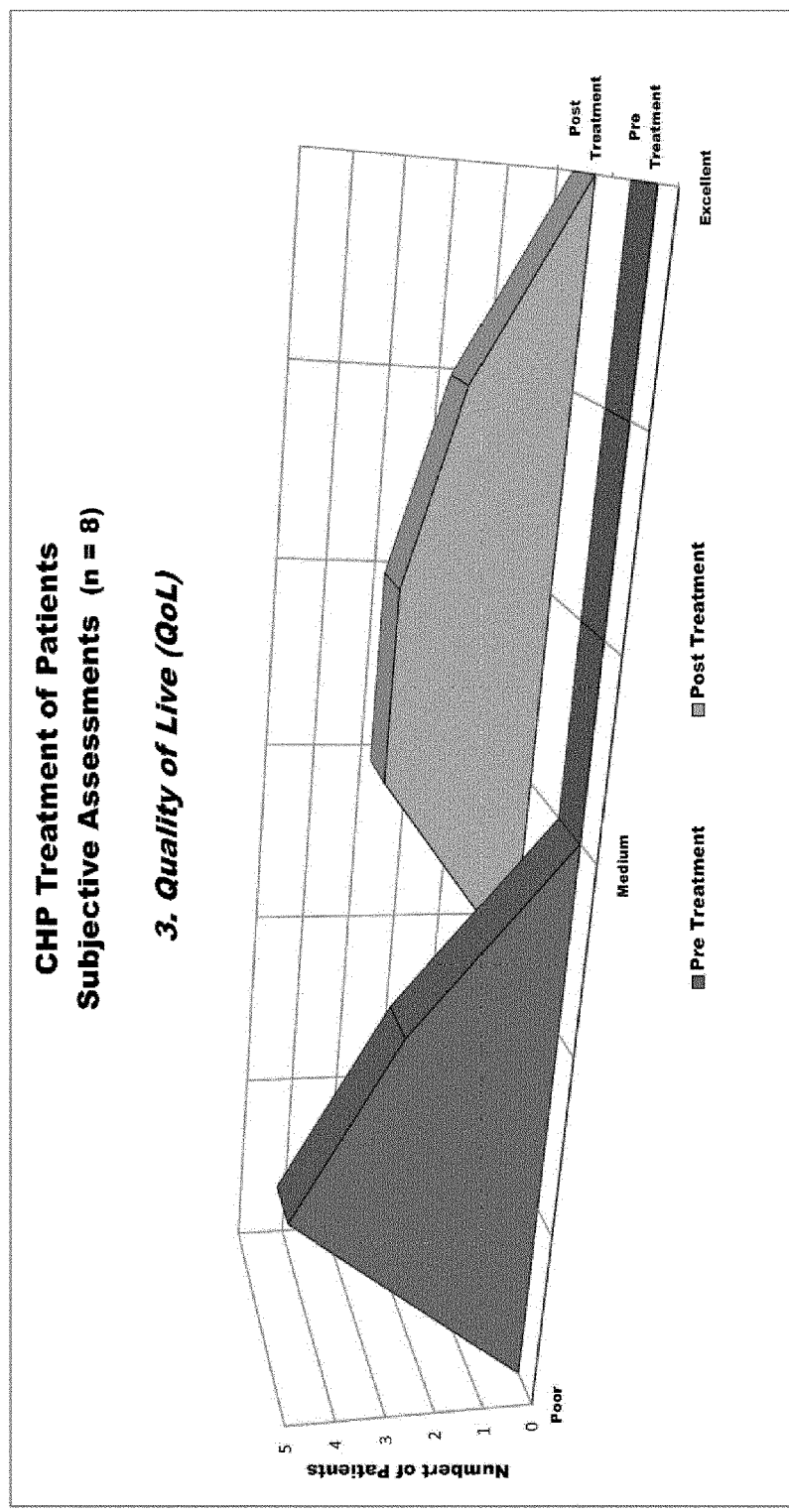
Figure 14:
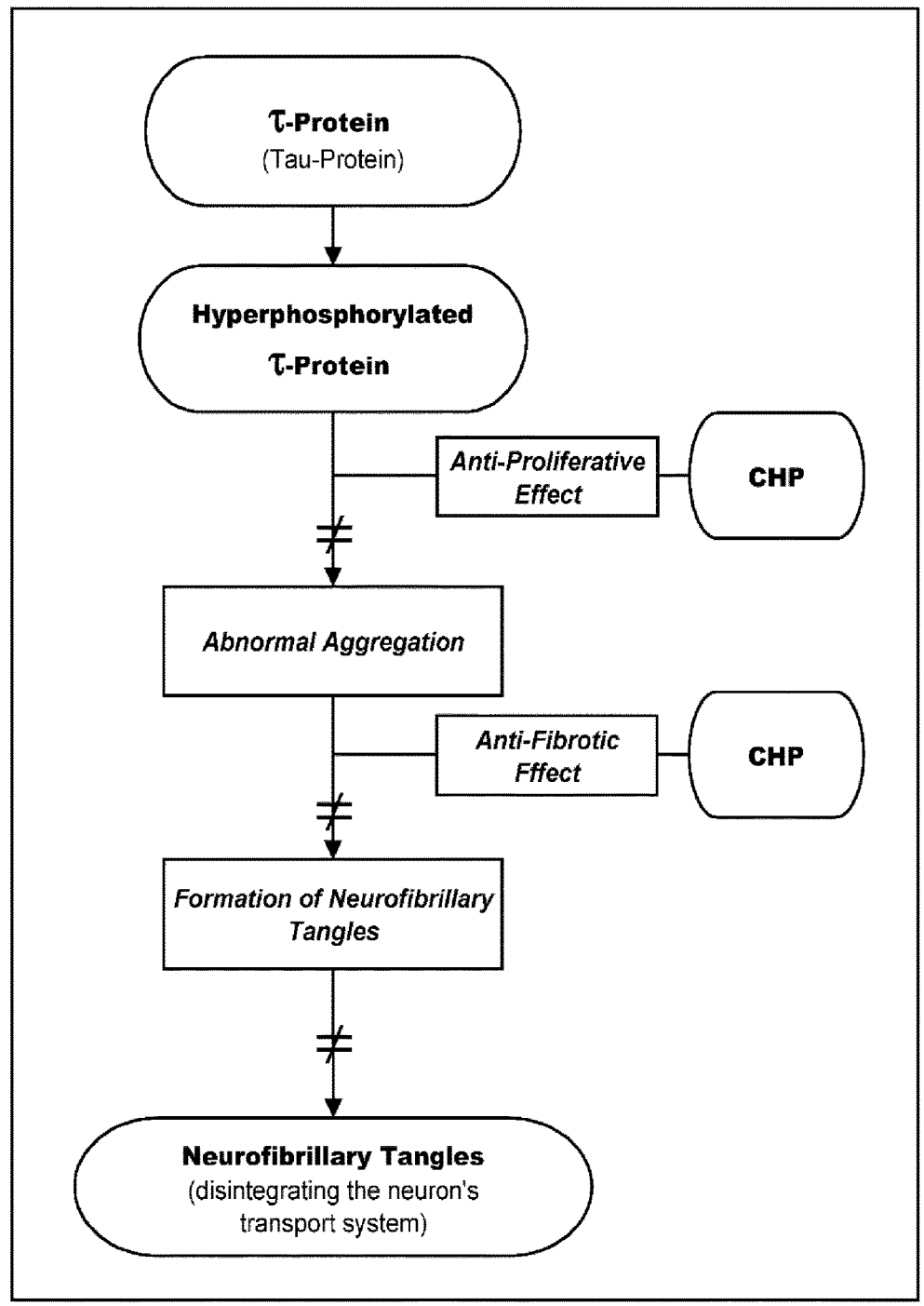
FIG. 14:1 and FIG. 14.2: Possible mode of action of cis-4-hydroxy-I-prolin (CHP) as multi-target agent for the prophylaxis and treatment of Alzheimer's Disease

Example 13—Physical, and Cognitive Conditions—Alzheimer—Dementia Measure and Quality of Life (QoL) (FIGS. 13.1, 13.2, 13.3)

According to the ICH-GCP requirements for assessment of the Quality of Life (QoL) the validated questionnaire related to the disease e.g. cancer have been administered in the Phase II clinical studies: IPSS-A04, according to the example 12.1 in this invention.

Additional developed modules to these questionnaire provided greater details on the particular aspects of quality of life for those patients who participated in these clinical studies and diagnosed with mild and moderate Alzheimer's disease based on the presence of neuropsychiatric symptoms.

Diagnosis begun with a thorough physical exam and complete medical history including cerebrovascular disease and supplemental information from family members. Simple tests of mental function, including word recall, object naming, and number symbol marching, were used to track changes in the patient's cognitive ability. Ruling out depression was part of the diagnosis. Eight (8) patients over the age of 65 years met these criteria and have been selected for the assessment of CHP effects on the quality of life according to the items mentioned below including the cognitive status.

The administration of intravenous (iv) and oral CHP as monotherapy has been scheduled according to examples 12.1 in this invention in the patient's group G2—in study IPSS-A04.

The assessment of the QoL, physical, and cognitive conditions—Alzheimer-Dementia has been completed by the patients/care providers in the following intervals (FIGS. 13.1-13.3):

Pre-dose: Prior to the start of treatment with CHP as monotherapy

Start and completion of treatment with CHP: The questionnaire has been completed every 4 weeks after the start of treatment (Week 4, 8, 12, 16, 20, 24) and 4 weeks upon the completion of the treatment with CHP as monotherapy. A scale value is given for each response that reflects a good quality of life. A value of one (1) is assigned to response that do not reflect a good quality of life. A higher score reflects a higher quality of life. The 5 domains of Quality of Life—Alzheimer's Disease-Dementia included are: 1. Enjoyment of activities, 2. Feelings and mood, 3. Awareness of self, 4. Social Interactions, 5. Illness global QoL.

The following modified QLQ-C30 Version 1.0 has been used for the recording and assessment of the patient's conditions prior to and after the treatment with CHP.

| THE MODIFIED QLQ-C30 VERSION 1.0 WITH FUNCTIONAL/SYMPTOM SCALES INDICATED | | | |
|---|---|---|---|
| | SCALE | NO | YES |
| 1. Do you have any trouble doing strenuous activities, like carrying a heavy shopping bag or a suitcase? | Physical | 1 | 2 |
| 2. Do you have any trouble taking a long walk? | Physical | 1 | 2 |
| 3. Do you have any trouble take a short walk outside of the house? | Physical | 1 | 2 |
| 4. Do have to stay in bed or a chair for most of the day? | Physical | 1 | 2 |
| 5. Do you need help with eating, dressing, washing yourself or using the toilet? | Physical | 1 | 2 |
| 6. Are you limited in any way in doing either your work or doing household jobs? | Role | 1 | 2 |
| 7. Are you completely unable to work at a job or to do household jobs? | Role | 1 | 2 |
| | Role | 1 | 2 |

During the past 4 weeks:

| | | | | | |
|---|---|---|---|---|---|
| 1. Mobility | Level of independence | 1 | 2 | 3 | 4 |
| 2. Activities of daily living | | | | | |
| 3. Dependence on medicinalsubstances and medical aids | | | | | |
| 4. Work capacity | | | | | |
| 5. Were you tired? | Fatigue | 1 | 2 | 3 | 4 |
| 6. Did you need rest? | Fatigue | 1 | 2 | 3 | 4 |
| 7. Have you felt weak? | Fatigue | 1 | 2 | 3 | 4 |
| 8. Have you had trouble sleeping? | Insomnia | 1 | 2 | 3 | 4 |
| 9. Have you lacked appetite? | Appetite Loss | 1 | 2 | 3 | 4 |
| 10. Have you had pain? | Pain | 1 | 2 | 3 | 4 |
| 11. Did pain interfere with you daily activities? | Pain | 1 | 2 | 3 | 4 |
| 12. Have you had difficulty in concentrating on things, like reading a newspaper or watching television? | Cognitive | 1 | 2 | 3 | 4 |
| 13. Have you had difficulty remembering things? | Cognitive | 1 | 2 | 3 | 4 |
| 14. Did you worry? | Emotional | 1 | 2 | 3 | 4 |
| 15. Did you feel irritable? | Emotional | 1 | 2 | 3 | 4 |
| 16. Did you feel depressed? | Emotional | 1 | 2 | 3 | 4 |
| 17. Did you feel tense? | Emotional | 1 | 2 | 3 | 4 |
| 18. Has your physical condition or medical treatment interfered with your family life? | Social | 1 | 2 | 3 | 4 |
| 19. Has your physical condition or medical treatment interfered with your social activities? | Social | 1 | 2 | 3 | 4 |

Results from Example 13 and Discussion

TABLE 25

Results from example 26 on physical, cognitive conditions and quality of life (QoL)
GLOBAL HEALTH STATUS 1. How would you rate your overall Physical Condition during the past 4 weeks?
1 = Very poor 7 = Excellent

| | 1 | 2 | 3 | 4 | 5 | 6 | 7 |
|---|---|---|---|---|---|---|---|
| I. Pre Dose | | 2 | 3 | 3 | 0 | 0 | 0 |
| II. After completion of treatment | 0 | 1 | 1 | 5 | 1 | 0 | |

2.. How would you rate your overall Cognitive Conditions during the past 4 weeks?
1 = Very poor 7 = Excellent

| | 1 | 2 | 3 | 4 | 5 | 6 | 7 |
|---|---|---|---|---|---|---|---|
| I. Pre-Dose | | 4 | 3 | 1 | 0 | 0 | 0 |

TABLE 25-continued

Results from example 26 on physical, cognitive conditions
and quality of life (QoL)
GLOBAL HEALTH STATUS

| | | | | | | |
|---|---|---|---|---|---|---|
| II. After completion of treatment | 0 | 1 | 3 | 3 | 1 | 0 |
| 3 How would you rate your overall Quality of Life (QoL) during the past 4 weeks? 1 = Very poor 7 = Excellent | | | | | | |
| Pre Dose | 2 | 3 | 4 | 5 | 6 | 7 |
| | 5 | 3 | 0 | 0 | 0 | 0 |
| II. After completion of treatment | 0 | 0 | 3 | 3 | 2 | 0 |

Scale 1: Very poor, Scale 7: Excellent

Surprisingly and unexpected that the repeated administration of oral and/or intravenous CHP for (90-540 consecutive days 2-12 gram per day) monotherapy to patients with mild or moderate Alzheimer's disease and Dementis has shown significant improvement of the following conditions and quality of life in comparison to their status prior to the start of the treatment:

Cognitive Conditions
Concentrating on things like reading a newspaper or watching television, Remembering things, Drug compliance, Awareness of self
Physical Condition
Work capacity, daily activities (eating, dressing, washing, toilet, shopping, doing household jobs, travelling, walking)
Emotional Conditions
Feeling and mood, Tense, Worry, Depression, Pain, Fatigue, Enjoyment of activities Social interactions, Sleeping, Appetite
Global Quality of Life Only mild adverse events by few patients have been observed, but without any clinical significance.

The invention claimed is:

1. A method for treating or inhibiting dementia associated with a condition other than Alzheimer's disease in a subject, comprising: administering orally a pharmaceutical composition having the structure of cis-4-hydroxy-L-proline (CHP) to the subject at a dose of between about 0.02 mg/kg body weight per day to about 400 mg/kg body weight per day.

2. The method of claim 1, wherein the treatment of dementia is prophylactic.

3. The method of claim 1, wherein the dementia is caused by and/or associated with neurodegenerative and/or neuromuscular disease.

4. The method of claim 1, wherein the dementia is caused by and/or associated with Parkinson's disease.

5. The method of claim 1, wherein the dementia is caused by and/or associated with one of Lewy body disease, Pick's disease, Huntington's disease, Creuzfeld-Jakob disease, a brain tumor, hypothyroidism, head trauma, multiple sclerosis, prolonged abuse of alcohol or other drugs, hydrocephalus, AIDS, vitamin deficiency, fibrotic processes, genetic defects or hypercalcemia.

6. The method of claim 1, wherein the composition is administered as one of a transbuccal formulation, a sublingual formulation, a transmucosal formulation or a sustained release (SR) formulation.

7. The method of claim 1, wherein the composition is administered in a formulation comprising nanoparticles.

8. The method of claim 7, wherein the nanoparticles are selected from the group consisting of liposomes, siosomes, niosomes and combinations thereof.

9. The method of claim 1, wherein the composition is administered at a single and/or multiple dose and each dose comprises 0.10 to 24 g of CHP.

10. The method of claim 1, wherein the composition is administered in combination with dementia therapy in patients with symptoms of dementia.

11. The method of claim 1, wherein the treatment comprises administration of a pharmaceutically effective dose of a second agent.

12. The method of claim 11, wherein the second agent is selected from at least one of the group consisting of a proline derivative, or a salt, ester, isomer, enantiomer, racemate or pro-drug thereof, beta-myeloid inhibitors, Anti-CTGF therapeutics, amino acids, neurotransmitters, vitamins, caffeine, antifibrotic agents, memory activating agents, neuroprotective agents, glutamate-antagonist glutathione, anti-Alzheimer's disease agents, antioxidants, NMDA receptor antagonist, anti-AIDS drugs, antipsychotic drugs, antidepressants, mood stabilizers, anticonvulsants, antigens, antibodies, genetic materials catecholamines, hormones, and sympatholytic adrenergic blocking agents.

13. The method according to claim 9, wherein the composition is administered at a single and/or multiple dose and each dose comprises 2 to 14 g of CHP.

14. The method according to claim 1, wherein the composition is administered to a subject with a CHP deficiency, wherein said deficiency is determined by measuring CHP levels in a sample obtained from said subject.

15. The method according to claim 1, comprising additionally therapy monitoring, wherein after administration of the composition, the levels of CHP are measured in a sample obtained from said subject.

* * * * *